(12) United States Patent
Barsky et al.

(10) Patent No.: US 6,998,513 B1
(45) Date of Patent: Feb. 14, 2006

(54) HUMAN INFLAMMATORY BREAST CARCINOMA XENOGRAFT CAPABLE OF LYMPHOVASCULAR INVASION AND METHODS FOR ITS USE

(75) Inventors: Sanford H. Barsky, Los Angeles, CA (US); Mary L. Alpaugh, Los Angeles, CA (US); James S. Tomlinson, Santa Monica, CA (US)

(73) Assignee: The Regents of the University of California, Oakland, CA (US)

( * ) Notice: Subject to any disclaimer, the term of this patent is extended or adjusted under 35 U.S.C. 154(b) by 387 days.

(21) Appl. No.: 09/856,104

(22) PCT Filed: Sep. 15, 2000

(86) PCT No.: PCT/US00/25299

§ 371 (c)(1),
(2), (4) Date: May 16, 2001

(87) PCT Pub. No.: WO01/19967

PCT Pub. Date: Mar. 22, 2001

Related U.S. Application Data

(60) Provisional application No. 60/154,408, filed on Sep. 17, 1999.

(51) Int. Cl.
*A01K 67/00* (2006.01)
*A01K 67/033* (2006.01)
*A61K 49/00* (2006.01)
*C12N 5/00* (2006.01)
*C12N 5/08* (2006.01)

(52) U.S. Cl. .................. 800/10; 424/9.1; 424/9.2; 435/325; 435/366; 435/371; 435/383; 800/8; 800/9

(58) Field of Classification Search .............. 800/8, 800/3, 10; 623/1.1, 8; 435/325, 7.1, 70.1, 435/366, 371, 383; 424/93.1, 152.1, 9.1, 424/9.2
See application file for complete search history.

(56) References Cited

U.S. PATENT DOCUMENTS 5,508,188 A    4/1996   Barsky et al.

OTHER PUBLICATIONS

Saadi et al.; MiniReview Immunology of Xenotransplantation; Life Sciences, vol. 62, No. 5, pp 365-387, 1998.*
Gill; Use of Small Animal Models for Screening Immunoisolation Approaches to Cellular Transplantation; Screening Immunoisolation: pp 35-46.*
Kleer et al.; Review: Molecular biology of breast cancer metastasis inflammatory breast cancer: clinical syndrome and molecular determinanants; Breast Cancer Res 2000, 2:423-429.*
Kleer et al.; Presistent E-Cadherin Expression in Inflammatory Breast Cancer; Mod Pathol 2001; 14(5):458-464.*
Gura et al. (1997) Systems for identifying new drugs are often faulty. Science 278: 1041-1042.*
Chrysogelos, S.A., "Chromatin Structure of EGRF Gene Suggests a Role for Intron 1 Sequences in its Regulation in Breast Cancer Cells", *Nucleic Acids Research*, 1993, vol. 21, No. 24, pp. 5736-5741.
Schiemann, S. et al., "Molecular Analysis of Two Mammary Carcinoma Cell Lines at the Transcriptional Level as a Model System for Progression of Breast Cancer", *Clinical Experimental Metastasis*, 1998, vol. 16, pp. 129-139.
Brunner, N. et al., Effect of Endocrine Therapy on Growth of T61 Human Breast Cancer Xenografts is Directly Correlated to a Specific Down-Regulation of Insulin-Like Growth Factor II (IGF-II). *European Journal of Cancer*, 1993, vol. 29A, No. 4, pp. 562-569.
Guerin, M. et al., "Structure and Expression of c-erb B-2 and EGF Receptor Genes in Inflammatory and Non-Inflammatory Breast Cancer: Prognostic Significance", *International Journal of Cancer*, 1989, vol. 43, pp. 200-208.
Shao, M. et al., "A Human Inflammatory Breast Carcinoma Xenograft Model of the Intravasation Step of Metastasis", FASEB Journal, Mar. 12, 1999, vol. 13, No. 4 Part 1, pp. A187, Abstract No. 174.9.
Chun, M., "Plasmin Induces the Formation of Multicellular Spheroids of Breast Cancer Cells", *Cancer Letters*, 1997, vol. 117, pp. 51-56.

* cited by examiner

*Primary Examiner*—Anne-Marie Falk
(74) *Attorney, Agent, or Firm*—Gates & Cooper LLP

(57) ABSTRACT

The present invention provides human transplantable inflammatory breast carcinoma xenografts. Such xenografts exhibit a number of unique characteristics which allows their use in experimental models of inflammatory carcinoma in order to dissect out the molecular basis of this phenotype. This experimental model of inflammatory carcinoma can be used to identify molecular targets for therapeutic intervention and to assess the efficacy of a broad spectrum of diagnostic and therapeutic agents. Specific animal models of inflammatory breast cancer are described as well as methods for evaluating diagnostic and therapeutic agents for treating inflammatory breast cancer. Methods for identifying molecules whose expression is modulated in inflammatory breast cancer are provided. In addition, methods for diagnosing and inhibiting the growth of inflammatory breast cancer metastases in vivo are provided.

17 Claims, 15 Drawing Sheets

*a*

*b*

A

B

C

*d*

*e*

HUMAN INFLAMMATORY BREAST CARCINOMA XENOGRAFT CAPABLE OF LYMPHOVASCULAR INVASION AND METHODS FOR ITS USE

This application claims the benefit of U.S. provisional patent application Ser. No. 60/154,408, filed Sep. 17, 1999. The entire content of this provisional patent application is incorporated herein by reference.

FIELD OF THE INVENTION

The present invention relates to the use of inflammatory breast carcinoma xenografts as models for both the evaluation of the cancer phenotype as well as the generation of novel diagnostic and therapeutic methods for the clinical management of this pathology.

BACKGROUND OF THE INVENTION

Cancers of the breast are one of the leading causes of death among women, with the cumulative lifetime risk of a woman developing breast cancer estimated to be 1 in 9. Consequently, understanding the origins of these malignancies as well as models for the identification of new diagnostic and therapeutic modalities is of significant interest to health care professionals.

Most women that die from breast cancer succumb not to the original primary disease, which is usually amenable to various therapies, but rather from metastatic spread of the breast cancer to distant sites. This fact underscores the need to develop either novel anticancer agents or more aggressive forms of therapy directed specifically against the metastatic breast tumor cell. Requisite to the development of new treatment modalities is a fundamental, thorough understanding of the regulatory processes inherent to the growth of both the primary and metastatic breast cancer cell and tumor. This process has been severely hampered by the lack of appropriate and clinically relevant modeling systems.

Recent experimental studies have suggested that the step of intravasation is a rate limiting though poorly understood step of the metastatic process (Kim et al., Cell, 94: 353–362, 1998; Quigley et al., Cell, 94: 281–284, 1998.). Inflammatory breast carcinoma is a representative cancer in humans which exhibits an exaggerated degree of intravasation in situ manifested by florid invasion of lymphatic and vascular capillaries. Inflammatory breast cancer is one of the most aggressive types of human breast cancer (Levine et al., J. Natl. Cancer Inst., 74: 291–297, 1985.). Clinically patients present with an inflamed tender breast with the so called erysipelas edge and/or peau d'orange. Pathologically there is extensive lymphovascular invasion by tumor emboli which involve the superficial dermal plexus of vessels in the papillary dermis and high reticular dermis. Inflammatory carcinomas tend to exhibit axillary nodal metastases, a high incidence of local and systemic recurrence and distal metastases. Inflammatory carcinomas can occur in either primary or secondary forms, the latter term referring to a non-inflammatory primary carcinoma which recurs as an inflammatory carcinoma. Locally advanced non-inflammatory primary cancers which are successfully treated with neo-adjuvant chemotherapy often show evidence microscopically of residual carcinoma presently almost exclusively in lymphovascular channels.

In view of the above, what is needed in the art are novel models for the evaluation, diagnosis and generation of therapies for metastatic cancers, in particular inflammatory breast cancer. In this context, optimal models are those which provide insight into metastatic processes such as intravasation, as these models have a wide application both in the diagnosis of cancer, as well as the generation of prophylactic and therapeutic treatments for cancer.

SUMMARY OF THE INVENTION

The inventions disclosed herein relate to human transplantable inflammatory breast carcinoma xenografts. Such xenografts exhibit a number of unique characteristics which allows the skilled artisan to use them in experimental models of inflammatory carcinoma in order to dissect out the molecular basis of this phenotype. Moreover, this experimental model of inflammatory carcinoma can be used to identify molecular targets for therapeutic intervention and to assess the efficacy of a broad spectrum of diagnostic and therapeutic agents.

One embodiment of the invention consists of a human inflammatory breast cancer xenograft, where the xenograft grows within lymphatic and blood vessel channels, does not express estrogen receptor and progesterone receptor and expresses P53, EGFR, MUC1 and E-cadherin. In a preferred embodiment, the level of E-cadherin expressed by the xenograft is at least two-fold greater than the level of E-cadherin expressed by a noninflammatory breast cancer xenograft. In a related embodiment, the levels of $\alpha$-catenin and $\beta$-catenin expressed by the xenograft are at least two-fold greater than the levels of $\alpha$-catenin and $\beta$-catenin expressed by a noninflammatory breast cancer xenograft. In another related embodiment, the xenograft does not express Her-2/neu. In a highly preferred embodiment the xenograft is the human inflammatory breast carcinoma xenograft designated MARY-X. A related embodiment of the disclosed invention consists of an in vitro culture of a human inflammatory breast cancer xenograft, wherein the xenograft grows as a spheroid and can attach to cell monolayers. In another related embodiment of the invention, the spheroid disadheres from the cell monolayer when exposed to a culture media containing absent $Ca^{++}$ or anti-E-cadherin antibody. Methods for generating the disclosed xenografts are also described.

Another embodiment of the invention consists of methods of identifying a molecule whose expression is modulated in inflammatory breast cancer by determining the level of expression of at least one molecule in the human inflammatory breast cancer xenograft; and comparing this to the level of expression of the same molecule in a cell having characteristics which are distinct from the human inflammatory breast cancer xenograft. In preferred embodiments of this invention, the level of expression of the molecule of the inflammatory breast cancer xenograft is determined by methods selected from the group consisting of: Northern blotting, Southern blotting, Western blotting and polymerase chain reaction.

Yet another embodiment of the invention consists of an animal model for inflammatory breast cancer comprising an immunocompromised host animal inoculated with a human inflammatory breast cancer xenograft. In preferred embodiments of this invention, the host animal is a nude mouse and the xenograft is the xenograft designated MARY-X.

Another embodiment of the invention consists of methods for evaluating at least one agent for treating inflammatory breast cancer by utilizing a immunocompromised host animal inoculated with a human inflammatory breast cancer xenograft, administering at least one agent to said inoculated immunocompromised host animal and evaluating the effects of the agent(s) on the human inflammatory breast cancer xenograft. Optionally, the agent that is being evaluated targets a molecule that is identified as being associated with the inflammatory phenotype. Yet another related embodiment of the invention consists of methods for evaluating the potential of an agent, or a combination of agents, for the prevention of lymphovascular invasion of carcinoma cells by utilizing a immunocompromised host animal inoculated with a human inflammatory breast cancer xenograft, administering at least one agent to said inoculated immunocompromised host animal and evaluating the effectiveness of said agent or said combination of agents in the prevention of lymphovascular invasion. In preferable embodiments of these inventions, the immunocompromised host animal is a nude mouse and the human inflammatory breast cancer xenograft is the xenograft designated MARY-X. Optionally the agent evaluated is an antibody or an angiogenic inhibitor.

Another embodiment of the invention consists of methods of inhibiting the growth of inflammatory breast cancer in vivo by administering an effective amount of an anti-E-cadherin antibody so that the growth of an inflammatory breast cancer metastases is inhibited. A related embodiment consists of methods of detecting and monitoring inflammatory breast cancer in vivo by administering an effective amount of an anti-E-cadherin antibody so that the inflammatory breast cancer metastases is detected. In preferred embodiments of this invention, the antibody is joined to a cytotoxic agent or labeled with a detectable marker.

DETAILED DESCRIPTION OF THE INVENTION

Figure 1:
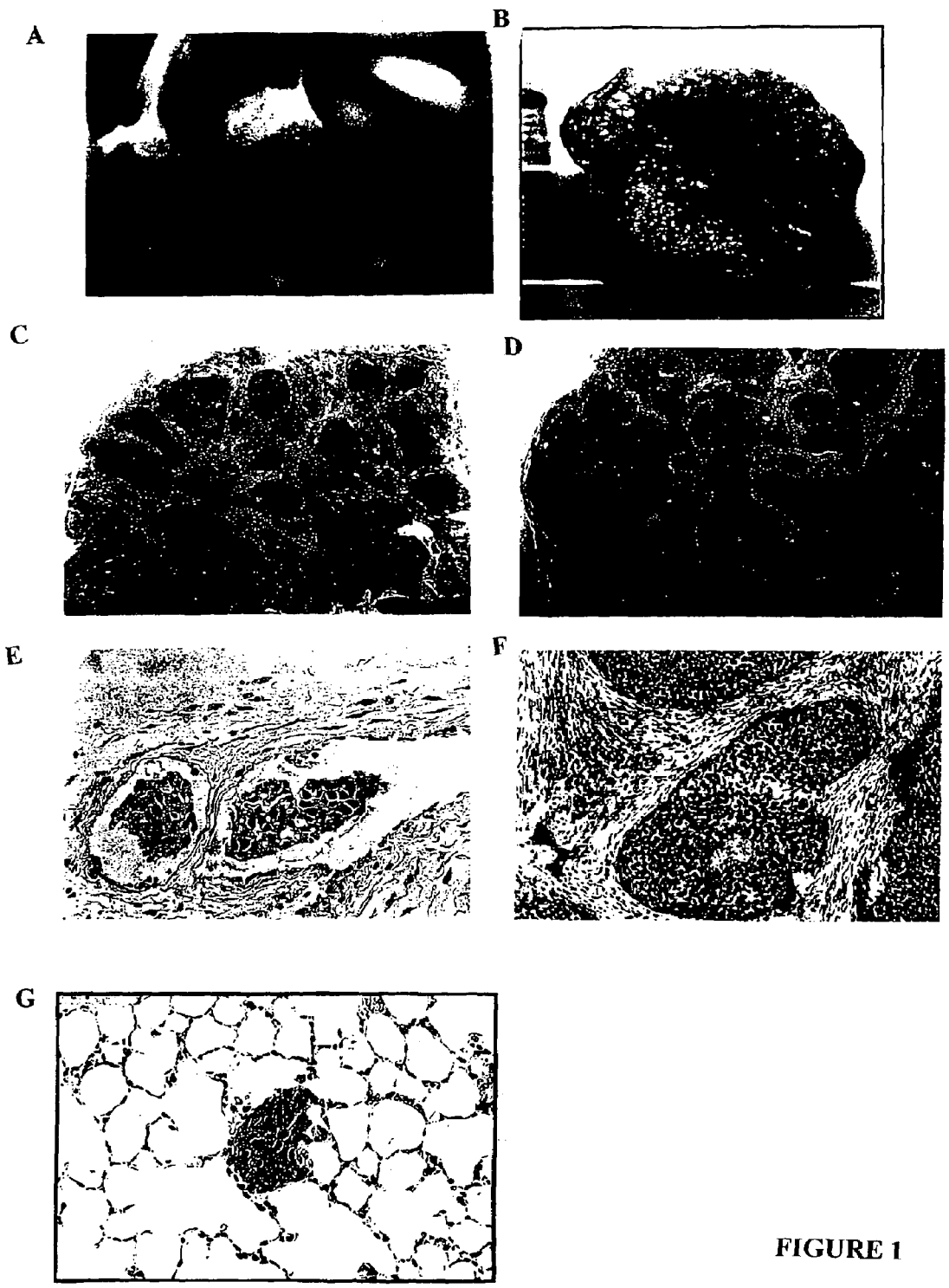
FIG. 1: As can he observed in color photographs, MARY-X turns the overlying murine skin bright red (A). MARY-X consists grossly of a confluence of white nodules (B) which correspond to distended lymphovascular channels filled with tumor emboli (C). These vascular channels represent lymphatics and blood vessels and demonstrate von Willebrand factor immunoreactivity as depicted by circumferential brown staining in color photographs. Higher magnification of MARY-X depicts lymphovascular invasion (D). Interestingly MARY-X exhibits only the step of intravasation in both the primary tumor as well as in pulmonary metastases (E) but the pulmonary emboli do not extravasate and establish true pulmonary metastases even after prolonged time periods.

The term "antibody" is used in the broadest sense and specifically covers single monoclonal antibodies and antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies discussed herein include hybrid and recombinant antibodies produced by splicing a variable (including hypervariable) domain of an anti-E-cadherin antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. See, e.g. U.S. Pat. No. 4,816,567 and Mage et al., in Monoclonal Antibody Production Techniques and Applications, pp. 79–97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature, 256:495 (1975), or may be made by recombinant DNA methods such as described in U.S. Pat. No. 4,816,567. The "monoclonal antibodies" may also be isolated from phage libraries generated using the techniques described in McCafferty et al., Nature, 348:552–554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

Disclosed herein is the first human transplantable inflammatory breast carcinoma xenograft (MARY-X). As described in detail below, MARY-X exhibits an number of unique characteristics which allows the skilled artisan to use this exemplary xenograft as an experimental model of inflammatory carcinoma to dissect out the molecular basis of this phenotype. Moreover, this experimental model of inflammatory carcinoma can be used to identify molecular targets for therapeutic intervention and to assess the efficacy of a broad spectrum of diagnostic and therapeutic agents.

The MARY-X Inflammatory Breast Xenograft

Disclosed herein is the first human transplantable inflammatory breast carcinoma xenograft (MARY-X). As disclosed below, the xenografts described herein encompass a number of embodiments. One embodiment of the invention consists of a human inflammatory breast cancer xenograft, where the xenograft grows within lymphatic and blood vessel channels, does not express estrogen receptor and progesterone receptor and expresses P53, EGFR, MUC1 and E-cadherin. In a preferred embodiment, the level of E-cadherin expressed by the xenograft is at least two-fold greater than the level of E-cadherin expressed by a noninflammatory breast cancer xenograft. In a related embodiment, the levels of α-catenin and β-catenin expressed by the xenograft are at least two-fold greater than the levels of α-catenin and β-catenin expressed by a noninflammatory breast cancer xenograft. In another related embodiment, the xenograft does not express Her-2/neu. In a highly preferred embodiment the xenograft is the human inflammatory breast carcinoma xenograft referred to as MARY-X deposited with the American Type Culture Collection Manassas, Virginia on Nov. 29, 2000, and assigned ATCC Patent Deposit No. PTA-2737). A related embodiment of the disclosed invention consists of an in vitro culture of a human inflammatory breast cancer xenograft, wherein the xenograft grows as a spheroid and can attach to cell monolayers (deposited with the American Type Culture Collection Manassas, Virginia on Nov. 29, 2000, and assigned ATCC Patent Deposit No. PTA-2736). In a preferred embodiment of the invention, the spheroid disadheres from the cell monolayer when exposed to a culture media containing absent $Ca^{++}$ or anti-E-cadherin antibody.

In order to assess the constellation of characteristics associated with the MARY-X xenograft, studies of tumorigenicity, growth rate, animal-associated characteristics, patterns of metastasis, tumor histology, immunocytochermistry and molecular characterizations were conducted on MARY-X and compared to studies on established noninflammatory xenografts including the MDA-MB-231 and MDA-MB-468 breast carcinoma xenografts and our human myoepithelial xenografts (HMS-X, HMS-3X, HMS-4X), which we had previously established (Sternlicht et al., In Vitro Cell. Dev. Biol., 32: 550–563, 1996, Sternlicht et al., Clin. Cancer Res., 3: 1949–1958, 1997; Shao, et al., Exp. Cell Res., 241: 394–403, 1998).

As described in detail below, the MARY-X cell line exhibits a number of unique characteristics which allows the skilled artisan to use this in this experimental model of inflammatory carcinoma to assess the molecular basis of this phenotype. Remarkably MARY-X induced erythema in the overlying mouse skin (FIG. 1A) mimicking the clinical presentation of inflammatory carcinoma. While all other human xenografts grow as isolated subcutaneous nodules, MARY-X grows exclusively within murine lymphatic and blood vessel channels (FIGS. 1B, 1C, 1D). MARY-X's supporting stroma comprises, by murine Cot-1 DNA analysis, 30% of the tumor. MARY-X, like its human counterpart exhibits striking erythema of the overlying skin. Confirmation of the vascular identity of these channels was on the basis of von Willebrand factor immunoreactivity. Analysis of the lungs of mice with large MARY-X tumors (1.5–2.0 cm diameter) reveals the presence of pulmonary metastases but surprisingly these metastases were confined to within vessels (FIG. 1E). No extravasation of these pulmonary metastases occurs. The phenotype of MARY-X is therefore limited to intravasation. This phenotype has remained stable in over 15 transplant generations.

Figure 3:
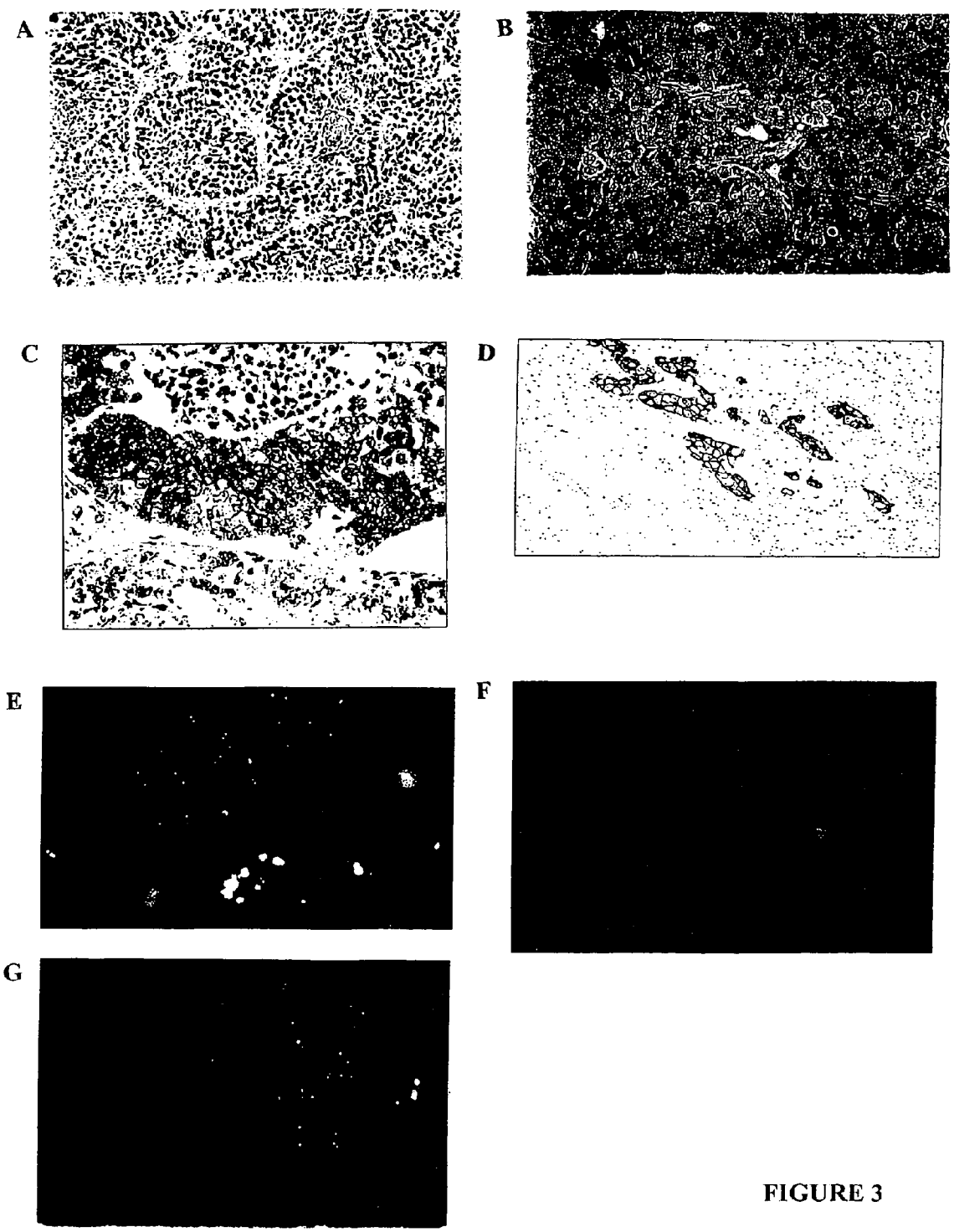
FIG. 3: MARY-X was p53 positive (A), ER negative (B), PR negative, EGFR positive (C), and HER-2/neu negative. MARY-X's primary tumor of origin however showed Her-2/neu amplification by immunocytochemistry (D) and FISH (E) in a significant fraction of its cells. In color photographs of this FISH data, strong yellow-orange fluorescence (fluorophore SpectrumOrange™) is depicted in the cell population at the lower portion of the slide (E). Cell population at the upper portion shows unamplified Her-2/neu. A chromosome 17-specific centromeric α-satellite probe (D17Z1) revealed normal ploidy in all of these areas. FISH reveals that MARY-X has completely lost the Her-2/neu amplified population (F).

MARY-X, like MDA-MB-231 and MDA-MB-468, is ER, PR, Her-2/neu negative and p53, EGFR positive (FIG. 3A, 3B, 3C, 3D, 3E, 3F). Some of these markers stained homogeneously and some, in fact, were quite heterogeneous. p53 immunostaining was present in nearly 100% of the cells; ER and PR staining was 100% absent; EGFR was strongly immunoreactive in 20% of the cells. MARY-X's primary tumor of origin exhibited identical markers as MARY-X with the exception of Her-2/neu. About 50% of MARY-X's primary tumor show a marked Her-2/neu amplification by both immunocytochemical staining (FIG. 3D) and FISH (FIG. 3E). MARY-X, however, shows no evidence of Her-2/neu amplification (FIG. 3F) despite maintaining its inflammatory signature of florid lymphovascular invasion. We then compared MARY-X to common non-inflammatory xenografts with respect to angiogenic, proteolytic and adhesion molecules and discovered a striking overexpression of E-cadherin (5–10 fold) and the plaque proteins, α-, β-catenin (5 fold). Increased E-cadherin membrane immunoreactivity was confirmed in actual human cases. In MARY-X, the E-cadherin and catenins were part of a structurally and functionally intact adhesion axis involving the actin cytoskeleton. In vitro, MARY-X grew as round compact spheroids with a cell density 5–10 fold higher than other E-cadherin expressing breast carcinoma cell lines. The spheroids of MARY-X completely disadhered when placed in media containing absent $Ca^{++}$ or anti-E-cadherin antibodies or when retrovirally transfected with a dominant-negative E-cadherin mutant (H-2 $K^d$-E-cad). Intravenously injected anti-E-cadherin antibodies immunolocalized specifically to the pulmonary lymphovascular emboli of MARY-X and caused their dissolution. H-2 $K^d$-E-cad transfected MARY-X spheroids were only weakly tumorigenic and non-lymphovascular emboli forming. 90% of human ibc's showed increased membrane E-cadherin/α,β-catenin immunoreactivity. These findings indicate that it is the gain and not the loss of the E-cadherin axis that contributes to the ibc phenotype.

DNA fingerprinting, the canonical method of proving that a cell line or xenograft is original served also to demonstrate that MARY-X had a significant (>30%) murine component (FIG. 2A, 2B), presumably due to murine vessels and their supporting stroma. Once established, MARY-X manifested 100% tumorigenicity with a latency of approximately 1 week and grew fairly rapidly (FIG. 2C). This growth however was confined to lymphovascular spaces. A human-specific Cot-1 DNA probe documented human DNA in MARY-X. Using a murine-specific Cot-1 probe, the murine component of MARY-X could be quantitated and compared to the murine component of other human xenografts and MARY-X demonstrated the greatest murine percentage (>30%) (FIG. 2D), presumably from its murine lymphovascular component and supporting stroma. We were able to effectively separate the human tumor cells from the murine vascular component utilizing the MARY-X "shake" in vitro which generates a population of cells that is 98–99% human (FIG. 2D). Subsequent studies on select gene expression of MARY-X is usually done on this MARY-X "shake" to exclude as a source of gene expression the murine vascular component. The MARY-X "shake" produces spheroids which could be maintained as suspension cultures for several months or which could attach to epithelial (HMEC) or endothelial (HUVEC) monolayers. These spheroids remained viable for periods up to 3 months but showed evidence of hypoxia and necrosis in their centers after approximately 4 weeks in culture (FIG. 2E).

Figure 4:
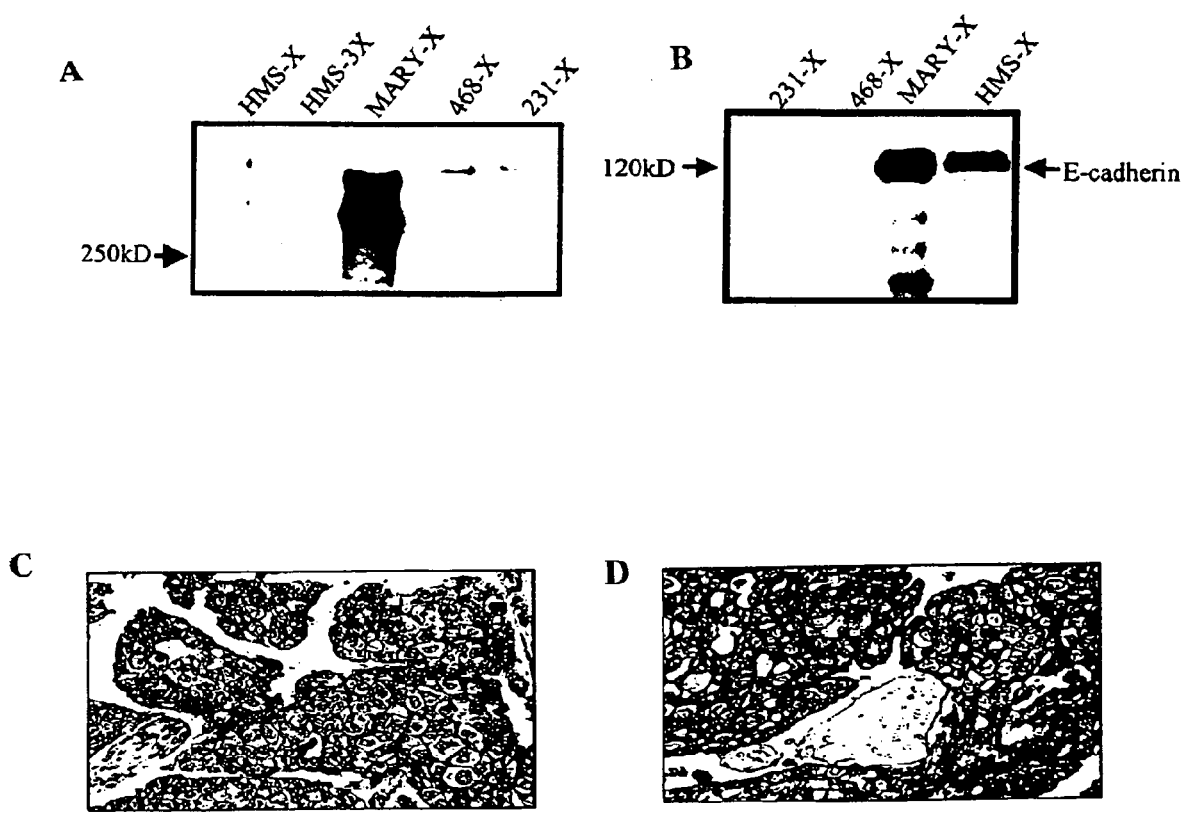
FIG. 4: Comparative studies on MARY-X revealed marked overexpression of MUC1 (A) and E-cadherin (B) by Western blot. Cases of human inflammatory breast cancer exhibited similar overexpression of MUC1 and E-cadherin. This overexpression was manifested by intense E-cadherin membrane immunoreactivity (C) and strong MUC1 membrane and cytoplasmic immunoreactivity (D).
Figure 5:
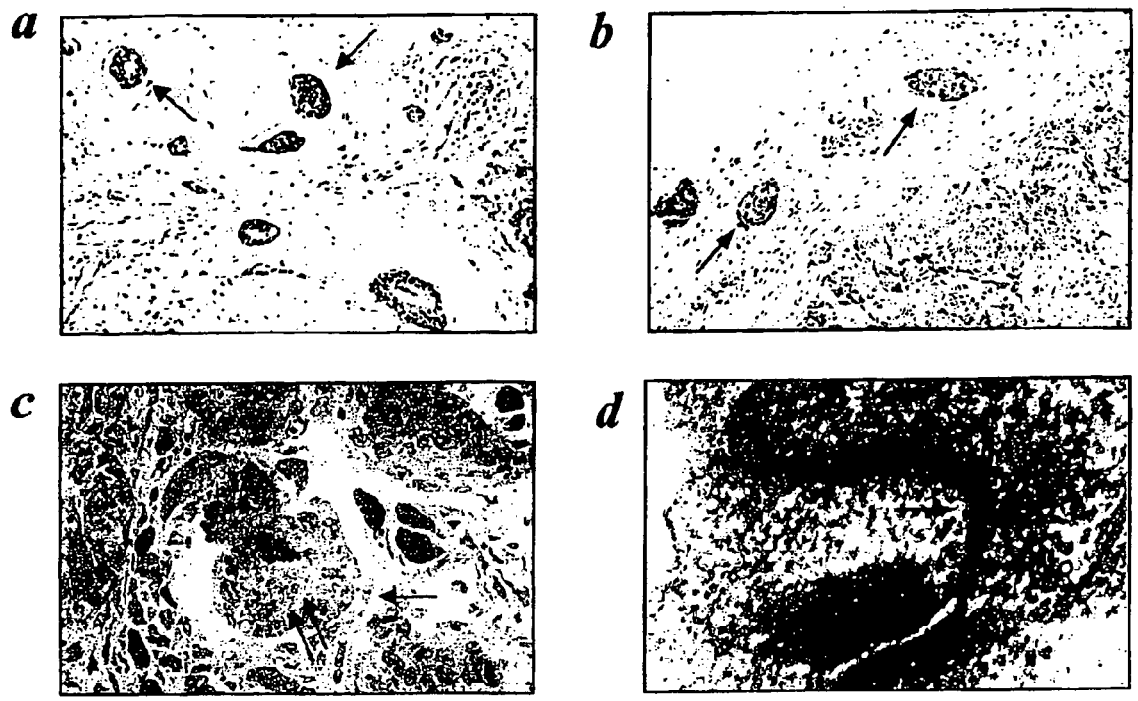
FIG. 5: a, Lymphovascular invasion in primary inflammatory breast carcinoma is characterized by numerous tumor emboli in lymphovascular spaces (arrows). b, MARY-X exhibits similar lymphovascular invasion (arrows). c, tumor cell-tumor cell adhesion (double arrows) and tumor cell-endothelial cell adhesion (arrow) within a lymphovascular embolus of MARY-X are suggested by this epon-embedded section. d, tumor cell-tumor cell interface of MARY-X illustrates prominent adherens junctions (arrows), presumed sites of E-cadherin and the plaque proteins, α-catenin and β-catenin.

As inflammatory carcinomas manifest striking lymphovascular invasion, it is likely that they stimulate angiogenesis/lymphangiogenesis and then manifest lymphovascular "homing". It is also likely that the molecular mechanism(s) of this effect involve adhesion molecules either on tumor cells or endothelial cells or angiogenic growth factors and proteolytic enzymes elaborated by tumor cells which enable intravasation. For these reasons, we conducted an initial screen of candidate effector molecules previously implicated in the above mentioned processes. These molecules included candidate adhesion molecules of the integrin family, the immunoglobulin superfamily and other adhesion molecules; candidate angiogenic factors of the VEGF, FGF and TGF families; and candidate proteases and their receptors including serine and metalloproteinases. Of these molecules examined, two initially stood out: MUC1 and E-cadherin. MARY-X compared to non-inflammatory xenografts markedly overexpressed (10–20 fold) MUC1 (FIG. 4A) and E-cadherin (FIG. 4B). These findings on Western blot were confirmed in both immunocytochemical studies of MARY-X and in actual cases of human inflammatory breast cancer. Lymphatic tumor emboli of inflammatory carcinoma manifested strong membrane E-cadherin immunoreactivity (FIG. 4C) and strong cytoplasmic and membrane MUC1 immunoreactivity (FIG. 4D) in 100% of the cases of human inflammatory carcinoma which were examined. Interestingly, increased membrane E-cadherin immunolocalization was also observed in cases of non-inflammatory breast carcinoma but only in their foci of lymphovascular invasion.

The inflammatory carcinoma phenotype displayed by MARY-X is characterized by homophilic tumor emboli present within lymphovascular spaces, and is consistent with the mechanisms involving adhesion molecules on tumor cells and/or angiogenic factors and/or proteolytic enzymes elaborated by tumor cells, all of which facilitate intravasation. Our present studies comparing MARY-X with non-inflammatory breast carcinoma xenografts, MDA-MB-231, MDA-MB-468 and the human myoepithelial xenograft, HMS-3X and reveal that the two major differences are the marked overexpression of MUC-1 (10–20 fold) and E-cadherin (5–10 fold) (FIG. 6a, 6b, 6c) in MARY-X (Sternlicht et al., *In Vitro Cell. Dev. Biol.* 32, 550–563 (1996); Sternlicht et al., *Clin. Cancer Res.* 3, 1949–1958 (1997); Sternlicht et al., *Lab. Invest.* 74, 781–796 (1996). This overexpression is even more marked in the MARY-X "shake" indicating that the source of this overexpression is the human carcinoma cells themselves and not the murine stromal or vascular component. While the overexpression of MUC-1 had been observed in many different non-inflammatory breast carcinomas (see e.g. O'Connell et al., *Human Pathology* 29, 1517–1523 (1998)), but overexpression of E-cadherin is a new finding. Moreover, the loss of E-cadherin rather than overexpression was the rule in human breast cancer and human breast cancer cell lines (see e.g. Gumbiner et al., *Cell* 84, 345–357 (1996); Ben-Ze'ev et al., *Current Opin. Cell Biol.* 10, 629–639 (1998); Pierceall et al., *Oncogene* 11, 1319–1326 (1995).

Methods for Generating, Propagating and Harvesting Inflammatory Breast Xenografts Xenografts having an inflammatory phenotype can be generated and propagated according to the methods described in Example 1. For example, methods of generating the inflammatory breast cancer xenograft comprising the steps of obtaining a breast sample from a patient, identifying cells in the sample as an inflammatory carcinoma exhibiting florid invasion of dermal lymphatics, implanting the sample into an immunocompromised host; and identifying the xenograft growing in the immunocompromised host is provided.

A variety of methods relating to the propagation and storage of xenografts are known in the art, and can be applied to the propagation and storage of MARY-X. For example, xenografts such as MARY-X can be grown in 4 week old nude and scid mice. Optimally, about 25 mice can be used to maintain the growth of the tumor as a breeding colony. In this context, the disclosure describes animal models of inflammatory breast cancer comprising an immunocompromised host animal inoculated with a human inflammatory breast cancer xenograft. For example, the disclosure herein provides an animal model for inflammatory breast cancer comprising an immunocompromised host animal inoculated with a human inflammatory breast cancer xenograft, wherein the xenograft grows within lymphatic and blood vessel channels, does not express estrogen receptor and progesterone receptor but does expresses P53, EGFR, MUC1 and E-cadherin. In preferred embodiments of this invention, the host animal is a nude mouse and the xenograft is the xenograft designated MARY-X.

As an illustrative method for the propagation of xenografts for subsequent experimental procedures, groups of about 10 mice each can be used to inject molecules which may effect the tumors such as anti-angiogenesis agents or control and examine the effects of these manipulations on tumor parameters. Mice can be euthanized before the xenograft reaches 1.5 cm in greatest diameter. The method of euthanasia can be cervical dislocation as it is consistent with the Panel on Euthanasia of the American Veterinary Medical Association. Additional mice can be used to grow up MARY-X for subsequent DNA and RNA extractions. Control non-inflammatory xenografts can also be grown in mice following the methods disclosed above.

In order to enrich the MARY-X cellular isolate from the nude mouse environment, one can perform a procedure designated the MARY-X "shake" as outlined in Example 1. In the MARY-X "shake", an enriched population of human tumor cells, substantially free from murine components, can be produced. Human and murine specific probes such as the Cot-1 probe (see below) can be used to verify that the population of cells that result from the MARY-X "shake" is predominantly human.

The continuous cell line of the present invention is described as being cultivated in nude and scid mice. Nonetheless, it should be appreciated by those versed in the art that the continuous xenograft may be cultivated in other suitable athymic nude animals, such as athymic nude guinea pigs and athymic nude rabbits. Likewise, it should be appreciated that certain cell culture mediums are believed to be suitable for temporarily of permanently cultivating xenografts. For example, cells of the xenograft can be placed into cell culture medium following standard procedures, i.e., tissues extracted from the athymic nude mice and minced and single cells can be allowed to grow out of the explants, or tissue can be digested with collagenase/elastase to release single cells, which can then be cultured. Cells can be plated in various enriched media as previously described in, J. Cell. Biol. 100:565–573, 1985 and Solberg, L. A. Jr. et al: J. Cell. Phys. 125:67–74,1985. The media may consist of, for instance, Iscove's modification of Dulbecco's MEM, or RPMI-1640, enriched with human plasma at determined optimal concentrations as well as conditioned media from mononuclear blood cells at a concentration of about 5%. Semisolid cultures in about 0.9% methylcellulose can also be utilized to promote adaptation to tissue culture conditions. Also, it may be desirable to alternate cell growth between cell culture medium and mice for the generation of hormone producing cells.

Methods for Analyzing and Characterizing Inflammatory Breast Xenografts

The invention disclosed herein allows one to analyze the cellular molecular mechanisms of lymphovascular invasion and tumor intravasation, which will lead to better therapies aimed at preventing disease recurrences and treating micrometastases. In this context, a variety of analytical and comparative methodologies for characterizing cells such as the xenografts disclosed herein are known in the art. For example, Gene expression in a xenograft may be measured in a sample directly, for example, by conventional Southern blotting, Northern blotting to quantitate the transcription of mRNA [Thomas, *Proc. Natl. Acad. Sci. USA,* 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence polypeptide or against a synthetic peptide based on the DNA sequences provided herein or against exogenous sequence fused to DNA and encoding a specific antibody epitope.

Example 2 provides a number of illustrative methods for analyzing inflammatory breast xenografts. For example DNA profiling was used to distinguish murine from human DNA and quantitate the murine DNA component of the xenografts. Western blot and zymography analysis was utilized to compare MARY-X with non-inflammatory xenografts with respect to candidate effector molecules. Immunocytochemistry and FISH were also utilized for this purpose.

Methods for Analyzing and Characterizing the Inflammatory Phenotype

The invention disclosed herein allows one to analyze the pathological features of lymphovascular invasion and tumor intravasation, which will lead to better therapies aimed at preventing disease recurrences and treating micrometastases. In this context, a variety of analytical and comparative methodologies for characterizing the pathological features of lymphovascular are provided below.

Analysis of the Vasculature Anatomy Associated with the Inflammatory Phenotype

The xenograft disclosed herein exhibits striking lymphovascular invasion. In fact it does not grow as an isolated tumor nodule but grows exclusively within lymphovascular channels. Some of these channels are lymphatics and some are blood vessels confirmed by anti-vWf factor and anti-CD31 endothelial staining. Interestingly the skin overlying the inflammatory xenograft is intensely erythematous just as it is in humans presumably from the lymphovascular obstruction. In both the athymic (nude) mouse and the Scid in vivo models, the inflammatory carcinoma xenograft exhibits a high degree of spontaneous metastasis as early as 6 weeks following local subcutaneous implantation. In contrast the non-inflammatory xenografts, 231 and 468 grow as isolated tumor nodules exhibiting no lymphovascular invasion and no metastasis. As illustrated below, the unique features of this xenograft allow an in-depth analysis of an inflammatory cancer's vasculature with markers to distinguish lymphatics, angiogenic and old blood vessels. In this context, the effects of anti-angiogenic agents on tumorigenicity, intravasation, hypoxia, necrosis, apoptosis, proliferation, intravasation and vasculature of this inflammatory carcinoma can be examined to gain insights into the angiogenic versus intravasation phenotypes.

Figure 2:
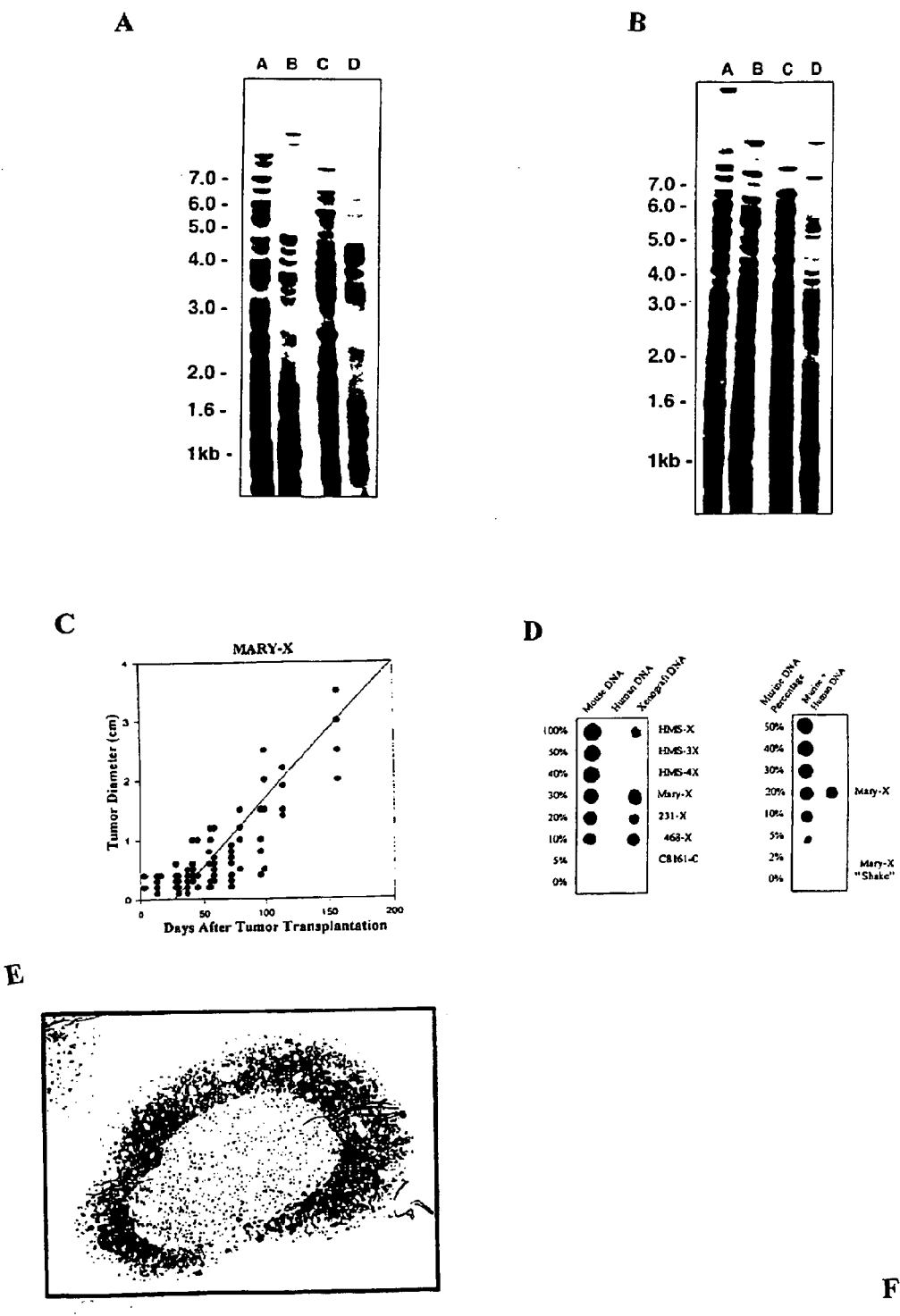
FIG. 2: DNA fingerprints (A,B). DNA from the xenografts, HMS-X (lanes A) and MARY-X (lanes C) and host murine tissues (lanes B, D) were digested with HaeIII (A) and HinfI (B) restriction enzymes and hybridized with the multilocus hypervariable Jeffreys probe 33.6. No murine component was detected in HMS-X (lanes A versus B) whereas a significant murine component is detected in MARY-X as evidence by a number of co-migrating bands (lanes C versus D). MARY-X growth kinetics in nude mice (C). Although MARY-X exhibited fairly rapid tumor growth, its growth was confined to progressive distension and involvement of murine vessels. Using a mouse specific Cot-1 DNA probe (D), human tumoral xenografts HMS-X, HMS-3X, HMS-4X, MDA-MB-231-X, MDA-MB-468-X demonstrated a variable murine component ranging from negligible to significant. MARY-X demonstrated the greatest murine component. A control human melanoma line C8161-C predictably exhibited no murine DNA component. A human tumor cell-enriched fraction of MARY-X, the MARY-X "shake" (E) is compose of spheroids with pale-staining central areas, evidence of hypoxia and necrosis after 4 weeks in suspension culture.

Characterization of the vascular profile of MARY-X. Insights into the issue of whether the angiogenesis and intravasation phenotypes are related or separate can be obtained by an analysis of the vascular profile of MARY-X. By routine light microscopy and hematoxylin and eosin staining, it appears that MARY-X manifests marked tumor cell intravasation that involves both murine lymphatics as well as blood vessels. This observation is based on seeing proteinaceous material in the lumen of vessels containing tumor emboli as indicative of their lymphatic nature and seeing plugs of luminal erythrocytes adjacent to tumor emboli in vessels presumed to be blood vessel capillaries. Both of these channels were lined by cells exhibiting von Willebrand factor immunoreactivity (FIG. 1). These initial observational studies provide evidence that MARY-X invades both lymphatics and blood vessels. Since one common avenue of intravasation most likely involves lymphatics and since there is no evidence to date that lymphangiogenesis occurs in solid tumors (although it occurs during embryological development), the type of lymphatic vessels which are intravasated should be investigated. In this context, one can characterize the vascular profile of MARY-X immunocytochemically with both established and newly discovered markers that have shown promise in distinguishing angiogenic blood vessels from old blood vessels and lymphatic capillaries from blood vessel capillaries. We have conclusively shown that the blood vessels and lymphatics in MARY-X are murine and not human in origin because the purified human MARY-X "shake", when injected into nude or scid mice, produces the inflammatory phenotype of florid lymphovascular invasion which is characterized by a significant (30%) murine component as determined by the murine specific COT-1 probe (FIG. 2). One can use antibodies to markers such as von Willebrand factor (all blood vessels and lymphatics (weaker staining)), CD31 (all blood vessels and lymphatics (weaker staining)), PAL-E, a blood vessel endothelial antigen (all blood vessels), E-selectin (angiogenic blood vessels) and VEGF-3 (all lymphatics). The described specificity of each of these antigens is indicated in parenthesis. One can then quantitate by immunohistochemical staining the class of vessels observed and how many of each class are involved by tumor intravasation (the presence of a tumor embolus). One can determine specifically if MARY-X intravasates predominately in lymphatics, old blood vessels or angiogenic blood vessels. One can then compare MARY-X with the inflammatory carcinoma from which it was derived and also with other human cases of inflammatory carcinoma as a control for variance in vascular staining due to the murine nature of the vessels in MARY-X. One can then use other non-inflammatory breast carcinoma xenografts such as the MDA-MB-231 and the MDA-MB-468 to compare their vascular staining profiles.

Measurements of vascular porosity/permeability. Because another feature of new angiogenic vessels is increased vascular porosity/permeability, one can use the invention described herein to study the extravasation of Evan's blue dye as a marker of vascular permeability and as a surrogate marker of angiogenesis in MARY-X versus other non-inflammatory breast carcinoma xenografts such as the MDA-MB-231 and the MDA-MB-468. If MARY-X contains a large amount of neovascularization, i.e., angiogenesis then the levels of extravasated Evan's blue dye ought to be high; one can compare these levels to levels from the MDA-MB-231 and the MDA-MB-468 xenografts, xenografts thought to exhibit a high degree of angiogenesis but no or minimal intravasation. One can also compare the levels in MARY-X to those observed with our myoepithelial xenografts, HMS-X, HMS-3X and HMS-4X, xenografts observed to exhibit no or little murine angiogenesis. If the levels of extravasated dye are low in MARY-X it will provide evidence that there is only a low level of angiogenesis and that the preponderance of intravasation is occurring in non-angiogenic vessels (either old blood vessels or lymphatics).

With tumors of varying sizes, 0.3 cm to 1.5 cm, Evans blue dye (20 $\mu$g/g) can be injected into the mice via the tail vein followed by extirpation of the xenografts 60 minutes later. The dye can be extracted by placing the extirpated xenografts in formamide (4 ml/g) and the concentration of Evan's blue dye determined spectrophotometrically at 620 nm wavelength using an ELISA reader.

Effects of angiogenic inhibitors on MARY-X and its vasculature. One way to dissect the angiogenic from intravasation phenotypes is to administer several different angiogenic inhibitors to the mice. These inhibitors can include thalidomide, TNP-470, angiostatin and endostatin, all of which have been shown to inhibit the growth of angiogenic-dependent tumors. The use of these angiogenic inhibitors will help us dissect the angiogenic from intravasation phenotypes. One can then study numerous tumor parameters including tumorigenicity, latency, growth rate, apoptosis, necrosis, proliferation, hypoxia, vascular profile, intravasation and metastasis in MARY-X treated with angiogenic inhibitors versus controls. This approach will dissect out the angiogenic from intravasation phenotypes and will also help to elucidate the mechanism of intravasation which is poorly understood. In this context, there are two possible explanations: either tumor cells gain access to the lymphatic and/or blood vessel capillaries by invasion of pre-existing vessels or newly-forming angiogenic vessels in the process of forming tubes also form around invading tumor cells. These alternate possibilities have never been tested experimentally. If the latter mechanism is the mechanism, then inhibiting angiogenesis will inhibit intravasation; if the former mechanism is the true mechanism, inhibiting angiogenesis can still inhibit intravasation if intravasation occurred only in angiogenic blood vessels or if the step of intravasation were dependent on the tumor cell's well being (being well-nourished and well-oxygenated from angiogenesis). On the other hand if intravasation occurs unimpeded by angiogenic inhibitors on board, this will provide evidence that intravasation and angiogenesis are independent phenomena. Other tumoral features such as proliferation, necrosis, hypoxia and apoptosis can also be affected by the inhibition of angiogenesis and can influence the degree of intravasation. The vascular profile of the tumor can also be affected: the number of angiogenic vessels would be predicted to decrease with angiogenic inhibitors on board and therefore the relative numbers of lymphatics and non-angiogenic blood vessels would increase. If the latter vessels were primarily the targets of intravasation, intravasation might increase in the face of angiogenic inhibitors. One can then study the organization of growing MARY-X in situ for tumor cell proliferation, apoptosis, hypoxia and necrosis relative to the specific types of vascular elements present in the face of angiogenic inhibitors versus controls.

Use of Angiogenic inhibitors. One can employ one of several different angiogenic inhibitors known in the art including thalidomide, INP-470, angiostatin and endostatin in varying doses injected intraperitoneally or subcutaneously. Effects on tumorigenicity, latency and growth rate of MARY-X can be observed and compared to the effects on the non-inflammatory xenografts, MDA-MB-231 and MDA-MB-468. One can use a spectrum of different inhibitors because some may be more potent than others in MARY-X and this will allow the identification of the agent which generates the most dramatic anti-angiogenic effects. Since their mechanisms of action (some are dual; others are single) of these inhibitors are all different, the use of each inhibitor is an alternate and subsequent strategy. MARY-X may grow, fail to grow, regress, intravasate more, intravasate less, etc. with one or more of these inhibitors. Empirically one can start with doses and a dose schedule of: angiostatin (0.6 $\mu$g/g daily), endostatin (20 $\mu$g/g daily) for 2–4 weeks; thalidomide and/or TNP-470 (200 $\mu$g/g –300 $\mu$g/g for 4 weeks) after implanting 1 mm$^3$ fragments of the xenografts. Since the action of the angiogenesis inhibitors may not be angiostatic specific (they may cause tumor regression by a non-angiostatic mechanism) it is important to measure the vascular profile of treated MARY-X and the non-inflammatory xenografts.

Characterization of tumoral parameters of MARY-X treated with angiogenic inhibitors. Tumoral parameters which can be measured include proliferation, apoptosis, hypoxia, necrosis, intravasation relative to vascular elements and metastasis.

Apoptosis Assay: Apoptosis can be detected by labeling the 3'OH ends of DNA utilizing digoxigenin-nucleotide incorporation by terminal deoxynucleotidyltransferase. Antidigoxigenin antibodies and immunoperoxidase staining can be utilized with the ApopTag detection system (Oncor, Gathersburg, Md.). In brief, sections can be taken from formalin-fixed paraffin-embedded xenografts, deparaffinized with xylene and ethanol, rinsed with PBS and finally incubated in a reaction mixture containing terminal transferase and digoxigenin-dUTP at 37° C. for 1 h. The specimens can then be washed followed by the addition of anti-digoxigenin antibodies coupled to horse radish peroxidase and the cells can be incubated for 30 min at room temperature. Following rising with PBS, diaminobenzidine tetrachloride (DAKO, Carpenteria, Calif.) can be added and the sections incubated for 10 min. Brown nuclear staining can be interpreted as positive. All sections can be coded and scored blindly by two observers using a standard light microscope. At least 1000 malignant cells can be counted, in high-powered fields spread randomly throughout the section, and the percentage of positively stained nuclei will be expressed as the apoptotic index (AI). The relationship of apoptosis to blood vessels can then be determined.

Necrosis measurements: Necrosis can be measured by standard hematoxylin and eosin staining and estimate of the overall percentage of necrosis will be determined. The relationship to blood vessels can then be determined.

Hypoxia measurements. The principle that pimonidazole binds to thiol-containing proteins specifically in hypoxic cells can be exploited by immunohistochemical detection of pimonidazole using a mouse monoclonal antibody in tissue sections of the MARY-X xenografts versus the non-inflammatory xenografts grown in mice receiving intraperitoneal injections of pimonidazole hydrochloride (0.5 g/m$^2$) followed by extirpation of the xenografts 24 hours later and immunohistochemical analysis. Pimonidazole immunoreactivity can be present as cytoplasmic staining. The number of hypoxic cells (positively stained) can be expressed as a percentage of total. Dilutions of primary and secondary antibody can be titrated to neutralize the effects of murine immunoglobulins so that only the hypoxic areas stain and not the necrotic areas. The relationship of hypoxic regions to blood vessels can then be determined.

Proliferation: Proliferation can be measured by S phase determination on flow cytometry and measurements of Ki-67 nuclear immunoreactivity. For Ki-67 antigen, formalin-fixed paraffin sections of the xenografts can be subjected to microwave-processing. Sections will be incubated with primary antibody (1/100 Ki-67) as is known in the art. Sheep anti-mouse IgG can be used as secondary antibody at 1/200 dilutions. Antigen binding sites can then be revealed by incubating with peroxidase polymerizing diaminobenzidine (DAB), producing brownish-black staining at sites of antigen presence. Nuclei of cells expressing Ki-67 will stain positive. For Ki-67, the number of positive nuclei will be expressed as a percentage of total nuclei. The areas of increased Ki-67 immunoreactivity can be mapped with respect to blood vessels (new or old), areas of hypoxia or necrosis, areas of intravasation, etc. The effects of angiogenic inhibitors can be determined. The effects on MARY-X can then be compared to the non-inflammatory xenografts.

Characterization of the vascular profile of MARY-X treated with angiogenic inhibitors. The vascular immunocytochermistry pattern distinguishing angiogenic blood vessels, old blood vessels and lymphatics as mentioned previously can be studied. Measurement of vascular porosity/permeability with Evan's blue extravasation can also be studied as described above.

Statistical Analysis. Standard tests of statistical significance can be conducted. These can include Chi-Square, the Cochran-Mantel-Haenszel modified Chi-Square, and a two-tailed t-test.

Methods for Identifying Molecules Associated with the Inflammatory Phenotype

The invention disclosed herein allows a variety of molecular comparison to identify those genes that are uniquely expressed (or not expressed) by inflammatory carcinoma to see whether they trigger separate or common downstream events linked to angiogenesis and/or intravasation. Findings of increased E-cadherin transcription but not amplification or rearrangement suggests cis/trans promoter interactions by upstream genes. Because inflammatory carcinoma is such a unique disease, unique upstream genes regulate the expression of those effector molecules which cause its phenotype. Therefore one can use methods known in the art to identify the higher level genes which regulate the inflammatory phenotype of intravasation (lymphovascular invasion). In identifying the upstream genes that are uniquely expressed (or not expressed) by inflammatory carcinoma, one can also investigate whether they trigger separate or common downstream events linked to angiogenesis and/or intravasation.

Specifically, the xenograft model disclosed herein allows for the inauguration of a variety of different approaches to identify the genetic and phenotypic basis of inflammatory carcinoma and the important rate-limiting step of intravasation. As discussed in detail below, preferably these approaches involve a comparison of MARY-X to the non-inflammatory 231 and 468 xenografts. For example, the invention provides a large number of methods for identifying one or more molecules whose expression is modulated in inflammatory breast cancer by determining the level of expression of at least one molecule in the human inflammatory breast cancer xenograft; and comparing this to the level of expression of the same molecule in a cell having characteristics which are distinct from the human inflammatory breast cancer xenograft. In preferred embodiments of this invention, the level of expression of the molecule of the inflammatory breast cancer xenograft is determined by a method selected from the group consisting of: Northern Blotting, Southern Blotting, Western Blotting and polymerase chain reaction.

One exemplary approach involves Northern and Western blot comparisons of MARY-X to the noninflammatory 231 and 468 xenografts are as disclosed herein. As the class of molecules which mediate the inflammatory phenotype are likely to be either molecules of the adhesion family (either on tumor cells or endothelial cells), angiogenic growth factors (elaborated by tumor cells) or proteolytic enzymes elaborated by tumor cells which facilitate intravasation we can initially conduct a comparative screen of the major effector molecules previously implicated- in the above mentioned processes.

Yet another approach is a mRNA shotgun comparison using microarray secretory libraries. Specifically, the mechanism of the inflammatory carcinoma phenotype likely involves effector molecules that mediate the interaction of breast carcinoma cells with endothelial cells and these molecules are likely to belong to the "secretory class" of molecules. The "secretory class" of molecules include all those with signal peptide sequences and includes cell surface proteins (receptors) and secreted molecules. These delineating assumptions allows one to significantly decrease the candidate molecule pool to 5–10% of the total molecules expressed by MARY-X. One can then utilize secretory microarray gene chips containing both cloned human secretory molecules and SSTs (secreted sequence tags) which are constructed from a signal trap selection strategy (see e.g. Honjo et al., Science 268: 600–603, (1993)). A murine secretory microarray chip is also available. Therefore, one can carry out a mRNA shotgun comparison of MARY-X with the 231 and 468 xenografts to look for signals that are present or significantly increased in MARY-X but absent or reduced in the non-inflammatory xenografts.

Yet another approach is an in vivo subtraction strategy using expanded human recombinant phage libraries. Such an approach comprises an in vivo subtraction strategy using, expanded human recombinant phage libraries injected into the tail vein of mice harboring 231, 468 and MARY-X with the anticipated recovery of Ig-phages that selectively bind to MARY-X. The power of the immune system stems from its ability to diversify antigen receptors. In the case of B cells, DNA rearrangement. combinatory events (i.e., random pairing of heavy and light chains) and specialized "diversity-producing" mechanisms (e.g., N and P nucleotide additions) produces an antibody repertoire of $10^6$ unique molecules. A similar repertoire complexity can be obtained with Ig-phage libraries. Diversity in such libraries can be achieved by the production of semi-synthetic Ig-phage libraries (see e.g. Griffiths et al., EMBO J. 13: 3245–3260 (1994). Semisynthetic phage libraries are created by introducing mutations via error prone polymerase, by reshuffling heavy and light chains, or by randomly mutating the heavy chain complementarity determining region 3 (CDR3) of the Ag binding site. Such manipulation can produce library sizes close to $10^{13}$. Recent studies have demonstrated the feasibility of injecting a phage library into the tail veins of mice in which selected clones immunolocalize and are able to be recovered from human breast carcinoma Xenografts (see e.g. Arap et al. Science 279: 377–380 (1998)). This approach is especially suited for our inflammatory xenograft model because MARY-X exhibits florid invasion lymphovascular spaces and hence the injected Ig-phage clones would have easy access to both the tumor's vasculature as well as the tumor itself. An in vivo subtraction strategy in rice harboring, 231. 468 and MARY-X preferable because it will eliminate those phages which bind either non-specifically to tumor vasculature or to generally present breast carcinoma surface antigens or receptors that have nothing to do with the inflammatory carcinoma phenotype.

Following tail vein injection. MARY-X can be extirpated and bound phages recovered, propagated and re-injected for subsequent rounds of in vivo selection with the ultimate recovery of Ig-phages that selectively bind to surface determinants on either the breast carcinoma cells or the endothelial cells within MARY-X that specifically mediate its inflammatory phenotype. The cloned phages will be used to identify the surface molecules involved.

The approaches enumerated herein will identify several candidate molecules. Realizing that identified molecules may be tumoral or endothelial, one benefit of the human xenograft model is that one can distinguish them because tumoral molecules would be human while the endothelial molecules will be murine. One can transduce any human molecule which shows promise into the 231 and 468 lines to see if we can induce the inflammatory phenotype. Specifically, a nucleic acid (e.g., cDNA or genomic DNA) encoding a candidate molecule may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

Conversely, through an antisense technology approach one can knock out a molecule of interest in MARY-X to see if this abolishes its inflammatory phenotype. Antisense technology entails the administration of exogenous oligonucleotides which bind to a target polynucleotide located within the cells. The term "antisense" refers to the fact that such oligonucleotides are complementary to their intracellular targets, e.g., E-cadherin. See for example, Jack Cohen, OLIGODEOXYNUCLEOTIDES, Antisense Inhibitors of Gene Expression, CRC Press, 1989; and Synthesis 1:1–5 (1988). Antisense oligonucleotides of the present invention include derivatives such as S-oligonucleotides (phosphorothioate derivatives or S-oligos, see, Jack Cohen, supra) which exhibit enhanced cancer cell growth modulatory action.

S-oligos (nucleoside phosphorothioates) are isoelectronic analogs of an oligonucleotide (O-oligo) in which a non-bridging oxygen atom of the phosphate group is replaced by a sulfur atom. The S-oligos of the present invention may be prepared by treatment of the corresponding O-oligos with 3H-1,2-benzodithiol-3-one-1,1-dioxide which is a sulfur transfer reagent. See Iyer, R. P. et al, J. Org. Chem. 55:4693–4698 (1990); and Iyer, R. P. et al., J. Am. Chem. Soc. 112:1253–1254 (1990), the disclosures of which are fully incorporated by reference herein.

A variety of specific approaches can be constructed utilizing the methods disclosed herein. For example, one can conduct an differential display analysis between the MARY-X "shake" (which has essentially eliminated the murine component), MARY (the "spheroid" cell line derived from MARY-X), the non-inflammatory breast carcinoma xenografts and cell lines (MDA-MB-231 and MDA-MB-468) and normal human mammary epithelial cells (HMEC). One can initially focus exclusively on all or none differentially expressed transcripts between the MARYs and the non-MARYs in order to identify high level regulatory genes (in the class of oncogenes or tumor suppressor genes) as opposed to downstream genes in this approach. Oncogenes (by rearrangement) and suppressor genes (by deletion) will manifest by all or none differential expression of these transcripts, internal consistency between MARY-X and MARY will provide evidence that these transcripts represent genetic alterations (either amplification, rearrangement or loss), whereas divergence between MARY-X and MARY will provide evidence that these transcripts are epigenetically rather than genetically regulated and likely not as important from the standpoint of possible oncogenes or suppressor genes. All transcripts identified by differential display can be confirmed by Northern blot of the respective cell lines/xenografts. Confirmed transcripts can be excised from the differential display gel, reamplified, cloned and sequenced. Sequences can be compared with known sequences on the BLASTN, expressed sequence tag (dbEST) and The Institute for Human Genome Research (TIGR) databases. At the same one can analyze the expression of selected transcripts in actual cases of human inflammatory and non-inflammatory breast cancer as disclosed in our MUC1 and E-cadherin observations provided herein. One can conduct this comparison by both in situ hybridization and RT-PCR experiments in a bank of microdissected fresh frozen cases. One can look for clones that are expressed (or not expressed) in the vast majority of inflammatory carcinoma cases but not expressed (or expressed) in the non-inflammatory cases. The presence of E-cadherin transcripts will be an internal control for the fidelity of the differential display. Any identified sequence which suggests either an oncogene or suppressor gene or high level transcription factor can be obtained full length via art accepted methods and subjected to functional studies of intravasation and angiogenesis induction.

Illustrative examples of specific and augmentary procedures for identifying molecules associated with the inflammatory cancer phenotype are described below.

Differential Display. Differential display can be conducted with a third generation RNAimage Kit (GenHUnter Corporation, Nashville, Tenn.) using three one-based-anchored oligo-dT primers to subdivide the mRNA population. With built-in restriction sites at the 5' ends of both anchored and arbitrary 13mers, the longer primer pairs produce highly selective and reproducible cDNA patterns. This ensures that differentially expressed genes are more readily identified, cloned and manipulated.

Laser capture microdissection. One can collect fresh frozen cases of inflammatory carcinoma and successfully microdissect the tumor plugs of lymphovascular invasion. One can also retrieved archived cases of several hundred inflammatory carcinomas embedded in paraffin. The availability of such tissue will allow one to determine if the sequences (presence or absence) identified by differential display of MARY-X are also exhibited by actual cases of human inflammatory carcinoma.

Functional characterization of isolated cDNAs from differential display. The role of the cDNAs can be determined by first isolating and characterizing their full length cDNA equivalent with RACE and ultimately determining the functional activity of these cDNAs in either MARY-X (for transcripts entirely absent in MARY-X) or the non-inflammatory lines MDA-MB-231 or MDA-MB-468 (for transcripts exclusively present in MARY-X). One can initially continue the sequencing strategy described herein and perform Northern blot hybridization analyses in MARY-X and the MDA-MB-231 or MDA-MB-468. Once full length cDNAs are isolated, one can use RNase protection assays to determine the fidelity of these cDNAs to ensure that there are no mutations or alterations in these cDNAs resulting from the PCR and RACE procedures. The sequences can then be submitted to NCBI to determine the homology of these cDNAs at the nucleotide and protein levels. The protein sequence will allows one to consider hypotheses on the possible function and activity of the protein as well as generate antibodies to either the purified proteins (proteins could be generated by cDNAs in vitro transcribed and translated or bacterial expressed proteins) or synthetic polypeptides. MARY-X and the MDA-MB-231 or MDA-MB-468 cells can be analyzed at the RNA and protein levels to determine expression levels, cell location, and tissue distribution. MARY-X and the MDA-MB-231 or MDA-MB-468 cells can be transfected with expression vectors containing these cDNAs in a sense or antisense orientation to determine their effects. Specifically the effects of these cDNAs on the production or inhibition of angiogenic factors and the induction/inhibition of angiogenesis can be assayed in vitro and in mice respectively. Similarly the effects of these cDNAs on the production or inhibition of intravasation-related molecules such as E-cadherin (and possibly MUC-1) can be assayed in vitro and the induction/inhibition of intravasation will be assayed in mice. These studies allow one to determine the cDNA(s)' functional activity and see whether the downstream events they trigger are related to angiogenesis or intravasation or both. If pleoitropism is demonstrated, this provides evidence that the angiogenic and intravasation phenotypes are on the basis of the same upstream genotype and therefore related. On the other hand if intravasation and its related gene products and angiogenesis and its related effector molecules are separately regulated, this provides evidence that these two phenotypes are distinct from the cancer cell's viewpoint.

Methods for Characterizing the Functional Role of Molecules Associated with the Inflammatory Phenotype The invention described herein allow both in vitro and in vivo functional studies to examine whether molecules associated with an inflammatory xenograft cause lymphovascular invasion and if this is linked to angiogenesis (MUC1 and E-cadherin are provided as illustrative examples). In this context a variety of art accepted methods can be employed to characterize molecules associated with the inflammatory phenotype including those disclosed below.

Adhesion (attachment) assays and neutralizing effects of antibodies. The invention disclosed herein allows one to evaluate the cell-cell and cell-surface adhesion of MARY with different substrates and different monolayers and to determine whether a specific type of adhesion is preferentially mediated by, for example, MUC1 and/or E-cadherin. For example one can determine whether MUC1 preferentially mediates the binding of MARY to endothelial cells and whether E-cadherin preferentially mediates the adhesion of MARY to epithelial cells. In this context, MARY and some of the non-inflammatory breast carcinoma cell lines, e.g. MDA-MB-231, etc. can be labelled with $[^{125}I]$ 5-iodo-2'-deoxyuridine (IUdR) and a number of different attachment assays. Attachment to an uncoated plastic surface (tissue culture dish), purified matrix components (types I and IV collagens, fibronectin, laminin etc.), Humatrix (an extracted human myoepithelial matrix), a monolayer of human umbilical vein endothelial cells (HUVECs), and a monolayer of human mammary epithelial cells (HMECs) can be carried out over 1–4 hr or longer. The specific effects of neutralizing antibodies to MUC1 and E-cadherin can be observed in each of these attachment assays to determine which particular adhesion protein functions in which specific type of cell-cell and cell-surface interactions. The results with MARY can be compared to non-inflammatory breast carcinoma lines which expresses low/absent levels of MUC1 and/or E-cadherin.

As disclosed herein, both anti-E-cadherin antibodies and absent $Ca^{+2}$ produce disadherence of the spheroids of MARY-X (FIG. 9), observations which provide evidence that E-cadherin is functioning in the maintenance of the tumor embolus of lymphovascular invasion.

MUC-1 on MARY-X does not contain sialyl Lewis X and sialyl Lewis A glycoconjugates raising the possibility that MUC-1 does not mediate tumor cell-endothelial E-selectin adhesion or that MUC-1 contains other epitopes (ligands) for E-selectin. To address this, an adhesion assay for MARY can be carried out in plates coated with purified E-selectin or a chimeric E-selectin protein (purified previously by affinity chromatography). If binding occurs, this provides evidence that MUC-1 contains some other epitopes other than sialyl Lewis X and A that bind E-selectin or that some other molecule expressed by MARY-X was binding E-selectin. If no binding occurs this provides evidence that E-selectin was not mediating MARY-X's adhesion to endothelial cells during intravasation and that some other endothelial adhesion molecule was involved. In this context, one can pretreat HUVECs with cytokines thought to be involved in angiogenesis such as TNF-α and IL-1-α which upregulate E-selectin and perhaps other endothelial adhesion molecules during angiogenesis. One can then test the adhesion of MARY to cytokine treated HUVECs. If adhesion increases this provides evidence that some other adhesion molecule (other than E-selectin) presumably upregulated during angiogenesis was mediating the attachment. On the other hand if adhesion does not increase this provides evidence that whatever endothelial adhesion molecules were mediating the interactions of MARY-X during intravasation these probably were unrelated to angiogenesis. If the latter observations are made, this provides evidence that intravasation and angiogenesis are either unrelated or inversely related.

Adhesion assays and effects of pharmacological manipulations. Both the monolayer feeder layer (endothelial or epithelial cells) and the target layer (MARY or 231, for example) can be pretreated with specific agents designed to perturbate adhesion and shed light on specific molecular interactions. As has been mentioned, the HUVEC monolayer can be pretreated with IL-1α and/or TNF-α to upregulate E selectin and then whether adhesion of MARY is enhanced via a MUC1 mechanism can be investigated. If these treatments resulted in increased attachment, this would support the role of MUC1 in mediating heterotypic adhesion (between carcinoma cells and endothelial cells). Alternatively, one can reduce the levels of MUC1 on either MARY or the HMEC monolayer with either sodium butyrate (NaB) or ubenimex treatment (two known inhibitors of MUC1 transcription) or with antisense MUC1 oligonucleotides and the effects on adhesion in this latter setting can be examined. If these treatments result in decreased adhesion, this would support the importance of MUC1 in mediating homotypic interactions; on the other hand if adhesion is increased, it would support the possible antagonism of MUC 1/E-cadherin as has been suggested. The effects of neutralizing antibodies mentioned previously can be examined in the context of these pharmacological pretreatments as well.

Cadherin-catenin complex phosphorylation and effects of tyrosine kinase inhibitors. Since tyrosine phosphorylation of the cadherin-catenin complex and dephosphorylation of β-catenin are thought to either decrease or increase cadherin-mediated adhesion, the expression and tyrosine phosphorylation of the cadherin-catenin complex can be examined in MARY-X and MARY. The components of the complex can be measured by Western blot with the appropriate antibodies in both untreated MARY and MARY-X. The effects of NaB and/or ubenimex treatment on the cadherin-catenin complex can be measured. Cadherin-catenin complex phosphorylation can be determined with immunoprecipitation studies with the same antibodies followed by Western blot of the precipitans with an antiphosphotyrosine antibody. The effects of the previous drugs on phosphorylation of this complex can be determined along with effects of tyrosine kinase inhibitors (herbimycin and genistein). The effects of NaB/ubenimex on adhesion both in the presence/absence of tyrosine kinase inhibitors can be studied. One can determine whether phosphorylation of the cadherin-catenin complex contributes to the adhesive properties of inflammatory carcinoma and the step of intravasation and its relationship to angiogenesis.

Transfections. Using the mammalian expression vector, pCMV-Poly1 and -Poly2 containing the human MUC1 and the human E-cadherin genes in both sense and antisense orientations respectively, stable transfections can be carried out in MARY and in several of the non-inflammatory breast carcinoma lines. Some of the lines can be double transfected with both MUC1 and E-cadherin using pSV2neo and pSV2hygro selection. Transfectants containing all combinations of sense and antisense constructs can be produced. The effects on adhesion can be determined in in vitro attachment assays; the effects of neutralizing antibodies likewise examined. The effects of the antisense constructs to perturbate the inflammatory phenotype exhibited by MARY/MARY-X can be determined in nudes/Scids. Alternately, the effects of sense constructs in inducing the inflammatory phenotype in non-inflammatory cell lines can be investigated. Both the transfected MARY-X and the non-inflammatory xenografts can be subjected to an in-depth analysis of their vasculature and tumor parameters as enumerated above.

Analyses of the Role of Muc1 and E-Cadherin in the Inflammatory Phenotype

The studies disclosed herein comparing MARY-X with the non-inflammatory xenografts, 231 and 468, demonstrate that ER and PR negativity and p53 and EGFR positivity could not be the cause of the inflammatory carcinoma phenotype because these markers are exhibited by both the inflammatory as well as the non-inflammatory xenografts. Furthermore Her-2/neu amplification can not be the cause of the inflammatory carcinoma phenotype because MARY-X is a clonal outgrowth of an Her-2/neu negative tumor cell population which manifests florid lymphovascular invasion. These comparisons indicate that none of the "aggressive biomarkers" of breast cancer mediate the inflammatory carcinoma phenotype. Because this phenotype is characterized by homotypic clumps of tumor cells stuffed in vascular spaces, one reasoned that the mechanism likely involved adhesion molecules on tumor cells and/or angiogenic factors and/or proteolytic enzymes elaborated by tumor cells which enable intravasation. Our studies compared MARY-X with non-inflammatory breast carcinoma xenografts, MB-231 and -468 with respect to representative adhesion molecules, angiogenic factors and proteolytic enzymes (Table 1).

| Adhesion molecules | Angiogenic factors | Proteolytic enzymes |
| --- | --- | --- |
| Integrin family | bFGF | cathepsin D |
| Immunoglobulin super-family | aFGF | cathepsin B |
| The selectin family | TGF-α | stromelysin-1 |
| DCC | TGF-β | u-PA |
| E-cadherin | VEGF | t-PA |
| CD44 | Angiogenin | plasminogen |
| Syndecan | HGF | matrilysin |
| PSGL-1 | Platelet-derived ECGF | 72 kDa gelatinase A |
| Other molecules, e.g. MUC1 | Heparin-binding ECGF | 92 kDa gelatinase B |

Figure 6:
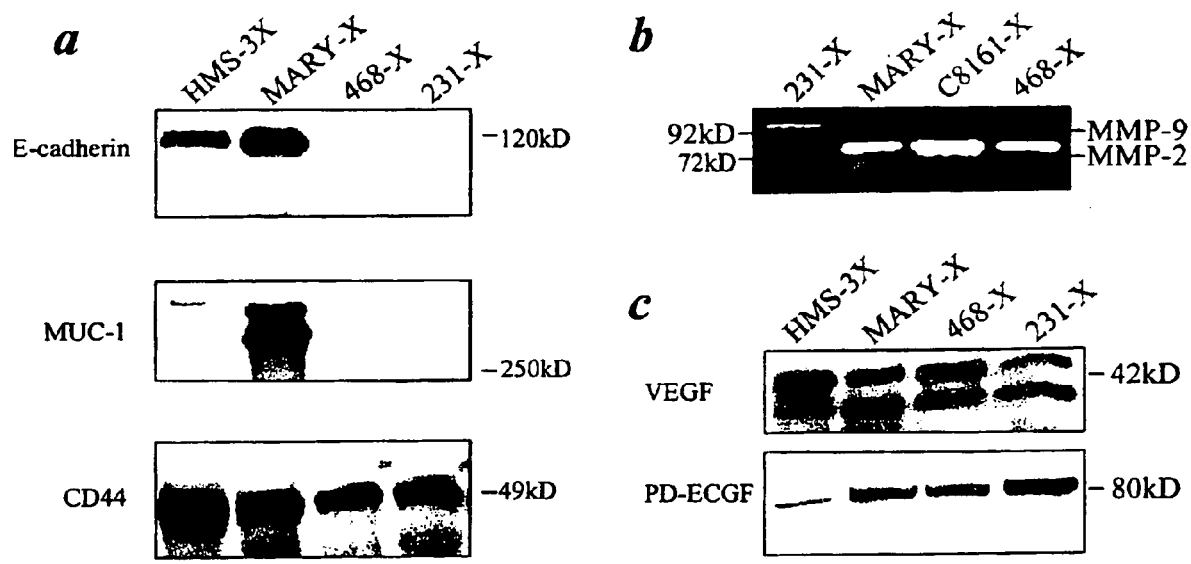
FIG. 6: A representative comparison between MARY-X and different non-inflammatory xenografts with respect to a, adhesion, b, protease and C, angiogenic molecules reveals a, overexpression of E-cadherin and MUC-1 but not CD44; b, no increase in the 72 kD and 92 kD matrix metalloproteinases; c, no increase in angiogenic factors including VEGF and PD-ECGF. 231-X and 468-X represent xenografts of the human breast carcinoma lines, MDA-MB-231 and MDA-MB-468 respectively; C8161-X is the xenograft of the C8161 human melanoma line; HMS-3X is a human myoepithelial xenograft.
Figure 7:
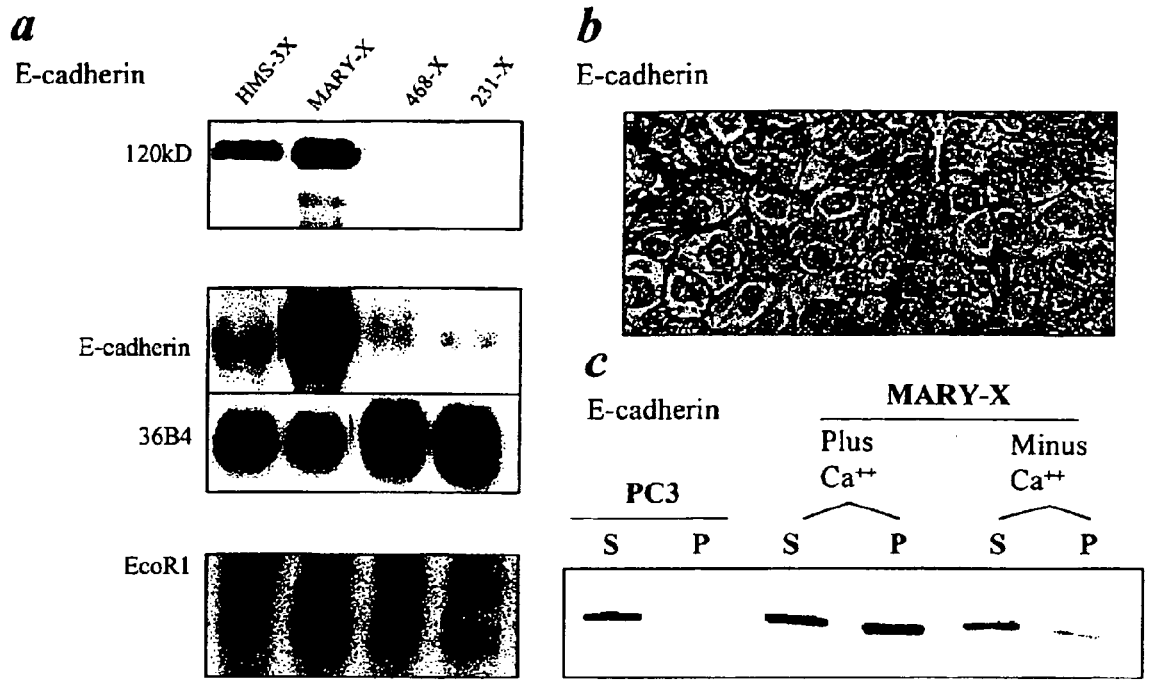
FIG. 7: a, Western, Northern and Southern blot of E-cadherin in MARY-X compared to the non-inflammatory xenografts mentioned in FIG. 6. Overexpression of E-cadherin is due to increased transcription. The absence of the larger band and the increased prominence of the smaller bands only in MARY-X suggest an EcoRI RFLP in one allele of MARY-X. b, prominent E-cadherin membrane immunoreactivity was present in MARY-X, human cases of inflammatory breast carcinoma and in foci of lymphovascular invasion of non-inflammatory breast carcinoma cases. c, Western blot of the triton X-100 solubility assay performed in the presence and absence of $Ca^{++}$: In MARY-X with the prolonged (30 minutes) $Ca^{++}$ extraction, most of the E-cadherin is still in the particulate (P) fraction; in the absence of $Ca^{++}$, however, E-cadherin is exclusively in the soluble (S) fraction, indicative of its dissociation from the cytoskeleton: in the PC-3 which lacks α-catenin, E-cadherin is exclusively in the soluble (S) fraction even in the presence of $Ca^{++}$ because it is unbound from the cytoskeleton.

There were no essential differences in angiogenic factors or proteases between MARY-X and the non-inflammatory xenografts (FIG. 6). The protease result was surprising since elevated 92 kDa MMP had been observed in cell lines with increased intravasation in the chick allantoic membrane model. Among the adhesion molecules, however, there was striking overexpression (10–20 fold) of MUC1 and interestingly and surprisingly E-cadherin (FIGS. 6,7). Other adhesion molecules showed no appreciable differences.

The observation that MUC1 and E-cadherin (FIGS. 6,7) are 10–20 fold overexpressed in MARY-X (including the enriched MARY-X shake which is 99% human tumor cell-enriched) compared to the non-inflammatory breast carcinoma xenografts and cell lines was both surprising and unexpected, especially in the case of E-cadherin which the art teaches is usually lost or rendered non-functional in many carcinomas contributing therefore to the non-adhesive state rather than the adhesive state. E-cadherin is part of a membrane complex with α-catenin and β-catenin which form the adherens plaque and which mediates adhesion to actin in the cytoskeleton. Disruption of any point of this axis causes non-adhesion rather than adhesion. E-cadherin which has lost either extracellular domains or cytoplasmic domains, the absence of α-catenin or abnormal β-catenin, or the absence of this complex binding to the actin cytoskeleton all leads to the non-adhesive state. The E-cadherin adhesive state is also $Ca^{+2}$ dependent. Therefore any study of whether MUC1 and E-cadherin expression, in fact, uniquely cause or at least contribute to the inflammatory phenotype of lymphovascular invasion must first begin with a demonstration that they are proteins that are not only overexpressed but which actually contribute to the functional state of adhesion in inflammatory carcinoma. For example there is a prostate cancer cell line, the PC3 which overexpresses E-cadherin but which lacks α-catenin. Its E-cadherin is cytoplasmic rather than membrane and is non-functional and non-adhesive. In MARY-X we demonstrate that the overexpression of E-cadherin is due to increased E-cadherin transcription rather than a gene dosage effect (FIG. 7). We have also demonstrated that MUC-1 overexpression is due to both a gene dosage effect (the gene is amplified) as well as a post-translational effect (possibly altered glycosylation contributing to protein stability).

Figure 8:
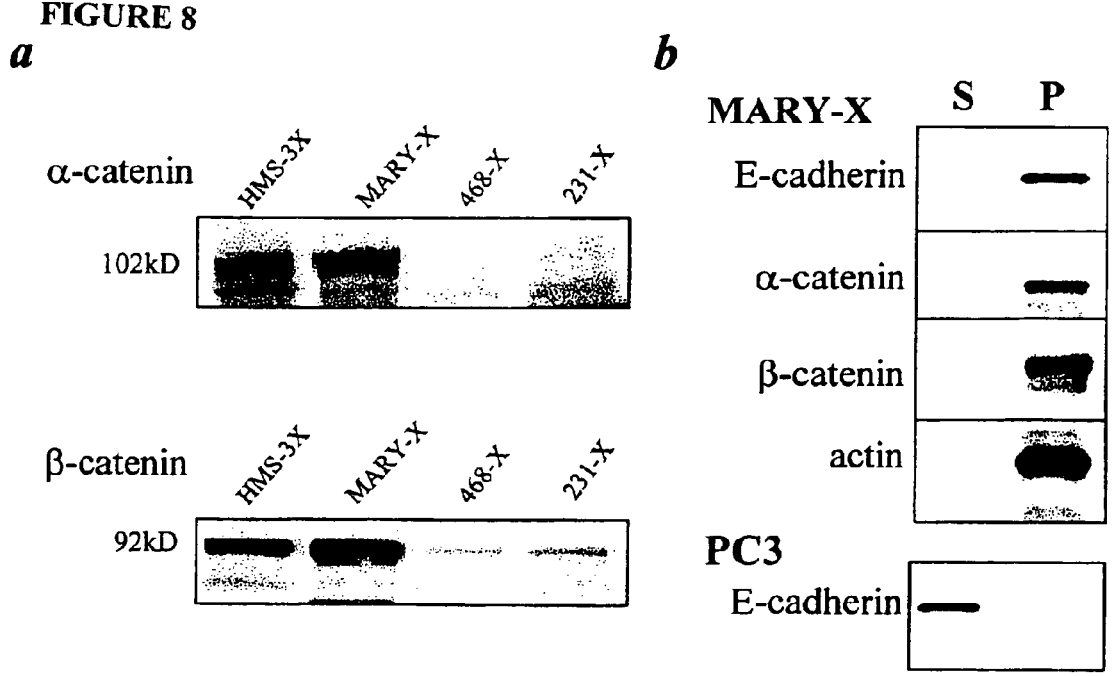
FIG. 8: Intactness and overexpression of the E-cadherin axis including the catenin plaque proteins in MARY-X compared to the non-inflammatory xenografts mentioned in FIG. 6 and FIG. 7. a, Western blot of α-catenin and β-catenin; b, Western blot of the triton-X solubility assay performed in the presence of $Ca^{++}$ in MARY-X compared to the PC3. The entire E-cadherin axis including the plaque proteins, α-catenin and β-catenin, appears in the particulate fraction along with cytoskeletal actin suggesting that the E-cadherin axis is intact and functionally adhesive in MARY-X; in contrast in PC-3, which lacks α-catenin, the E-cadherin is exclusively in the soluble fraction, its axis is not intact and it is non-adhesive. c, immunoprecipitation with anti-E-cadherin followed by antiphosphotyrosine Western blot analysis (upper blot, left). The band at 92 kD is β-catenin and is only weakly phosphorylated. Other bands represent other phosphorylated proteins of the E-cadherin complex. Immunoprecipitation with anti-β-catenin followed by antiphosphotyrosine Western blot analysis (upper blot, right) gave similar results. Western blot analysis for β-catenin on the respective anti-E-cadherin (lower blot, left) and anti-β-catenin (lower blot, right) precipitans confirmed its identity. Although the β-catenin immunoprecipitation precipitated more β-catenin than the E-cadherin immunoprecipitation, the ratio of the β-catenin precipitated by the β-catenin method compared to the E-cadherin method was no different in MARY-X, HMS-3X or HMEC. Western blot of β-catenin on whole tumoral extracts (FIG. 8a) was used to normalize and compare the degree of tyrosine phosphorylation of β-catenin on MARY-X with HMS-3X and HMEC.

The E-cadherin protein is fully intact in MARY-X (full 120 kD size) (FIG. 6) and therefore has not lost either extracellular or cytoplasmic domains. Furthermore both α-catenin and β-catenin are present and in fact also overexpressed in MARY-X (FIG. 8). Triton-X extraction followed by subcellular fractionation by precipitating the membrane fractions at 10,000 g reveals that E-cadherin, α-catenin and β-catenin are in the membrane (particulate, P) fraction bound to actin in MARY-X whereas E-cadherin is in the cytoplasmic (soluble, S) fraction unbound in the PC3 cell line (FIG. 8). Triton-X extraction of MARY-X performed in the absence of $Ca^{+2}$ disrupts the formation of E-cadherin homophilic aggregates and its binding to the plaque proteins/cytoskeleton and results in increased cytoplasmic (soluble, S) E-cadherin (FIG. 7). As additional support that the increased expression of both MUC-1 and E-cadherin in MARY-X provides a functional increase in adhesive properties and not just a nonspecific accumulation of nonfunctional protein, immunocytochemical studies demonstrated significant membrane immunolocalization. To show the relevance of MARY-X as a model to dissect the molecular basis of lymphovascular invasion for both breast and other cancers we have studied actual cases of human breast cancer and observed increased membrane staining of both MUC1 and E-cadherin in 100% of inflammatory carcinomas (Table 2). Non-inflammatory breast carcinomas showed less staining. However in these non-inflammatory carcinomas, MUC1 and E-cadherin showed increased membrane immunoreactivity in the rare foci of lymphovascular invasion.

TABLE 2

CASES OF HUMAN BREAST CANCER IMMUNOSTAINING

|  | E-cadherin | MUC-1 |
| --- | --- | --- |
| Non-inflammatory carcinoma |  |  |
| Case #1 | ++ | ++ |
| Case #2 | + | +++ |
| Case #3 | − | + |
| Case #4 | + | + |
| Case #5 | − | + |
| Case #6 | − | − |
| Case #7 | − | ++ |
| Case #8 | − | +++ |
| Case #9 | − | + |
| Case #10 | − | ++ |
| Inflammatory carcinoma |  |  |
| Case #1 | ++++ | ++++ |
| Case #2 | ++++ | ++++ |
| Case #3 | ++++ | ++++ |
| Case #4 | ++++ | ++++ |
| Case #5 | ++++ | ++++ |
| Case #6 | +++ | ++++ |
| Case #7 | ++++ | +++ |
| Case #8 | +++ | +++ |
| Case #9 | +++ | ++++ |
| Case #10 | ++++ | ++++ |

The observation that E-cadherin was 3–5 fold overexpressed in MARY-X compared to the non-inflammatory breast carcinoma xenografts and our myoepithelial xenograft, which represent a surrogate of normal myoepithelial cells, merited close scrutiny as to its significance. As noted above, E-cadherin expression generally has been thought to be either lost in malignant progression or rendered non-functional through structural changes in the E-cadherin molecule or associated axis. E-cadherin as an adhesion molecule is found in normal cells as part of a membrane complex with α-catenin and β-catenin which form the adherens plaque. The modular architecture of the E-cadherin molecule consists of five repeats in the extracellular domain, a single transmembrane region and a single intracellular domain linked to the actin filaments of the cytoskeleton via α and β-catenins (Alattia et al., FEBS Letters 417, 405–408 (1997)). The specific homophilic-binding capacity of the extracellular domain of E-cadherin translates into stable cell adhesion. The extracellular domain of E-cadherin forms parallel dimers that possess intrinsic homophilic-binding activity as antiparallel dimers in the outermost domain termed EC1. E-cadherin through the catenins binds to actin in the cytoskeleton.

Disruption of any part of this axis causes non-adhesion rather than adhesion. E-cadherin which has lost either extracellular domains or cytoplasmic domains, the absence of α-catenin or abnormally phosphorylated β-catenin and the absence of this complex's binding to the actin cytoskeleton all leads to the non-adhesive state. The E-cadherin adhesive state is also $Ca^{++}$ dependent; absence of $Ca^{++}$ disrupts the homodimeric interactions between repeat motifs within the EC1 domains of the E-cadherin molecule and in addition, is probably chaotropic for the intracellular interactions with the catenins and the actin cytoskeleton (see e.g. Troxell et al., Am. J. Physiol. 276, C404–C418 (1999); Koch et al., Biochemistry 36, 7697–7705 (1997)). Some cancers may overexpress a structurally defective E-cadherin molecule or exhibit structural disruption of the E-cadherin axis. For example in the PC-3 prostatic carcinoma line, there is overexpression of E-cadherin but a complete absence of α-catenin (see e.g. Kaighn et al., Invest. Urology 17, 16–23 (1979); Ohnuki et al., Cancer Res. 40, 524–534 (1980)). Since its E-cadherin is not bound through the catenins to cytoskeletal actin, its E-cadherin is found in the cytoplasmic rather than membrane fraction and it is not an adhesion protein. Therefore the demonstration that E-cadherin overexpression in MARY-X was actually contributing to increased adhesion and the inflammatory carcinoma phenotype of lymphovascular invasion would require a number of studies demonstrating that the complete E-cadherin axis was structurally intact as well as amplified.

Figure 8C:
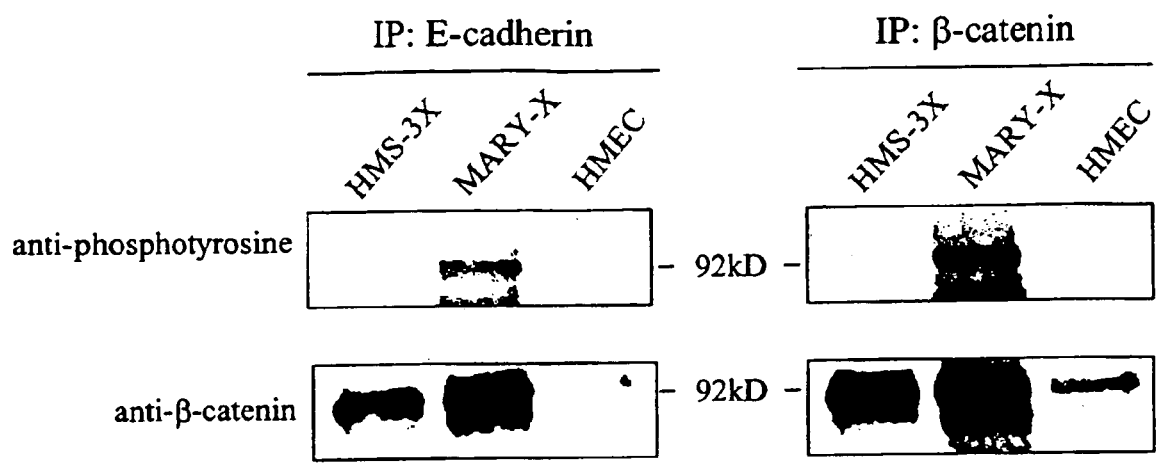

The E-cadherin protein, in fact, was fully intact in MARY-X (full 120 kD size) (FIG. 7a) and therefore had not lost either extracellular or cytoplasmic domains. Triton X-100 solubility extraction of MARY-X in the absence of $Ca^{++}$ resulted in partitioning of the E-cadherin in the soluble fraction whereas triton X-100 extraction in the presence of $Ca^{++}$ demonstrated that the E-cadherin was bound in the particulate (membrane) fraction (FIG. 7c). Not only were both α-catenin and β-catenin present in Mary-X but actually were also overexpressed (~5 fold) (FIG. 8a). Triton X-100 solubility extraction in the presence of $Ca^{++}$ resulted in coprecipitation of E-cadherin, α-catenin, β-catenin and cytoskeletal actin in the particulate (membrane) fraction in MARY-X in contrast to the PC-3 cells where E-cadherin fractionated in the soluble fraction unbound to cytoskeletal actin (FIG. 4b). Immunoprecipitation studies with anti-E-cadherin antibodies followed by a Western blot phosphotyrosine analysis of β-catenin revealed that β-catenin, when normalized for protein, was phosphorylated to the same degree in MARY-X as it was in HMEC and HMS-3X and certainly not overphosphorylated (FIG. 8c). In fact, a second immunoprecipitation strategy employing anti-β-catenin instead of anti-E-cadherin yielded similar results in terms of the degree of β-catenin phosphorylation (FIG. 8c). Although this second immunoprecipitation precipitated more α-catenin than the E-cadherin immunoprecipitation, the ratio of the β-catenin precipitated by the β-catenin method compared to the E-cadherin method was no different in MARY-X, HMS-3X or HMEC (FIG. 8c). Since the last two xenografts/lines represent normal myoepithelial and epithelial cells respectively, cells where β-catenin is thought to function only as a plaque protein and not as a transcription factor, we concluded from this data that in MARY-X, β-catenin functions only as a plaque protein. As has been established, free and abnormally phosphorylated catenins can play a central role in signal transduction and the regulation of gene expression; however we found in MARY-X no evidence of free cytoplasmic β-catenin and no evidence of abnormal phosphorylation.

These collective results are consistent with the entire E-cadherin axis in MARY-X being intact. The following studies show that the above observations relating to structural integrity of the E-cadherin axis are supported by data establishing the functional integrity of the E-cadherin axis.

As illustrated in detail below, embodiments of the invention consists of methods for evaluating at least one agent for treating inflammatory breast cancer by utilizing the xenograft in vitro or in vivo using a immunocompromised host animal inoculated with a human inflammatory breast cancer xenograft, administering at least one agent to said inoculated immunocompromised host animal and evaluating the effects of the agent(s) on the human inflammatory breast cancer xenograft. Optionally, at least two agents are evaluated. An exemplary embodiment of the invention consists of methods for evaluating the potential of an agent, or a combination of agents, for the prevention of lymphovascular invasion of carcinoma cells by utilizing a immunocompromised host animal inoculated with a human inflammatory breast cancer xenograft, administering at least one agent to said inoculated immunocompromised host animal and evaluating the effectiveness of said agent or said combination of agents in the prevention of lymphovascular invasion. In preferable embodiments of these inventions, the immunocompromised host animal is a nude mouse and the human inflammatory breast cancer xenograft is the xenograft designated MARY-X. Optionally the agent evaluated is an antibody or an angiogenic inhibitor.

In Vitro Functional Analyses of the Role of E-Cadherin in the Inflammatory Phenotype The discovery of the overexpression of E-cadherin, in inflammatory carcinoma challenges the conventional dogma concerning E-cadherin loss in tumor progression. Numerous studies have observed that the expression of E-cadherin and related adhesion molecules such as H-cadherin and NCAM are either lost in malignant progression or the normally functioning E-cadherin axis is disrupted (see e.g. Lee, Nature Med. 2, 776–782 (1996); Perl et al., Nature Med. 5, 286–291 (1999)). Loss of epithelial differentiation in carcinomas is thought to be accompanied by higher mobility and invasiveness, which in turn is often a consequence of reduced intercellular adhesion. Although this phenomenon may account for certain aspects of the invasion and metastasis process, the phenomenon has really not been observed or examined in the specific step of intravasation or the formation of tumor emboli within lymphovascular spaces. Furthermore the loss of E-cadherin which has been observed is usually epigenetic rather than genetic. Although loss of heterozygosity and mutation have occasionally been observed, the preponderance of studies indicate reduced gene expression. These studies have all been made in cell lines and human cancers in situ but not in foci of lymphovascular invasion per se and not in inflammatory breast carcinoma. It seems reasonable to reconcile our results with others on the basis of the fact that E-cadherin expression is reversible and can be either up or down regulated depending on the stage of tumor progression. For example in a study of cell lines derived from disseminated cancer cells in bone marrows of patients with solid epithelial tumors, every cell line derived exhibited strong E-cadherin expression (Putz et al., *Cancer Res.* 59, 241–248 (1999)). In the step of intravasation and the formation of the tumor embolus just like in the formation of the blastocyst during preimplantation, E-cadherin expression increases. The disclosure provided herein establishes that not only is E-cadherin overexpressed but that it is part of an intact and amplified axis of adhesion where α-catenin and β-catenin are present and also overexpressed and bound to the actin cytoskeleton. This adhesive network mediates through homophilic and homodimeric interactions of E-cadherin the tumor cell-tumor cell aggregates so characteristic of lymphovascular emboli observed in lymphovascular invasion.

As noted above, the MARY-X "shake" produces the appearance of very tight spheroids in vitro (FIGS. 9a, 9c). The spheroids grew both in suspension as well as attached to monolayers of both human epithelial cells (HMECs) as well as human endothelial cells (HUVECs). In vitro, MARY-X grew as spheroids which disadhered when placed in media containing absent $Ca^{++}$ or anti-E-cadherin antibodies (FIGS. 9b, 9d). This occurred whether the spheroids were grown in suspension or monolayer-attached and the effect was dramatic. The disadherence effect of no $Ca^{++}$ was in evidence after 2 hours and was complete after 6 hours; the disadherence effect of anti-E-cadherin antibodies was in evidence after 6 hours and was complete after 12–24 hours depending on the size of the spheroid. Aggregates of cells derived from non-inflammatory xenografts, cell lines and normal tissues, did not disadhere when placed in media containing E-cadherin antibodies. These non-inflammatory xenografts included the breast MDA-MB-231 which lacks E-cadherin expression and the myoepithelial HMS-3X which expresses normal levels of E-cadherin; the cell lines and tissues included HMECs, HUVECs and normal kidney which express normal levels of E-cadherin. Furthermore with MARY-X, anti-MUC-1, anti-CD44 and control murine IgG1 did not produce disadherence. These findings indicate that specific and amplified homophilic E-cadherin interactions cause the tight spheroid formation observed in the MARY-X "shake" in vitro and suggest that these same E-cadherin homophilic interactions mediate the formation of the tumor embolus within lymphovascular spaces in vivo. Lymphovascular invasion and the inflammatory phenotype is governed then by the gain rather than the loss of E-cadherin function. One can not help but draw analogies between the MARY-X spheroid and its lymphovascular embolic counterpart on one hand and the embryonic blastocyst, the tight compaction of the 8-16 cell embryo from loosely adherent blastomeres which exist prior to implantation. Interestingly the blastocyst is also mediated by increased E-cadherin expression. Increased E-cadherin expression in the embryo causes the formation of the blastocyst and prepares that structure for implantation in the uterus just as increased E-cadherin expression in inflammatory breast carcinoma causes the formation of the lymphovascular embolus and prepares that structure for implantation at its metastatic site.

Both absent $Ca^{++}$ and anti-E-cadherin antibodies disrupt in vitro the tumor spheroids derived from the MARY-X "shake". In a related recent study, the formation of E-cadherin-mediated multicellular aggregates of HSC-3 (human squamous cell carcinoma) survived, proliferated and exhibited anchorage independence and resistance to apoptosis (Kantak et al., *J.Biol.Chem.* 273, 16953–16961 (1998). These multicellular aggregates required high levels of extracellular $Ca^{++}$ and were inhibited with function-perturbing anti-E-cadherin antibody. In that study cadherin-mediated intercellular adhesions generated a compensatory mechanism that promoted anchorage-independent growth and suppressed apoptosis. The multicellular aggregates in that study in essence had gained a survival benefit for the tumor from the gain rather than the loss of E-cadherin function.

In Vivo Functional Analyses of the Role of E-Cadherin in the Inflammatory Phenotype Embodiments of the invention consists of methods for evaluating at least one agent for treating inflammatory breast cancer by utilizing the xenograft in vitro or in vivo using a immunocompromised host animal inoculated with a human inflammatory breast cancer xenograft, administering at least one agent to said inoculated immunocompromised host animal and evaluating the effects of the agent(s) on the human inflammatory breast cancer xenograft. Preferably, the agent targets a molecule identified as being associated with the inflammatory phenotype such as E-cadherin. An exemplary embodiment of the invention consists of methods for evaluating the potential of an agent, such as an anti-E-Cadherin antibody for the prevention of lymphovascular invasion of carcinoma cells by utilizing a immunocompromised host animal inoculated with a human inflammatory breast cancer xenograft, administering the antibody to said inoculated immunocompromised host animal and evaluating its effectiveness. In preferable embodiments of these inventions, the immunocompromised host animal is a nude mouse and the human inflammatory breast cancer xenograft is the xenograft designated MARY-X.

Figure 10:
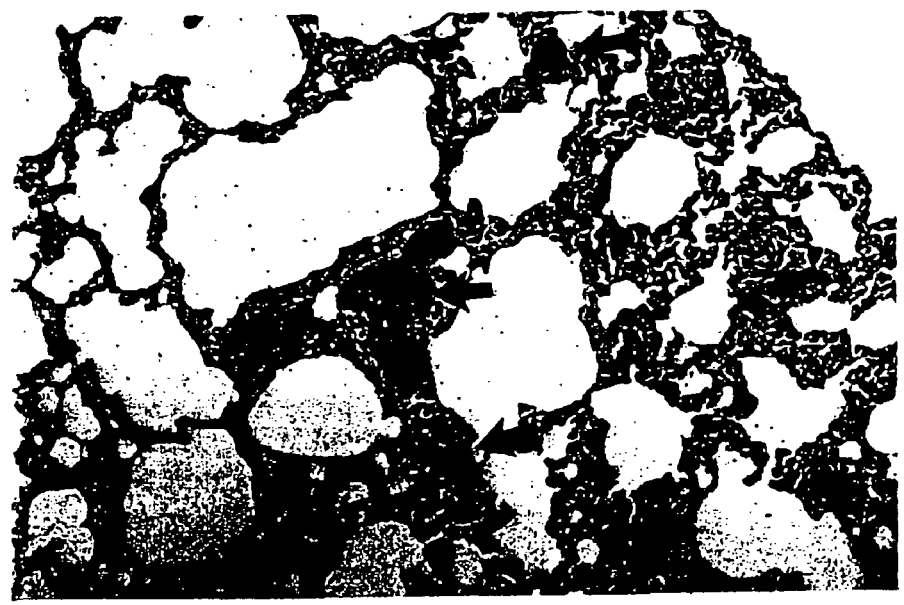
FIG. 10: Mary-X produces lymphovascular emboli in the lung sporadically and spontaneously from the primary subcutaneous xenograft implantation site. The pulmonary lymphovascular emboli do not extravasate and grow as true metastases in the lung but remain confined as lymphovascular emboli. a, Sectioning the lungs and using a primary anti-E-cadherin antibody on the tissue sections demonstrates intense E-cadherin overexpression in these pulmonary emboli excluding the possibility that they represent subclones that have lost E-cadherin expression. b, Injecting murine $IgG_1$ antibodies into the tail veins of mice with lymphovascular emboli of Mary-X and then sectioning the lungs 90 minutes later and then omitting adding the primary E-cadherin antibody to the tissue sections but adding the chromogenic antibodies reveals no non-specific staining. c, Injecting anti-E-cadherin antibodies into the tail veins of mice with lymphovascular emboli of Mary-X and then sectioning the lungs 90 minutes later and then omitting adding the primary E-cadherin antibody to the tissue sections but adding the chromogenic antibodies demonstrates dramatic peripheral circumferential E-cadherin immunoreactivity in the lymphovascular emboli which is what we would expect with successful in vivo immunolocalization (since the tail vein injected antibody would bind only to the outside surface areas of the lymphovascular emboli which on sectioning would reveal their interiors untouched by antibody). d, Daily tail vein injections of anti-E-cadherin for 5 days results in a decrease in both size and number of pulmonary lymphovascular emboli of Mary-X. Since Mary-X represents a model of micrometastases (intravasation without extravasation) this strategy is a potential strategy to treat micrometastasis. Number and size distribution of emboli in representative mid-longitudinal cross-section of lung in E-cadherin-treated versus control group are depicted. 10 sections of each lung were counted and 20 lungs from 10 mice comprised each group. Results are expressed as mean±standard error of the mean.
Figure 10:
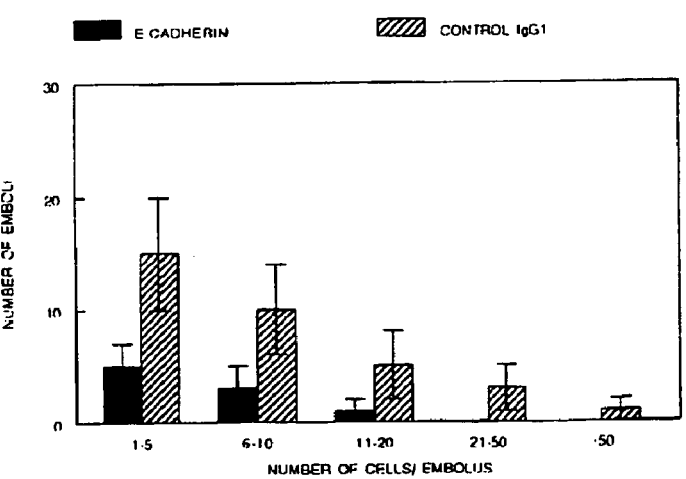
Figure 11:
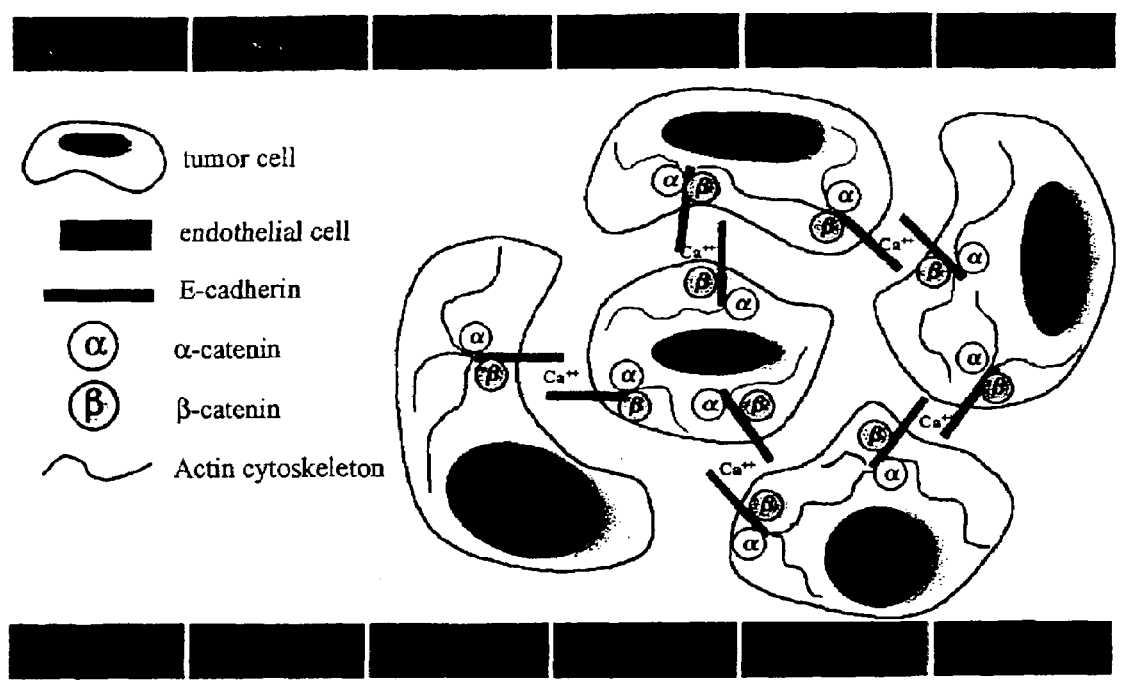
FIG. 11: Schematic depicts tumor cell embolus intravasated within blood vessel or lymphatic (lymphovascular invasion) and the intact and amplified E-cadherin axis which mediates the homophilic interactions between tumor cells within this embolus.

In this context, mice with known pulmonary lymphovascular emboli of MARY-X, receiving a single intravenous tail vein injection of anti-E-cadherin (20 g/100 µl) or control (murine IgG1) demonstrated binding of the anti-E-cadherin but not the control antibody to the cell surfaces of pulmonary vascular emboli of MARY-X, presumably to sites of membrane E-cadherin. Mice receiving 5 successive daily injections of anti-E-cadherin (100 µg/100 µl) but not control showed significant dissolution of pulmonary vascular emboli (p<0.01). These emboli were reduced in both number and size (FIG. 10a, 10b).

The E-cadherin-mediated spheroid formation of MARY-X and its in vivo manifestation of lymphovascular tumor emboli is of similar survival benefit to this cancer. Tumor cell emboli are more effective at forming metastasis than single cells; tumor cell emboli are hypoxic in their centers and therefore more resistant to chemotherapy and radiation therapy than single cells tumor cell emboli probably exhibit their surface determinants in a different conformational state from those present on single cells that would escape recognition and destruction by adoptive immunotherapy strategies which are based on immunizations to single cells (Liotta et al., *Cancer Res.* 36, 889–894 (1976);

Moore et al., *Gynecologic Oncology* 47, 44–47 (1992)). For these reasons it is advantageous to disrupt these tumor cell emboli.

The methods utilizing anti-E-cadherin antibodies were successful both in vitro as well as in our in vivo xenograft model. Therefore, using an intravascular approach one can successfully immunolocalize the pulmonary vascular emboli (micrometastases) with anti-E-cadherin antibodies and hence potentially increase the sensitivity of detection of micrometastases; furthermore one can reduce the vascular embolic burden by causing dissolution of established micrometastases, reducing their number as well as their size.

While E-cadherin is expressed in normal epithelial cells as well as normal endothelial cells these methods for identifying and inhibiting the growth of established micrometastases appears to be tumor specific because E-cadherin is present mainly within the adherens junctions of these normal cells and the tight junctions or zona occludens which lie next to the luminal aspects of endothelial cells would be expected to exclude antibody access with intravenous injection. Hence the E-cadherin antibodies initially reach only the tumor cell emboli within the vascular spaces. The methods for identifying and inhibiting the growth of established micrometastases therefore holds promise of both increasing detection of micrometastases as well as delivering E-cadherin targeted therapy.

This therapy could take a number of forms including using toxins, chemotherapeutic agents or radioisotopes conjugated to E-cadherin antibodies or using the antibody alone to reduce the size and number of micrometastases as an adjuvant therapy.

One unique property of MARY-X which we have exploited in our model is that it manifests the exaggerated phenotype of intravasation which does not, interestingly, progress to extravasation. The vascular emboli remain confined to the pulmonary vasculature. Spontaneously metastasizing xenografts are uncommon but those which exist such as the C8161 produce pulmonary metastases which extravasate and grow in the lungs (Barsky et al., *Oncogene* 15, 2077–2091 (1997)). This is not so with MARY-X. Our approach then is limited to vascular emboli which represent early micrometastases. Significantly, as significant numbers of cancer patients have only early micrometastases, the disclosed methods utilizing anti-E-cadherin antibodies provide a feasible means for both diagnostic and therapeutic modalities.

These findings indicate that it is the overexpression and not loss of the E-cadherin/α-catenin/β-catenin axis that mediates, in part, lymphovascular invasion and the inflammatory breast carcinoma phenotype. While increased MUC-1 expression in breast cancer including inflammatory breast carcinoma is due to gene amplification, increased E-cadherin expression in MARY-X was due to increased transcription (FIG. 7a). This suggested that upstream genetic abnormalities specific for inflammatory carcinoma but still undefined were the cause of the increased E-cadherin transcription. The overexpression of E-cadherin in MARY-X was demonstrated also in actual cases of inflammatory breast cancer as prominent membrane immunoreactivity in immunocytochemical studies (FIG. 7b). The increased membrane and not cytoplasmic localization support our body of evidence that E-cadherin was functioning as an adhesive protein in inflammatory breast carcinoma. Interestingly, increased membrane E-cadherin immunolocalization, was also observed in cases of non-inflammatory breast carcinoma but only in foci of lymphovascular invasion.

Diagnostic and Therapeutic Methods Targeting Molecules Associated with the Inflammatory Phenotype Another embodiment of the invention consists of methods of inhibiting the growth of an inflammatory breast cancer metastases in vivo by administering an effective amount of an anti-E-cadherin antibody so that the growth of an inflammatory breast cancer metastases is inhibited. A related embodiment consists of methods of detecting an inflammatory breast cancer metastases in vivo by administering an effective amount of an anti-E-cadherin antibody so that the inflammatory breast cancer metastases is detected. In one embodiment of this invention, the antibody is joined to a cytotoxic agent or labeled with a detectable marker. Illustrative cytotoxic agents include enzymes, lymphokines, oncostatins or toxins such as ricin. Illustrative detectable markers include paramagnetic isotopes, biotin, fluorophores, chromophores, heavy metals, or radioisotopes.

Also provided herein are methods for inhibiting the development or recurrence of a cancer in a patient, comprising administering to a patient an effective amount of an isolated E-cadherin specific polypeptide comprising an antigen binding site from an antibody capable of specifically binding to an E-cadherin polypeptide, and thereby inhibiting the development of a cancer in the patient. In one embodiment, wherein the cancer is inflammatory breast cancer. Preferably, the isolated E-cadherin specific polypeptide is an isolated polyclonal, monoclonal or chimeric antibody. In one embodiment of this method, the antibody is antibody designated HECD-1.

The invention disclosed herein also provides methods for determining the presence or absence of a cancer in a patient by contacting a biological sample obtained from a patient with an isolated E-cadherin specific polypeptide comprising an antigen binding site from an antibody capable of specifically binding to an E-cadherin polypeptide and then detecting in the sample an amount of this polypeptide that binds to an E-cadherin polypeptide, and then comparing the amount of polypeptide that binds to cells in the sample to a predetermined cut-off value, and therefrom determining the presence or absence of a cancer in the patient therefrom determining the presence or absence of a cancer in the patient. In preferred embodiments of this invention, the E-cadherin specific polypeptide is an antibody and the cancer is inflammatory breast cancer.

The invention disclosed herein also provides methods for monitoring the progression of a cancer in a patient, comprising the steps of contacting a biological sample obtained from a patient at a first point in time with a E-cadherin specific polypeptide and then repeating this process using biological samples obtained from the patient at a subsequent point in time; and then comparing the amount of E-cadherin specific polypeptide detected over time to monitor the progression of the cancer in the patient. In preferred embodiments of this invention, the E-cadherin specific polypeptide is an antibody and the cancer is inflammatory breast cancer.

The disclosure provided herein shows that not only is E cadherin overexpressed but that it is part of an intact and amplified axis where α-catenin and β-catenin are present and also overexpressed and bound to the actin cytoskeleton.

This adhesive network mediates through homodimeric interactions of E-cadherin the tumor cell-tumor cell aggregates so characteristic of lymphovascular emboli observed in lymphovascular invasion. Both absent $Ca^{+2}$ and E-cadherin antibodies disrupt these lymphovascular emboli in vitro promoting the phenomenon we term disadherence. The formation of tumor cell emboli during lymphovascular invasion is of benefit to the tumor and to the detriment of the host. Tumor cell emboli are more effective at forming metastasis than single cells, are hypoxic in their centers and therefore resistant to chemotherapy/radiation therapy, and display their surface determinants in a conformational state that might escape recognition and destruction by adoptive immunotherapy strategies. For these reasons it is advantageous to disrupt these emboli both within the primary tumor as well as within micrometastases. What is disclosed with MARY-X is generally applicable to any cancer which manifests a high degree of lymphovascular invasion and micrometastasis. Most importantly because MARY-X presumably manifests both intravasation and angiogenesis, the use of this unique human tumor xenograft should allow us to dissect out the angiogenic from intravasation phenotypes.

The observed disadherence of the tumor emboli in vivo has clinical implications in that disadherence of the emboli can decrease their metastatic efficiency, decrease their hypoxic centers, make chemotherapy and radiotherapy more potent and even facilitate immunotherapy by providing for easier antigen access and preserving the antigen conformational state of the single cell.

As illustrated above, a variety of antibody embodiments are contemplated including Fv, sFv, Fab, Fab', F(ab') molecules. Additional related embodiments include bispecific antibodies with a binding specificity for two different antigens, one of the antigens being, for example, E-cadherin or MUC1. Another related embodiment includes a recombinant antibody, comprising human constant regions and murine antigen-binding region, wherein the antibody competitively inhibits the binding of monoclonal antibody HECD-1 to E-cadherin. While the specific antibodies disclosed herein functioned to both identify and dissolve micrometastases in vivo, other antibody embodiments such as humanized antibodies can function in this context and can be generated by a variety of methods known in the art. For example, one can generate a human phage library to obtain antibodies and to screen these antibodies for disadherence and inhibitory activity. One exemplary approach is to use an expanded human recombinant phage libraries (Cambridge Centre for Protein Engineering, UK) with the anticipated recovery of Ig-phages that selectively bind to surface E-cadherin. In the case of B cells, DNA rearrangement, combinatory events (i.e., random pairing of heavy and light chains) and specialized "diversity-producing" mechanisms (e.g., N and P nucleotide additions) produces an antibody repertoire of $10^6$ unique molecules. Even more diversity can be achieved with semisynthetic Ig-phage libraries (library size of $10^{13}$ unique molecules). Semisynthetic Ig phage libraries are created by introducing mutations via error prone polymerase, by reshuffling heavy and light chains, or by randomly mutating the heavy chain complementarity determining region 3 (CDR3) of the Ag binding site.

In an illustrative embodiment, a semisynthetic Ig combinatorial phage library can be employed to produce a panel of monoclonal Fabs against purified human E cadherin. Biopanning can be performed. Briefly, 50 µl of an Ig phage suspension ($10^{12}$ pfu) can be incubated with 0.1–1.0 µg of E-cadherin coated on the surface of a microliter well (Costar, 96 well microliter plate; coated overnight at 4° C. in 0.1 M bicarbonate buffer, pH 8.6). Following washing, the bound phage can be gently eluted with 0.1 M HCl. The number of eluted phage can be quantitated by CFU then expanded by re-infection into XLI-Blue bacteria (Stratagene). Three to four subsequent rounds of biopanning typically produces a 100–200 fold enrichment over the original unselected library. Following the last round of enrichment, the clonality of the library can be determined by BstNI digest of the pComb3 phagemid). One can expect 1–5 unique clones each representing a monoclonal Fab. Individual clones can be digested with SpeI and NheI to allow the production of soluble Fab. Fab purity can be determined by SDS-PAGE; the concentration can be quantitated by ELISA using a labeled anti-Fab reagent. Fab specificity for E-cadherin can be confirmed by ELISA; the Fabs are expected not to bind irrelevant proteins. Such antibody embodiments can then be tested following the methods for assessing the activity of the E-cadherin antibodies disclosed herein.

The invention also contemplates molecules (such as antibodies) which target a molecule associated with the inflammatory phenotype (such as E-cadherin) joined to at least a portion of a biologically or chemically active molecule (Batra et al., Proc. Natl. Acad. Sci. USA 86:8545–8549 (1989); Kondo et al., J. Biol. Chem. 263:9470–9475 (1988); and Batra et al., Proc. Natl. Acad. Sci. USA 86:8545–8549 (1989). A biologically or chemically active molecule, such as a cytotoxic agent, can inhibit or arrest cell growth or otherwise act to the detriment of the cell. The biologically or chemically active molecule, such as a diagnostic agent, can facilitate the identification of the cell.

In accordance with the practice of the invention, biologically or chemically active molecules include, but are not limited to, an enzyme, lymphokine, a toxin, a paramagnetic isotope, biotin, a fluorophore, a chromophore, a heavy metal, a radioisotope, or a chemotherapeutic agent. Suitable examples of toxins include, but are not limited to, *Pseudomonas* exotoxin, ricin, bryodin, and diphtheria toxin. Additional examples include bleomycin, dactinomycin, daunorubicin, doxorubicin, mitoxantron, mitomycin, cisplatin, and procarbazine.

Genetic engineering techniques known in the art can be used as described herein to prepare recombinant immunotoxins produced by ligating a DNA sequence encoding an antigen binding region of an E-cadherin specific antibody with a DNA sequence encoding a biologically or chemically active molecule at the DNA level and expressing in a transformed host cell the cytotoxic molecule as a recombinant protein. Recombinant immunotoxins are homogenous molecules that retain the specificity of the cell binding portion of the E-cadherin antibody with the cytotoxic potential of the toxin (Kondo et al., J. Biol. Chem. 263:9470–9475 (1988); Siegall et al., Proc. Natl. Acad. Sci. USA 85:9738–9742 (1988) Pastan, I., and FitzGerald, D. (1991). Recombinant toxins for cancer treatment. Science 254, 1173–1177. Pastan, I., Willingham, M. C., and FitzGerald, D. J. (1986). Immunotoxins. Cell 47, 641–648).

Recombinant immunoconjugates, particularly single-chain immunoconjugates have an advantage over drug/antibody conjugates in that they are more readily produced than these conjugates, and generate a population of homogenous molecules, i.e., single polypeptides composed of the same ammo acid residues (Trail, P. A., et al. Cure of xenografted human carcinomas by BR96-doxorubicin immunoconjugates. Science, 261:212–215, 1993). When the biologically or chemically active molecule is a toxin or drug, the conjugate is more potent than its non-conjugated counterpart.

Methods for Analyzing Related Inflammatory Cancer Phenotypes

The exaggerated phenotype exhibited by inflammatory carcinoma is exhibited to a lesser degree by all cancers which do not remain organ confined. Cancers which metastasize must exhibit either lymphatic or vascular invasion at some point in their metastatic route. For example, pancreatic adenocarcinoma is one of the most lethal of all malignancies with a mortality rate in excess of 95% because the disease does not stay organ-confined for long, precluding a curative surgical resection and forcing us to use radiation and chemotherapy which to date have shown only minimal benefits. Similarly to inflammatory breast carcinoma, pancreatic cancer disease manifests lymphovascular invasion as a prelude to regional metastasis. Even when micrometastases exist, many of these are thought to be at the stage of intravasation, existing as tumor emboli within the subcapsular sinuses of lymph nodes and liver. Therefore, utilizing the information disclosed herein, one can study the phenotype of pancreatic adenocarcinoma.

For example, one can screen a number of human pancreatic cancer cell lines for E-cadherin expression. These can include standard pancreatic cancer cell lines which range from the well-differentiated CAPAN-1 to the undifferentiated MiaPACA2. They can also include CAPAN-2, ASPC-1, PANC-1 and PANC-2. One expect that some of these lines can have absence of E-cadherin expression and some can overexpress this adhesion molecule. One can then test the functional properties of the E-cadherin adhesion pathway in the lines which overexpress E-cadherin by attempting to block adhesion of these lines to an epithelial monolayer, for example, normal human mammary ductal cells. As disclosed herein, both low $Ca^{+2}$ and E-cadherin antibodies can block attachment of fragments of MARY-X to this monolayer. They can also cause disadherence of the spheroids of MARY-X or disruption of the tumor emboli in vitro. One can investigate whether achieve similar results in vitro with select pancreatic cancer lines and one can compare the results from those lines that overexpress E-cadherin, those lines that do not express it, and those that express it but have their E-cadherin adhesion axis disrupted by either abnormal α-catenin or β-catenin. Since one also expect that the majority of pancreatic cancer cell lines, like pancreatic cancer in humans, can also overexpress MUC1 and that this MUC1 may mediate the adhesion of pancreatic cancer cells to endothelial cells, which after all is another component of the tumor embolic phenomenon of lymphovascular invasion, one can examiune the effects of MUC1 antibodies on adhesion of pancreatic cells to both epithelial and endothelial monolayers.

Adhesion (attachment) assays and neutralizing effects of antibodies. Following the methods disclosed herein for breast cancer, it is possible to assess the cell-cell and cell-substrate adhesion of pancreatic cancer cell lines differ with different substrates and different monolayers and is a specific type of adhesion preferentially mediated by MUC1 and/or E-cadherin. For example it is possible to determine whether MUC1 preferentially mediates the binding of pancreatic cancer cells to endothelial cells (heterotypic interactions) and whether E-cadherin preferentially mediates the adhesion of pancreatic cancer cells to epithelial cells and to each other (homotypic interactions)? Specifically, the pancreatic cancer cell lines previously mentioned can be labelled with [$^{125}$I] 5-odo-2'-deoxyuridine (IUdR) and a number of different attachment assays carried out as described previously. Attachment to an uncoated plastic surface (tissue culture dish), purified matrix components (types I and IV collagens, fibronectin, laminin etc.), Humatrix (an extracted human myoepithelial matrix), a monolayer of human umbilical vein endothelial cells (HUVECs), and a monolayer of human mammary epithelial cells (HMECs) can be carried out over 1–4 hr or longer. The specific effects of neutralizing antibodies to MUC1 and E-cadherin can be observed in each of these attachment assays to determine which particular adhesion protein functions in which specific type of cell-cell and cell-substrate interaction. The results with pancreatic carcinoma cell lines which overexpress MUC1 and E-cadherin can be compared to lines which express low/absent levels.

Adhesion assays and effects of pharmacological manipulations. Both the monolayer feeder layer (endothelial or epithelial cells) and the target layer (the different pancreatic carcinoma cell lines) can be pretreated with specific agents designed to perturbate adhesion and shed light on specific molecular interactions. For example the HUVEC monolayer can be preteated with IL-1α and/or TNF-α to upregulate E selectin and then whether adhesion of pancreatic cancer is enhanced via a MUC1 mechanism can be investigated. If these treatments result in increased attachment, this would support the role of MUC1 in mediating heterotypic adhesion (between carcinoma cells and endothelial cells). Alternatively, one can reduce the levels of MUC1 on either the pancreatic carcinoma cell lines or the HMEC monolayer with either sodium butyrate (NaB) or ubenimex treatment (two known inhibitors of MUC1 transcription) or with antisense MUC1 oligonucleotides and the effects on adhesion in this latter setting can be examined. If these treatments result in decreased adhesion, this would support the role of MUC1 in homotypic interactions; on the other hand if adhesion is increased, it would support the antagonism of MUC1/E-cadherin as has been suggested. Neutralizing antibodies can also be examined in the context of these pharmacological treatments.

Cadherin-catenin complex phosphorylation and effects of tyrosine kinase inhibitors. Since tyrosine phosphorylation of the cadherin-catenin complex and dephosphorylation of β-catenin are thought to either decrease or increase cadherin-mediated adhesion, the expression and tyrosine phosphorylation of the cadherin-catenin complex can be examined in the different pancreatic carcinoma cell lines. The components of the complex can be measured by Western blot with the appropriate antibodies first in the untreated pancreatic carcinoma lines. The effects of NaB and/or ubenimex treatment on the cadherin-catenin complex can be measured. Cadherin-catenin complex phosphorylation can be determined with immunoprecipitation studies with the same antibodies followed by Western blot of the precipitans with an antiphosphotyrosine antibody. The effects of the previous drugs on phosphorylation of this complex can be determined along with effects of tyrosine kinase inhibitors (herbimycin/genistein). The effect of NaB/ubenimex on adhesion in the presence/absence of tyrosine kinase inhibitors can be studied. One can see whether phosphorylation of the cadherin-catenin complex contributes to the adhesive properties of pancreatic carcinoma cell lines.

Transfections. Using the mammalian expression vector, pCMV-Poly1 and -Poly2 containing the human MUC1 and the human E-cadherin genes in both sense and antisense orientations respectively, stable transfections can be carried out in selected pancreatic carcinoma lines depending on their constitutive levels of expression of the relevant molecules which can have been determined previously. Some of the lines can be double transfected with both MUC1 and E-cadherin using pSV2neo and pSV2hygro selection. Transfectants containing all combinations of sense/antisense constructs can be produced. The effects on adhesion can be determined in in vitro assays; the effects of neutralizing antibodies likewise examined.

With these types of combination experiments, one hope to determine whether there is synergism, antagonism or complementation between MUC1-mediated and E-cadherin-mediated adhesion in pancreatic carcinoma. It is reasonable to hypothesize that the homophilic aggregation manifested by the tumor plugs may be mediated predominantly by E-cadherin whereas the heterotypic tumor cell-endothelial cell adhesion manifested by lymphovascular invasion, may be mediated by MUC1.

In Vivo Studies with Orthotopic Human Pancreatic Carcinoma Xenografts

Based on our in vitro work, one can select those pancreatic carcinoma cell lines most able to be perturbed with our anti-E-cadherin and/or anti-MUC1 strategies. Previous studies have observed that when the tumor cells are injected orthotopically into or adjacent to the pancreas, the tumor cells grow as nodules, manifest lymphovascular invasion with tumor emboli and metastasize to the regional lymph nodes, liver and lungs after 4–8 weeks. Although the injection of pancreatic carcinoma cell lines orthotopically into the pancreas of mice is a fully artificial system as far as the multistep pathway of carcinogenesis is concerned, from the standpoint of lymphovascular invasion and metastasis, it is not at all artificial. In fact it fairly consistently reproduces the pattern of metastasis occurring autochthonously. Therefore the experiments one can conduct are as follows: One can inject $10^6$ pancreatic carcinoma cells orthotopically and observe their baseline patterns of metastasis. Then in experimental groups one can infuse E-cadherin antibodies via the tail veins on a regular dose schedule. One can determine the half-life of circulating E-cadherin and MUC1 antibodies to guide a dose schedule. One can then vary the dose and dose schedule of antibody in an attempt to reduce both the number and size of metastasis. One can then use both a conventional metastasis assay of counting number and size of metastatic colonies in the liver/unit area or use a more quantitative and sensitive assay utilizing PCR of specific human Alu repeats. This latter approach has been used successfully in detecting small number of human tumor cells in the chick chorioallantoic membrane assay. One can use an identical approach in the murine liver of detecting and quantitating micrometastases. If E-cadherin antibodies are successful in causing disadherence of the tumor emboli within lymphovascular channels in the primary tumor as well as the micrometastases and if, in fact, the size of these tumor emboli are a critical determinant of the efficiency of the metastatic process, then one should observe some degree of metastasis inhibition in our experimental groups. One can use an analogous approach with our MUC1 antibodies.

The effects of our antisense transfections in the pancreatic carcinoma cell lines produced in the previously mentioned in vitro studies can be examined in vivo as far as metastatic efficiency is concerned and also in tandem with antibody injection studies.

Kits and Articles of Manufacture

In a further embodiment of the invention, there are provided articles of manufacture and kits containing the polypeptides and antibodies which can be used, for instance, for the therapeutic or non-therapeutic applications described above. The article of manufacture comprises a container with a label. Suitable containers include, for example, bottles, vials, and test tubes. The containers may be formed from a variety of materials such as glass or plastic. The container holds a composition which includes an active agent that is effective for therapeutic or non-therapeutic applications, such as described above. Typically, the active agent in the composition is an isolated E-cadherin specific polypeptide comprising an antigen binding site from an antibody capable of specifically binding to an E-cadherin polypeptide. The label on the container indicates that the composition is used for a specific therapy or non-therapeutic application, and may also indicate directions for either in vivo or in vitro use, such as those described above.

The kit of the invention will typically comprise the container described above and one or more other containers comprising materials desirable from a commercial and user standpoint, including buffers, diluents, filters, needles, syringes, and package inserts with instructions for use.

The present invention is further detailed in the following Examples, which are offered by way of illustration and are not intended to limit the invention in any manner. All patent and literature references cited in the present specification are hereby incorporated by reference in their entirety.

EXAMPLES

Example 1

Generation and Propagation of Cell lines and Xenografts

Informed patient consent and certification from the UCLA Human Subject Protection Committee was obtained prior to all studies. Approval from the Chancellor's Animal Research Committee was requested and obtained, certification ARC #95–127-11. The MARY-X xenograft was established directly from a 45 year old female who presented with a warm and erythematous breast and ill-defined mass. The mass was biopsied and diagnosed as inflammatory carcinoma exhibiting florid invasion of dermal lymphatics. Minced 1 $mm^3$ portions of the biopsy were washed in Hank's balanced salt solution, placed in RPMI media and subsequently implanted subcutaneously in several female scid and athymic (nude) mice (nu/nu mutants on a BALB/c background). The tumoral xenografts which grew were subsequently transplanted when they reached 1 cm in diameter. Following this procedure, an illustrative stable serial transplantable xenograft designated MARY-X was successfully established in both scid and nude rice.

The MDA-MB-231, MDA-MB-468 and PC-3 cell lines, obtained from the American Type Culture Collection (Rockville, Md.) were grown in DMEM (GIBCO-BRL) containing 10% fetal calf serum and antibiotics (100 units/ml penicillin and 100 $\mu$g/ml streptomycin) in an air-5% $CO_2$ atmosphere at constant humidity. Human myoepithelial cell lines and xenografts (HMS-1, HMS-X, HMS-3 and HMS-3X) previously established by us (Sternlicht et al., *In Vitro Cell Dev. Biol.* 32:550–563 (1996); Sternlicht et al., *Clin. Cancer Res.* 3:1949–1958 (1997) and Sternlicht et al., *Lab. Invest.* 74:781–796 (1996).) were also used. MARY-X spheroids were obtained by suspending the MARY-X "shake" in KSFM with supplements. MDA-MB-231 and MDA-MB-468 cells were in injected 1×$10^6$) subcutaneously into the ventrolateral flanks of nude and scid mice (Charles Rivers) and allowed to grow into 1–1.5 cm tumors before the tumors were excised. MARY-X and HMS-3X are human tumoral xenografts developed by us and maintained subcutaneously in nude and scid mice. The C8161 line and xenograft were also used in previous studies. The MARY-X "shake", an enriched population of human tumor cells, 99% free from murine components, was produced by extirpating MARY-X, placing it in culture media, immediately making parallel incisions without transecting the tumor and gently agitating the culture media at 4° C. for 2 minutes. The tumor proper was then removed and the tumor "shake" was centrifuged at 1700 g×2 minutes. The "shake" consisted of spheroids which grew both in suspension as well as attached to monolayers of epithelial as well as endothelial cells. Normal human mammary epithelial cells (HMECs) (Clonetics) and normal human endothelial cells (HUVECs) (Clonetics) were used. The "shake" consisted of spheroids which grew in suspension. These spheroids were maintained by suspending the MARY-X "shake" in keratinocyte serum-free medium with supplements (KSFM) (Life Technologies, Inc., Gaithersburg, Md.). A murine specific COT-1 probe verified that the MARY-X "shake" was 99% human.

Example 2

Analysis of MARY-X Xenograft

Histopathological studies. Xenografts were processed for routine light microscopic, immunocytochemical and ultrastructural studies according to standard protocols. Human cases of inflammatory and non-inflammatory breast cancer were retrieved from archival material and studied immunocytochemically.

DNA profiling. High molecular weight DNA was extracted from the xenografts and host murine tissues by standard procedures (Sambrook, J., Fritsch, E. F., and Maniatis, T. Molecular cloning: a laboratory manual. $2^{nd}$ ed. Cold Spring Harbor, N.Y.: Cold Spring Harbor Laboratory Press. 1989), digested with HaeIII and HinfI and probed with the multilocus 33.6 Jeffeys probe (Jeffreys, A. J., Wilson, V., and Thein, S. L. Hypervariable "minisatellite" regions in human DNA. Nature, 314: 67–73, 1985) (Cellmark Diagnostics, Germantown Md.). This probe recognizes both human as well as murine DNA. A human-specific [$\alpha$-$^{32}$P] dCTP-labeled human Cot-1 DNA probe (GIBCO-BRL, Gaithersburg, Md.) was used to confirm the human identity of the xenograft. A murine-specific [$\alpha$-$^{32}$P] dCTP-labeled mouse Cot-1 DNA probe (GIBCO-BRL, Gaithersburg, Md.) was used to distinguish murine from human DNA and quantitate the murine DNA component of the xenografts.

Western blot and zymography analysis. MARY-X was compared to non-inflammatory xenografts with respect to candidate effector molecules. Tissue lysates and primary antibodies to candidate adhesion molecules and angiogenic factors were used in standard Western analyses (Sternlicht, M. D., Safarians, S., Rivera, S. P., and Barsky, S. H. Characterizations of the extracellular matrix and proteinase inhibitor content of human myoepithelial tumors. Lab. Invest., 74: 781–796,1996). Goat anti-mouse antibodies were used as secondary antibodies and the signals were developed with the ECL System (Amersham Life Sciences, Arlington Heights, Ill.) Standard zymography analysis was also used to compare levels of proteolytic enzymes (DeClerck, Y. A. Purification and characterization of a collagenase inhibitor produced by bovine vascular smooth muscle cells. Arch. Biochem. Biophys., 265: 28–37, 1988). Immunocytochemistry and FISH. MARY-X, its primary tumor of origin and the non-inflammatory xenografts previously mentioned were studied with selected monoclonal antibodies to ER and PR (Abbot Laboratories, Chicago, Ill.), EGFR (Ciba-Corning Diagnostic Corporation, East Walpole, Mass.), p53 and Her-2/neu (Oncogene Sciences, Inc., Uniondale, N.Y.). MARY-X was also studied with polyclonal rabbit antibodies to von Willebrand factor (DAKO, Carpinteria, Calif.) and monoclonal antibodies to E-cadherin (Zymed Laboratories, Inc., San Francisco, Calif.), MUC1 (Research Diagnostics, Inc., Flanders, N.J.). The latter two antibodies were also used on cases of human inflammatory and non-inflammatory carcinoma. All antibodies were used at their manufactures' recommended dilutions. Peroxidase-conjugated sheep anti-mouse IgG or goat anti-rabbit was used as secondary antibody. Colorimetric detection of peroxidase-conjugated secondary antibody was with diaminobenzidine. Her-2/neu FISH was carried out on tissue sections of both MARY-X as well as its primary tumor of origin with a Her-2/neu probe spanning approximately 140 kb of the chromosomal region. This probe was directly labelled with the fluorophore SpectrumOrange™ (Vysis, Inc., Downers Grove, Ill.) (14). As a control for chromosomal 17 aneusomy, a chromosome 17-specific centromeric $\alpha$-satellite probe (D17Z1) (Giovanni, P., Godolphin, W., Press, M. F., and Slamon, D. J. Detection and quantitation of HER-2/neu amplification in human breast cancer archival material using fluorescence in situ hybridization. Oncogene, 13: 63–72, 1996) (Vysis, Inc., Downers Grove, Ill.) was used. This latter probe was biotin-labelled and detected via avidin-FITC. Tissue sections were counterstained using 0.15 mM 4,6-diamidino-2-phenylindole (DAPI) (Sigma Chemical Co., St. Louis, Mo.). A Zeiss epifluorescence microscope with single band pass combinations was used to measure the different wavelength fluorescences.

Western, zymographic, northern and southern analysis. The xenografts were excised and immediately frozen in liquid nitrogen and pulverized with mortar and pestle to a fine powder and extracted with buffer (1% triton X-100, aprotinin (2 $\mu$g/ml), leupeptin (21 g/ml), NaF (100 mM), sodium orthovanadate (2 mM), NaCl (150 mM), sodium phosphate (10 mM), EDTA (10 mM)) for 4 hours at 4° C. with gentle agitation. The samples were then centrifuged at 13,000 g at 4° C. for 15 minutes. Protein concentrations were determined using the Bio Rad reagent (BioRad Laboratories, Hercules, Calif.). Samples were boiled in a 1×Leammli buffer under reducing conditions, run on a 7.5% SDS-polyacrylamide gel and transferred to a nitrocellulose membrane which was incubated with the primary and secondary antibodies and signal detected with the ECL detection system (Amersham Life Sciences, Arlington Heights, Ill.). Metalloproteinases were detected by direct gelatin zymography according to previous methods. Genomic DNA was extracted using standard methods and digested overnight with EcoRI (Gibco BRL) and run on a 1.0% agarose gel. Total RNA was extracted using TRIzol reagent (Gibco-BRL), 20 ug of total RNA was loaded onto a denaturing formaldehyde 1.2% agarose gel and Northern blot analysis was performed as previously described (Shao et al., Exp. Cell Res. 241, 394–403 (1998)). The E-cadherin cDNA, a 2.7 kb of the 3' region was excised from plasmid, PERF-2 (pCMV-NeoPoly2) (a gift from Dr. David Rimm, Yale University), the insert was cut from the plasmid using a combination of restriction enzymes, EcoRV and XhoI (Stratagene, Lajolla, Calif.) and labelled by random priming (Megaprime DNA labelling system, Amersham Life Sciences, Arlington Heights, Ill.). The housekeeping probe, 36B4 (a gift of Dr. Judy Berliner, UCLA) was used to normalize for RNA loading. All of the above methods were performed also on the MARY-X "shake", the enriched population of MARY-X spheroids.

The MARY-X phenotype. The MARY-X phenotype was one of florid local lymphovascular emboli formation with occasional pulmonary lymphovascular emboli. In MARY-X the murine component was considerable (~30%). However we could effectively separate the human from the murine stromal and vascular component in vitro. We called this separation the MARY-X "shake" or the MARY-X spheroids.

MARY-X spheroids when reinjected into nude/scid mice exhibited the complete MARY-X phenotype of florid lymphovascular invasion.

Comparisons of MARY-X with non-inflammatory xenografts. Because the inflammatory carcinoma phenotype displayed by MARY-X was characterized by homophilic tumor emboli present within lymphovascular spaces, we reasoned that the mechanism likely involved adhesion molecules on tumor cells and/or angiogenic factors and/or proteolytic enzymes elaborated by tumor cells all of which might facilitate intravasation. Initial studies compared MARY-X with the aggressive non-inflammatory breast carcinoma xenografts, MDA-MB-231-X, MDA-MB-468-X, the aggressive human melanoma xenograft, C8161-X and the human myoepithelial xenograft, HMS-3X and revealed that the two major differences were both in the adhesion class of molecules, namely marked increased expression of MUC-1 and E-cadherin (FIG. 6a) in MARY-X. No differential expression in the 72 kD and 92 kD matrix metalloproteinases in MARY-X compared to the aggressive non-inflammatory xenografts was evident (FIG. 6b); although OPA and OPAR were both increased in MARY-X, they were not increased over those levels exhibited by the aggressive non-inflammatory xenografts, C8161-X, MDA-MB-231-X and MDA-MB-468-X. There was also no increased expression of angiogenic factors including VEGF and PD-ECGF in MARY-X compared to the aggressive non-inflammatory breast carcinoma xenografts, MDA-MB-231 and MDA-MB-468 (FIG. 6c). The overexpression of the two adhesion molecules, MUC1 and E-cadherin was even more marked in the MARY-X "shake" and the MARY-X spheroids than in MARY-X indicating that the source of this overexpression was the human breast carcinoma cells themselves and not the murine stromal or vascular component. Overexpression of MUC-1 had been observed in many different non-inflammatory breast carcinomas (O'Connell et al., *Human Pathology* 29:1517–1523 (1998)) but overexpression of E-cadherin was a new finding. Although loss of E-cadherin was the rule in some human breast carcinomas and cell lines, other breast carcinomas and cell lines retain strong E-cadherin expression. For this reason we compared the levels of E-cadherin expression in the MARY-X spheroids with both E-cadherin positive and negative cell lines/xenografts (FIG. 7). The MARY-X spheroids overexpressed E-cadherin 3–5 fold greater than other E-cadherin expressing breast carcinoma cell lines, normal mammary epithelial cells and myoepithelial cells (FIG. 7). α- and β-catenins were similarly overexpressed (FIG. 8).

In MARY-X E-cadherin overexpression is due to increased steady state mRNA. Whereas increased MUC-1 expression in breast carcinoma including ibc is due to gene amplification (O'Connell et al., *Human Pathology* 29:1517–1523 (1998)) increased E-cadherin expression in MARY-X was due to increased steady state mRNA levels which also exceeded the levels of other E-cadherin positive lines, normal mammary epithelial cells and myoepithelial cells. This increase in E-cadherin expression was not due to gene amplification or rearrangement. The increased steady state mRNA levels was due to increased transcription as determined by a nuclear run-on assay and not increased mRNA stability. This suggested that upstream genetic abnormalities related to the ibc phenotype but still undefined were causing the increased E-cadherin expression. The overexpression of E-cadherin in MARY-X was also manifested as prominent membrane immunoreactivity (FIG. 7). α- and β-catenin showed a similar pattern of membrane immunoreactivity. β-catenin did not show nuclear immunolocalization. The increased membrane and not cytoplasmic localization of E-cadherin/α-, β-catenins supported but did not prove our notion that this axis was functioning in adhesion in MARY-X.

In MARY-X the E-cadherin axis is structurally intact. The observation that E-cadherin was 3–5 fold overexpressed in MARY-X compared to strong E-cadherin positive non-inflammatory breast carcinoma cell lines/xenografts and myoepithelial lines/xenografts, merited close scrutiny as to its significance. E-cadherin expression generally has been thought to be either lost in malignant progression or rendered non-functional through structural changes in the E-cadherin molecule (or associated catenin axis) or cleavage by extracellular proteases (Birchmeier et al., *Biochimica et Biophysica Acta* 1198:11–26 (1994); Gumbiner et al., *Cell* 84:345–357 (1996); Yap et al., *Annu. Rev. Cell Dev. Biol* 13:119–146 (1997); Ben-Ze'ev et al., *Current Opin. Cell Biol.* 10:629–639 (1998); and Pierceall et al., *Oncogene* 11: 1319–1326 (1995)). E-cadherin as an adhesion molecule is found in normal cells as part of a membrane complex with α-catenin and β-catenin which form the adherens plaque. The modular architecture of the E-cadherin molecule consists of five repeats in the extracellular domain, a single transmembrane region and a single intracellular domain linked to the actin filaments of the cytoskeleton via α and β catenins (Alattia et al., *FEBS Letters* 417:405–408 (1997)). The specific homophilic-binding capacity of the extracellular domain of E-cadherin (EC1) translates into stable cell adhesion via antiparallel dimers. Disruption of any part of this axis causes non-adhesion rather than adhesion. E-cadherin which has lost either extracellular domains or cytoplasmic domains, the absence of α-catenin or abnormally phosphorylated β-caterin and the absence of this complex's binding to the actin cytoskeleton all leads to the non-adhesive state. The E-cadherin adhesive state is also $Ca^{++}$ dependent; absence of $Ca^{++}$ disrupts the homodimeric interactions between repeat motifs within the EC1 domains of the E-cadherin molecule (see e.g. Troxell et al., *Am. J. Physiol.* 276: C404–C418 (1999); and Koch et al., *Biochemistry* 36:7697–7705 (1997)) and in addition, is probably chaotropic for the intracellular interactions with the catenins and the actin cytoskeleton. Some cancers may overexpress a structurally defective E-cadherin molecule or exhibit structural disruption of the E-cadherin axis. For example in the PC-3 prostatic carcinoma line, there is expression of E-cadherin but a complete absence of α-catenin due to homozygous deletions of the α-catenin gene (Kaighn et al., *Invest. Urology* 17:16–23 (1979); and Morton et al., *Cancer Res.* 53:3585–3590 (1993)). This line, as a result, has absent E-cadherin axis function despite the presence of E-cadherin. Therefore the demonstration that E-cadherin overexpression in MARY-X was actually contributing to increased adhesion and the ibc phenotype of lymphovascular emboli formation would require a number of studies demonstrating that the complete E-cadherin axis was structurally intact as well as overexpressed and overfunctioning. The E-cadherin protein, in fact, was fully intact in MARY-X (full 120 kD size) (FIG. 7) and therefore had not lost either extracellular or cytoplasmic domains. Long triton X-100 solubility extraction of MARY-X or the MARY-X spheroids in the absence of $Ca^{++}$ resulted in partitioning of the E-cadherin in the soluble fraction whereas triton X-100 extraction in the presence of $Ca^{++}$ demonstrated that the E-cadherin was bound in the particulate (membrane) fraction (FIG. 7). Not only were both α-catenin and β-catenin present in MARY-X but actually were also overexpressed (FIG. 8). Short triton X-100 solubility extraction in the presence of $Ca^{++}$ resulted in coprecipitation of E-cadherin, α-catenin, β-catenin and cytoskeletal actin in the particulate (membrane) fraction in MARY-X in contrast to the PC-3 cells where E-cadherin fractionated in the soluble fraction unbound to cytoskeletal actin (FIG. 8). Co-immunoprecipitation studies with anti-E-cadherin antibodies followed by a Western blot phosphotyrosine analysis of β-catenin revealed that β-catenin, when normalized for protein, was phosphorylated to the same degree in MARY-X as it was in HMEC and HMS-3X and certainly not overphosphorylated (FIG. 8). In fact, a direct immunoprecipitation strategy employing anti-β-catenin instead of anti-E-cadherin yielded similar results in terms of the degree of β-catenin phosphorylation (FIG. 8). Although this direct immunoprecipitation precipitated more β-catenin than the E-cadherin co-immunoprecipitation, the ratio of the β-catenin precipitated by the β-catenin method compared to the E-cadherin method was no different in MARY-X, HMS-3X or HMEC (Fig. Ec). Since the last two represent normal myoepithelial and epithelial cells respectively, cells where β-catenin is thought to function only as a plaque protein and not as a transcription factor, we concluded from this data that in MARY-X, β-catenin functions only as a plaque protein. As has been established, free and abnormally phosphorylated catenins can play a central role in signal transduction and the regulation of gene expression; however we found in MARY-X no evidence of free cytoplasmic or nuclear β-catenin and no evidence of abnormal phosphorylation. Furthermore there was no evidence in MARY-X that the E-cadherin molecule was cleaved or shed from the cell surface as no circulating E-cadherin could be detected in murine serum even when MARY-X tumors were allowed to grow to a large (2 cm) size (FIG. 8). These collective results all suggested that the entire E-cadherin axis in MARY-X was intact. The demonstration of structural integrity of the E-cadherin axis however did not necessarily demonstrate functional integrity so studies had to be conducted to address this issue.

Figure 9:
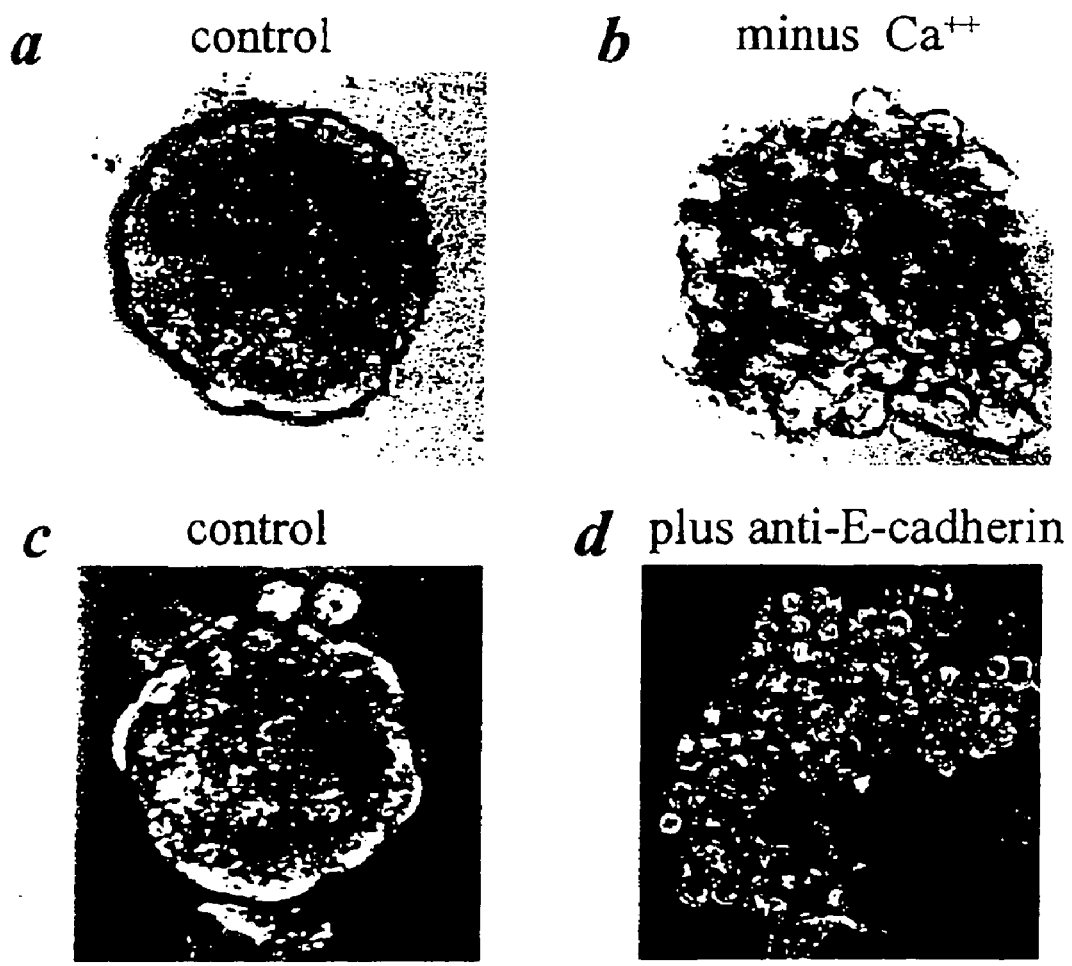
FIG. 9: The MARY-X "shake" is comprised of tight spheroids of tumor cells which correspond in vivo to the tumor emboli within lymphovascular channels. a,c, in vitro these spheroid will grow and enlarge either in suspension or attached to a monolayer; b, in the absence of $Ca^{++}$, these spheroids undergo disadherence between 2–6 hours; d, in the presence of anti-E-cadherin antibodies, these spheroids undergo disadherence between 6–12 hours. Complete disadherence of the spheroids is eventually observed with either manipulation.

In MARY-X the E-cadherin axis is functionally intact, overfunctional and uniquely susceptible to perturbation. The MARY-X "shake" produced the appearance of very tight spheroids which grew in suspension culture (FIG. 9). The MARY-X spheroids disadhered when placed in media containing absent $Ca^{++}$ or anti-E-cadherin antibodies. The disadherence effect of no $Ca^{++}$ was in evidence after 2 hours and was complete after 6 hours; the disadherence effect of anti-E-cadherin antibodies was in evidence after 6 hours and was complete after 12–24 hours depending on the size of the spheroid. MARY-X spheroids, in contrast to other non-inflammatory carcinoma aggregates, formed round very compact structures with a cell density 5–10 fold higher ($10^3$ cells in a spheroid 120 μm in diameter) than other strong E-cadherin expressing breast carcinoma cell lines. The MARY-X spheroids remained permanently in suspension and did not lie down to form monolayers. All other cellular aggregates (both E-cadherin positive and negative) were less round, less compact and more loosely associated and did not remain permanently in suspension but formed monolayers. The effects of anti-disadherence strategies (low $Ca^{++}$, anti-E-cadherin) were more spectacular with the spheroids of MARY-X causing a dramatic and total release of individual cells in large numbers (FIG. 9). With the E-cadherin negative lines these anti-disadherence maneuvers had no effect; with the E-cadherin positive lines these maneuvers had some anti-disadherence effects but the effects were less spectacular resulting in a loosening rather than a total disadherence. Furthermore with the MARY-X spheroids, anti-MUC-1, anti-CD44 and control murine IgG1 did not produce disadherence. These findings indicate that specific and increased homophilic E-cadherin interactions cause the compact spheroid formation observed in the MARY-X spheroids in vitro and suggest that these same E-cadherin homophilic interactions mediate the formation of the tumor embolus within lymphovascular spaces in vivo. This unique functional dependency of MARY-X on its overexpressed E-cadherin/(α-, β- catenin axis establishes a "special" role for the E-cadherin-catenin axis in MARY-X and the inflammatory carcinoma phenotype. Lymphovascular invasion and the inflammatory phenotype is governed then by the gain rather than the loss of E-cadherin function. One can not help but draw analogies between the MARY-X spheroid (lymphovascular embolus) and the 8–16 cell embryonic blastocyst. Increased E-cadherin expression mediates the formation and the compaction of both of these structures. The blastocyst is destined for implantation in the uterus just as the lymphovascular embolus is destined for implantation at its metastatic site. The pulmonary lymphovascular emboli in MARY-X retained their strong expression of E-cadherin negating the hypothesis that loss of E-cadherin contributes to metastasis. Mice with pulmonary lymphovascular emboli of MARY-X, receiving a single intravenous tail vein injection of anti-E-cadherin (20 μg/100 μl) or control (murine IgG1), demonstrated binding of the anti-E-cadherin but not the control antibody to the cell surfaces of pulmonary vascular emboli of MARY-X, presumably to sites of membrane E-cadherin. Mice receiving 5 successive daily injections of anti-E-cadherin (100 μg/100 μl) but not control showed significant dissolution of their pulmonary vascular emboli ($p<0.01$).

Dominant negative E-cadherin transfection abolishes spheroid formation in vitro and lymphovascular emboli formation in vivo. Retroviral transfection with MSCV-GFP successfully delivered this reporter gene to the outer layer of cells within the MARY-X spheroid but caused no disadherence. Retroviral transfection with both Babe-H-2 $K^d$-E-cad and Babe-H-2 $K^d$-E-cad✣ C25 produced evidence of chimeric gene expression but only Babe-H-2$K^d$-E-cad produced disadherence beginning at 72 hours. Repeated transfections with Babe-H-2 $K^d$-E-cad resulted in complete and total disadherence of the MARY-X spheroids. GFP and H-2 $K^d$-E-cad✣C25 transfected spheroids (non-disadhered) were 100% tumorigenic in nude/scid mice and maintained the characteristic MARY-X phenotype of florid local lymphovascular emboli and occasional pulmonary lymphovascular emboli whereas H-2 $K^d$-E-cad transfected spheroids (disadhered) were only 10% tumorigenic and produced nodules lacking any local or pulmonary lymphovascular emboli.

Figure 12:
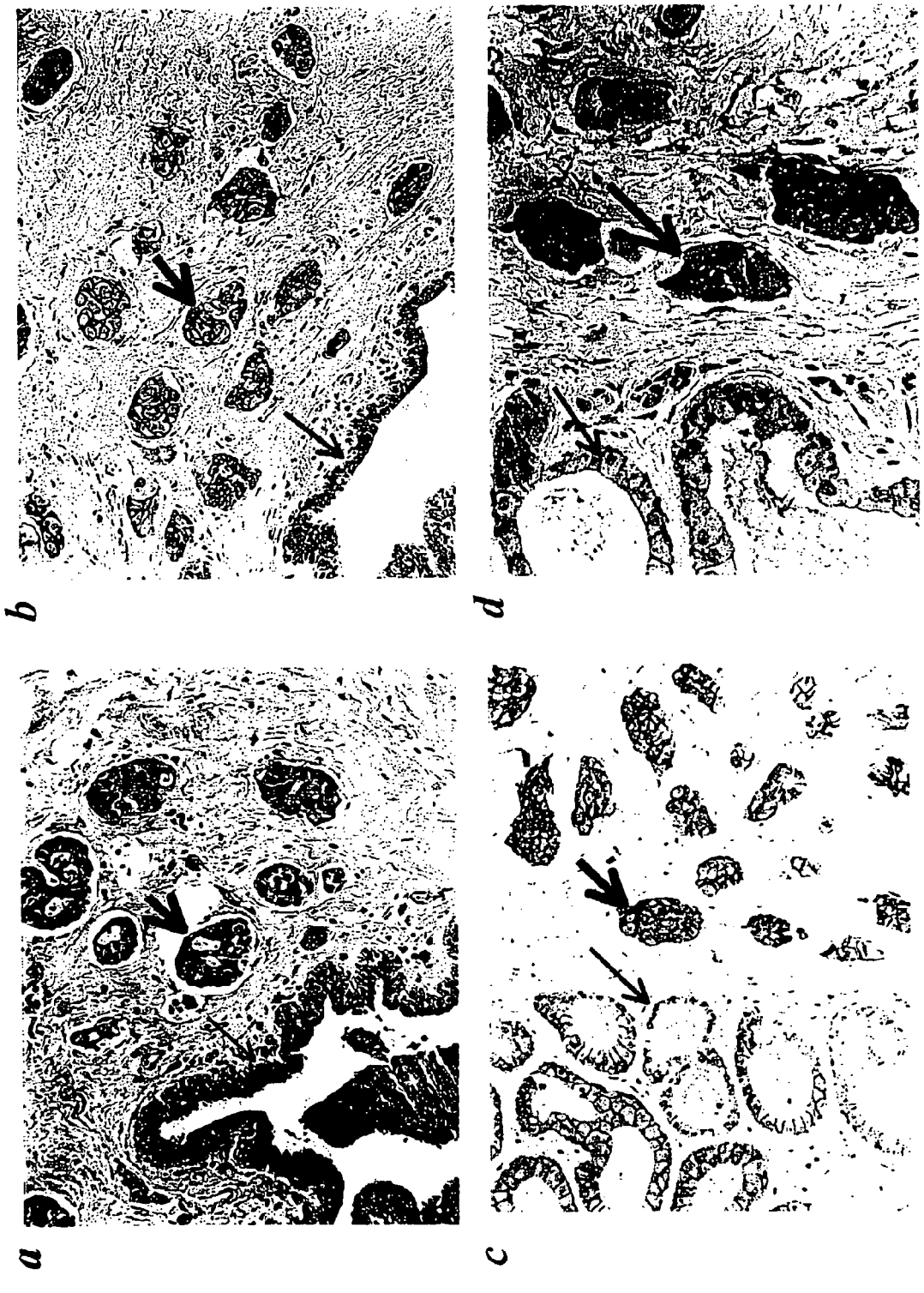
FIG. 12: 2 representative cases of human ibc are depicted. a, Lymphovascular emboli of the first case (bold arrow) lie adjacent to a normal duct (thin arrow), hematoxylin and eosin. b, These emboli (bold arrow) show increased E-cadherin membrane immunoreactivity compared to the normal ductal epithelium (thin arrow). C, Lymphovascular emboli of the second case (bold arrow) again show increased E-cadherin membrane immunoreactivity compared to the normal epithelium in a focus of adenosis (thin arrow). d, High power magnification of this immunoreactivity also shows that, within the normal epithelium, the E-cadherin immunoreactiviy is confined to the lateral borders between cells (the adherens junctions) (thin arrow) whereas in the lymphovascular emboli (thick arrow), the E-cadherin membrane immunoreactivity is circumferentially distributed about the cell (thick arrow).

Observations with MARY-X are applicable to the inflammatory phenotype of human ibc. In 25 cases of ibc (FIG. 12a), E-cadherin membrane immunoreactivity was present in all cases and increased in intensity in 90% of these cases within the lymphovascular emboli compared to adjacent normal ducts and acini (FIGS. 12b, 12c) and to most non-inflammatory breast carcinomas. In non-inflammatory breast carcinomas E-cadherin immunoreactivity was either lost or decreased in some of the cancers, especially the infiltrating lobular carcinomas, or retained at relatively normal levels, especially in the well and moderately-well differentiated ductal carcinomas, but was not increased as it was in 90% of the inflammatory carcinomas. Not only was the overall immunoreactivity increased in ibc but the distribution of immunoreactivity was altered. In the normal ducts and acini the E-cadherin immunoreactivity was confined to the lateral adherens junctions whereas in the lymphovascular emboli of ibc it was circumferentially distributed (FIG. 12d). α and β-catenin membrane immunoreactivity was also increased in the vast majority of these ibc cases; nuclear β-catenin immunoreactivity was not observed. Since MARY-X was established from a human inflammatory breast cancer and exhibited the phenotype of florid lymphovascular invasion and emboli formation, and since both showed identical E-cadherin and catenin immunoreactivity, we feel that the experimental observations made with MARY-X were applicable to the majority of inflammatory breast cancers arising in man.

Immunoprecipitation and phosphotyrosine studies. Since phosphorylation of the E-cadherin adhesion complex especially β-catenin might influence the adhesion state of the complex, we measured the degree of phosphorylation by immunoprecipitation and Western blot studies. Immunoprecipitation of tumoral and cellular extracts (MARY-X, HMS-3X and HMEC) was achieved by incubation with an anti-E-cadherin antibody followed by precipitation with a rabbit anti-mouse conjugated to Sepharose A (Transduction Laboratories). The precipitate was resuspended in Laemmli buffer and run on a 7.5% SDS-PAGE followed by Western blot transfer. Antiphosphotyrosine antibodies were used to probe the blot. The band intensity of the 92 kD band thought to be β-catenin was measured and normalized against the β-catenin protein levels of whole tumoral extracts. The degree of phosphorylation of β-catenin in MARY-X was compared to the levels observed in HMS-3X and HMEC. A second immunoprecipitation strategy employing anti-β-catenin instead of anti-E-cadherin was used to compare results.

Antibodies. The antibodies used included monoclonal antibodies to α-catenin and β-catenin (Transduction Laboratories, Lexington, Ky.) each at a concentration of 1 ug/ml; E-cadherin (clone HECD-1) at a concentration of 1–10 ug/ml (Zymed Laboratories, San Francisco, Calif.); actin (Sigma) (IgG2a, clone AC-40) at a 1:500 dilution, control mouse IgG1 (Dako, Denmark) at a concentration of 50 ug/ml; MUC-1, (clone HMPV, mouse IgG1) (PharMingen), at a concentration of 1–100 ug/ml; CD44 at a 1:1000 dilution, a gift of Dr. Graeme Doughtery, UCLA; VEGF, PD-ECGF, bFGF, aFGF, TGF-α, TGF-β, angiogenin, HGF, and HB-ECGF (all from R&D Systems, Minneapolis, Minn.).

Retroviral transfection studies. Retroviral plasmids (2.0 pmol) containing either the GFP reporter gene (pMSCV-GFP) (Clontech, Palo Alto, Calif.) ((Hawley et al., *Proc. Natl. Acad. Sci.* 93:10297–10302 (1996)), a dominant negative E-cadherin mutant (pBabe-H-2$K^d$-E-cad) or its control (pBabe-H-2$K^d$-E-cad ΨC25) (gifts of Dr. Fiona Watt, Imperial Cancer Research Fund, London, UK) were used in conjunction with a packaging plasmid (1.2 pmol) (pCL-Ampho) (Imgenex, San Diego, Calif.) to transiently transfect 293T cells ($10^6$ cells) via a calcium phosphate transfection method Zhu et al., *J. Cell Science* 109:3013–3023 (1996); and Naviaux et al., *J. Virol.* 70:5701–5705 (1996)). The 293T cells were a derivative of the adenovirus-transformed E1A-expressing human embryonic kidney cell line which had been previously transfected with a simian virus 40 large T-antigen to amplify the transfected pCL-DNA. Harvesting of the viral supernatants in conditioned media (Isocoves with 10% FCS) was begun at 36 hours post transfection and collected every 4–6 hours up to 72 hours. 25 ml of viral supernatant was filter sterilized through a 0.45 μm pore size filter and used in subsequent experiments. This approach produced high titres ($10^6$–$10^7$ cfu/ml) of helper-free retrovirus containing the desired constructs. The dominant negative E-cadherin mutant (H-2 $K^d$-E-cad) encoded a 66 kDa chimeric protein consisting of the extracellular domain of H-2 $K^d$ (297 ammo acids) linked to the C terminal 191 amino acids of mouse E-cadherin, which comprised 16 amino acids of the extracellular domain and the entire transmembrane and cytoplasmic domains containing the catenin binding site. As a control a construct (H-2 $K^d$-E-cad ΨC25) was derived from this dominant negative mutant in which the catenin binding site had been destroyed by a 25 amino acid deletion in the cytoplasmic domain (Zhu et al., *J. Cell Science* 109:3013–3023 (1996). The filtered undiluted retroviral supernatants were used immediately in some experiments or aliquoted and stored at −70° C. for later use. $10^3$–$10^4$ spheroids of MARY-X (average size 100–200 μm diameter) were plated onto 60 mm dishes in 2 ml of viral supernatant in the presence of polybrene (8 μg/ml) according to the parameters previously defined for the retroviral infection of spheroidal aggregates in suspension (Fujiwara et al., *Cancer Res.* 53:4129–4133 (1993)). Infection was carried out in a humidified incubator at 37° C. in an air-5% $CO_2$ atmosphere at constant humidity over 3 hours. After this the viral supernatant was removed and the spheroids were placed in DMEM with 10% FCS. After 48 hours and over the next 72 hours the spheroids were observed for gene expression and/or phenotypic changes. GFP expression was determined with an inverted Nikon fluorescent microscope. The presence of H-2$K^d$ (Noun et al., *J. Immunol.* 157: 2455–2461 (1996)) was determined by incubating the spheroids with a FITC-conjugated rat anti mouse H-2$K^d$ monoclonal antibody (Seikagaku Co., Tokyo, Japan) at $1/10$–$1/100$ dilutions at room temperature for 1–2 hours followed by thorough washings. In some experiments the spheroids were permeabilized with absolute methanol for 20 minutes at −20° C. prior to incubation with antibody. H-2 $K^d$ expression was determined with an inverted Nikon fluorescent microscope as before.

Example 3

MARY-X In Vivo Cancer Model

The xenograft disclosed herein exhibits striking lymphovascular invasion in an immunocompromised host. In fact it does not grow as an isolated tumor nodule but grows exclusively within lymphovascular channels. Some of these channels are lymphatics and some are blood vessels confirmed by anti-vWf factor and anti-CD31 endothelial staining. Interestingly the skin overlying the inflammatory xenograft is intensely erythematous just as it is in humans presumably from the lymphovascular obstruction. In both the athymic (nude) mouse and the Scid, the inflammatory carcinoma xenograft exhibits a high degree of spontaneous metastasis as early as 6 weeks following local subcutaneous implantation. In contrast the non-inflammatory xenografts, 231 and 468 grow as isolated tumor nodules exhibiting no lymphovascular invasion and no metastasis.

MARY-X induced erythema in the overlying mouse skin (FIG. 1A) mimicking the clinical presentation of inflammatory carcinoma. While all other human xenografts grow as isolated subcutaneous nodules, MARY-X grows exclusively within murine lymphatic and blood vessel channels (FIGS. 1B, 1C, 1D). MARY-X's supporting stroma comprises, by murine Cot-1 DNA analysis, 30% of the tumor. MARY-X, like its human counterpart exhibits striking erythema of the overlying skin. Confirmation of the vascular identity of these channels was on the basis of von Willebrand factor immunoreactivity. Analysis of the lungs of mice with large MARY-X tumors (1.5–2.0 cm diameter) reveals the presence of pulmonary metastases but surprisingly these metastases were confined to within vessels (FIG. 1E). No extravasation of these pulmonary metastases occurs. The phenotype of MARY-X is therefore limited to intravasation. This phenotype has remained stable in over 15 transplant generations.

We have conclusively shown that the blood vessels and lymphatics in MARY-X are murine and not human in origin because the purified human MARY-X "shake", when injected into nude or scid mice, produces the inflammatory phenotype of florid lymphovascular invasion which is characterized by a significant (30%) murine component as determined by the murine specific COT-1 probe (FIG. 2). One can use antibodies to markers such as von Willebrand factor (all blood vessels and lymphatics (weaker staining)), CD31 (all blood vessels and lymphatics (weaker staining)), PAL-E, a blood vessel endothelial antigen (all blood vessels), E-selectin (angiogenic blood vessels) and VEGF-3 (all lymphatics).

Example 4

Evaluating Diagnostic and Therapeutic Agents Utilizing MARY-X In Vitro and In Vivo Cancer Models Triton X-100 solubility assay. The MARY-X "shake" was obtained as stated above except a sterile screen filter was used to select for the smallest tumor cell aggregates (spheroids). In the assay to investigate the effect of $Ca^{++}$ on the partitioning of E-cadherin the shake was incubated in either 1xPBS containing 1 mM $CaCl_2$ or no calcium for 1 hour at room temperature. The "shake" was then subjected to a short (10 minutes) and a prolonged (30 minutes) extraction. The "shake" was suspended in extraction buffer (0.5% Triton X-100, 300 mM sucrose, 10 mM Pipes (pH6.8), 50 mM NaCl, 3 mM $MgCl_2$) and gently agitated at 4° C. for 10 or 30 minutes. The samples were then centrifuged at 10,000 g for 15 minutes at 4° C. The supernatant was removed as the soluble (S) fraction and the particulate (P) fraction was resuspended in a 2xLaemmli under reducing conditions (volume equal to supernatant). Equal volumes of the soluble and particulate fractions were then loaded onto 7.5% SDS-PAGE. PC-3 cells were grown to confluency on 100 mm plates, the cells were washed with 1xPBS and 500 ul of extraction buffer and similarly treated.

In vitro spheroid disadherence assays. MARY-X spheroids were individually placed into wells of a 96 well plate containing 50 ul of media: KSFM+1 mM $CaCl_2$, calcium free-KFSM or E-cadherin antibody (50–100 ug/ml in KFSM+$CaCl_2$). Anti-MUC-1, anti-CD44 and mouse IgG1 were separately used as control antibodies in the same concentrations. The spheroids were monitored for disadherence by visualization under a phase contrast microscope at successive time points: 2 hrs, 6 hrs, 12 hrs, 16 hrs, 24 hrs, 36 hrs, 48 hrs. Control xenograft aggregates derived from MDA-MB-231, MDA-MB-468 and HMS-3X, control cellular aggregates derived from HMEC, HUVEC and normal kidney were also used.

Murine tumorigenicity, histopathology, immunolocalization and embolic dissolution studies. Mice with known pulmonary lymphovascular emboli of MARY-X, received a single intravenous tail vein injection of anti-E-cadherin (20 µg/100 µl) or control (murine IgG1) for immunolocalization studies and daily injections of anti-E-cadherin (100 µg/100 µl) or control for five successive days for embolic dissolution studies. In the immunolocalization studies, the mice were sacrificed 90 minutes after receiving the antibodies; in the embolic dissolution studies the mice were sacrificed 24 hours after the last injections. Removed lungs were inflated, OCT embedded, sectioned and subjected to standard immunocytochemical protocols. The presence, immunoreactivity, number and size of pulmonary lymphovascular emboli/unit area of the lung were tabulated with the assistance of digital image analysis. The MARY-X spheroids which had been transfected ex vivo with the GFP reporter, the dominant negative E-cadherin mutant and control were reinjected into mice and tumorigenicity, histopathology, and presence of primary and pulmonary lymphovascular emboli formation was recorded.

Studies of human ibc cases. 25 cases of ibc were retrieved from archival pathological material and studied immunocytochemically with standard protocols. Non-ibc and normal breast tissues were used as controls.

Statistical analysis. Experiments were performed with groups of 10 mice and results analyzed with standard tests of significance, including the 2-tailed Student's t-test and a one-way analysis of variance (ANOVA).

Institutional certifications. Informed patient consent and approvals from the UCLA Human Subject Protection Committee, the Chancellor's Animal Research Committee (certification ARC 95-127-11), and the UCLA Institutional Biosafety Committee (IBC) were obtained prior to all studies.

Example 5

Utilizing MARY-X in a Model of How Palpation Effect Tumor Metastasis

Palpation of breast cancer invariably occurs during breast self-examination, physical examination, compression mammography and breast conservation surgery and the question arises whether such palpation abets tumor metastasis. As disclosed below, we investigate this question mechanistically by examining the effects of palpation on three different human tumoral xenograft/scid models: a non-metastatic human breast carcinoma xenograft (MDA-MB-231), a highly metastatic xenograft (C8161) which metastasizes as single cells and the unique inflammatory breast carcinoma xenograft (MARY-X) as disclosed herein which exhibits florid local lymphovascular emboli or lymphovascular invasion (L.V.I).

Palpation of each xenograft similarly increased intratumoral pressure by >200 percent (10x30 mm Hg) but dramatically increased the numbers and sizes of pulmonary metastases 10–100 fold (p<0.001) in only the inflammatory breast carcinoma xenograft. The mechanism of this effect was through an immediate post-palpation release of circulating tumor cells detected 2–3 minutes after palpation (p<0.01) by human cytokeratin 19 RT-PCR of extracted RNA from 300 ul of murine blood. Although circulating human tumor cell-derived growth factors (gGF-I, IGF-II, TGF-α and TGF-β) and angiogenic factors (VEGF and bFGF) were detected by ELISA to be in the pg to ng range in murine serum of MARY-X, palpation of this xenograft did not further increase the circulating levels of these factors (p>0.1). Palpation also did not result in the release of circulating tumor cells (p>0.1) from the non-metastatic xenograft (p>0.1) nor the highly metastatic xenograft which metastasizes as single cells (p>0.1). Therefore palpation promotes only a very specific step of the metastatic process, tumor dissemination of pre-existing lymphovascular emboli but not intravasation, extravasation or growth per se. Hence human breast cancers exhibiting an exaggerated degree of L.V.I. might be particularly susceptible to palpation-induced metastasis.

Materials and Methods

Establishment of MARY-X. Informed patient consent and certification from the UCLA Human Subject Protection Committee was obtained prior to all studies. Approval from the Chancellor's Animal Research Committee was requested and obtained (certification ARC 95-127-11). MARY-X was established from a patient with ibc and exhibited the phenotype of florid local lymphovascular invasion (L.V.I.) and florid local lymphovascular emboli formation in nude/scid mice (Alpaugh et al, Cancer Res., 59: 5079–5084, 1999). MARY-X also gave rise to low levels of pulmonary lymphovascular emboli. In the primary MARY-X the murine component was considerable (~30%). The MARY-X "shake", an enriched population of MARY-X spheroids, 99% free from murine components, was produced as described previously (Alpaugh et al, Cancer Res., 59: 5079–5084, 1999). MARY-X was transplanted into the ventrolateral flanks of nude and scid mice (Charles Rivers) and allowed to grow into 1.0 cm diameter tumors.

Other cell lines and xenografts. The MDA-MB-231 line was obtained from the American Type Culture Collection (ATCC) (Rockville, Md.) and the C8161 human melanoma cell line (a gift of Dr. Mary Hendrix, University of Iowa) were grown in MEM containing 10% fetal calf serum and antibiotics (100 units/ml penicillin and 100 $\mu$g/ml streptomycin) at 37° C. in an air-5% $CO_2$ atmosphere at constant humidity. The MDA-MB-231 line which is fully tumorigenic in the absence of estrogen is non-metastatic in scid and athymic mice. The highly metastatic C8161 line, originally derived from a patient with amelanotic melanoma, but which manifests an undifferentiated carcinomatous phenotype with expression of numerous epithelial keratins is thought to metastasize as single cells (Barsky et al, Oncogene, 15: 2077–2091, 1997). The C8161 line is fully tumorigenic and exhibits a high degree of spontaneous pulmonary metastasis but does not manifest lymphovascular emboli nor obvious L.V.I. at the primary tumor site. Our previous studies with this line and xenograft demonstrated that the earliest metastases were present as single cells within the lung (Barsky et al, Oncogene, 15: 2077–2091, 1997). Hence it could be concluded that this xenograft metastasized as such, in contrast to the situation with MARY-X, where the earliest metastases were observed to be lymphovascular emboli within the lungs consisting of at least 5–10 cells. Corresponding xenografts of MDA-MB-231 and C8161 were generated by injections of $1 \times 10^6$ cells/200$\lambda$ subcutaneously into the ventrolateral flanks of nude and scid mice (Charles Rivers) and allowed to grow into 1.0 cm diameter tumors.

Palpation studies. Palpation studies were initiated when the xenografts reached a size of 1.0 cm. Each mouse was grasped and held in the supine position and the tumor was palpated between the forefinger and thumb (repeated 15 consecutive times). Palpation was conducted every third day over a two week period during which time the xenografts increased from 1.0 cm to 1.5 cm in diameter.

Monitoring of intratumoral pressure. Intratumor pressures were measured in selected mice (3 from each group) using a 22 gauge needle introduced into the tumor parenchyma attached in series to a disposable Baxter PX260 transducer (Irvine, Calif.), a Spacelabs Medical module ultraview 1600 and a Spacelabs Medical ultraview 1700 monitor. Five separate intratumoral pressure measurements (center and 4 quadrants) were made for each xenograft and the average pressure recorded. Intratumoral pressure measurements were recorded before, during, and after palpation.

Animal studies and statistical analysis. Female scid and athymic (nude) mice (nu/nu mutants on a BALB/c background) were used in all studies. Experiments were performed with groups of 10 mice. At the end of the period of palpation, the xenografts were measured, extirpated and examined histologically. The lungs were removed, inflated, embedded, sectioned and stained with hematoxylin and eosin and a monoclonal antibody cocktail to cytokeratins 8,18, 19 (DAKO, Carpinteria, Calif.). The presence, immunoreactivity, number and size of pulmonary lymphovascular emboli and/or metastatic colonies in mid-longitudinal cross-section of lung were determined. Results were tabulated with the assistance of digital image analysis and expressed as mean±standard error of the mean for 20 lungs (10 mice) in each group and. Results were analyzed with standard tests of significance, including the 2-tailed Student's t-test and a one-way analysis of variance (ANOVA).

RT-PCR studies. The xenografts were excised and immediately frozen in liquid nitrogen and pulverized with mortar and pestle to a fine powder and subjected to RNA extraction using Trizol reagent (Gibco-BRL). RNA extraction was also performed on the MARY-X "shake", the enriched population of MARY-X spheroids. RT-PCR for human cytokeratin 19 (Battaglia et al, Bone Marrow Transplant., 22: 693–98, 1998) was initially performed on 30 ng of this extracted tumoral RNA to verify whether this gene was expressed at significant levels in the three different cell lines/xenografts being studied, MDA-MB-231, C8161 and MARY-X to make it a useful target. The cytokeratin 19 RT-PCR was next performed on RNA extracted from varying numbers of human tumor cells (30,000×1) mixed with 300$\lambda$ of murine blood to determine the sensitivity of this assay for detecting human tumor cells in a murine background. Finally the cytokeratin 19 RT-PCR was performed on RNA extracted from murine blood obtained from the groups of palpated v non-palpated xenografts. 300$\lambda$ blood was obtained from right heart puncture with a 22 gauge needle 2–3 minutes after palpation of 1.5 cm sized xenografts. RNA was extracted with the Qiagen QIAamp RNA Blood Mini Kit (Qiagen, Inc., Valencia, Calif.) according to the standard protocols provided in the kit. The RNA samples were further DNase I treated and RT-PCR was carried out using Ready-To-Go™ RT-PCR Beads (Amersham Pharmacia Biotech, Inc., Piscataway, N.J.). We followed the single tube protocol for RT-PCR (Battaglia et al, Bone Marrow Transplant., 22: 693–98, 1998), using pd(T)12-18 as the first strand primer for reverse transcription. PCR was then carried out using two primers for human cytokeratin 19 which amplified a 209 bp product. This reaction was carried out in 1 mM $MgSO_4$ with 200 $\mu$M dNTPs. Using a Perkins-Elmer Cetus DNA Thermal Cycler, the cDNA copy of the cytokeratin 19 sequence was created with 10 U Avian Myeloblastosis Virus Reverse Transcriptase (AMV) in 5X reaction buffer by incubating the samples at 42° C. for 27 minutes, then 5 minutes at 95° C. to deactivate the AMV, then 4° C. at which time the cytokeratin 19 sense and antisense primers were added together with 5 U Thermus flavus DNA Polymerase (Tft). Next, the PCR program was carried out as follows: 94° C. for 30 seconds, 58° C. for 1 minute, 68° C. for 2 minutes (30 cycles) and 7 minutes at 68° C. (one cycle). The RT-PCR products (15$\lambda$) were separated on a 2% agarose gel at 80V for 1 hour, then stained with ethidium bromide and photographed with the Gel Doc 1000 System and Software (BioRad).

ELISA studies. We examined murine serum of palpated v non-palpated MARY-X for levels of the following factors: IGF-I, IGF-II, TGF-α, TGF-β, VEGF and bFGF. We used the quantitative sandwich enzyme immunoassay (ELISA) for VEGF, bFGF, IGF-I and TGF-β. (R&D Systems, Minneapolis, Minn.). We used a modified ELISA for IGF-II (PeproTech, Inc., Rocky Hill, N.J.) and TGF-α (Oncogene Research Products, Cambridge, Mass.). These assays could detect circulating human growth and angiogenic factors in murine serum to levels as low as 5–25 pg/ml. 300λ blood was obtained from right heart puncture 2–3 minutes after palpation. A serum separator tube allowed samples to clot for 30 minutes prior to centrifugation for 10 min at 1000×g. Serum samples were assayed immediately.

Results

Figure 13:
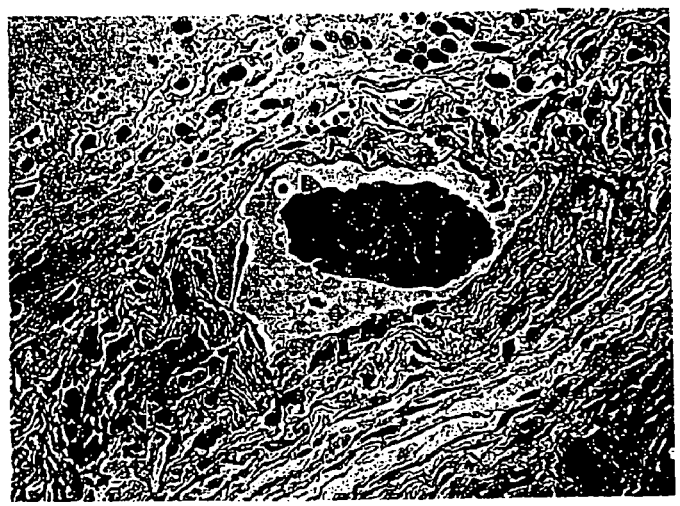
FIG. 13: (A) Primary lymphovascular tumor embolus of MARY-X is depicted. (B) Non-palpated MARY-X spontaneously gives rise to low levels of pulmonary lymphovascular emboli. (C) After palpation, however, numbers and sizes of pulmonary lymphovascular emboli increase dramatically. (D) Quantitation of number of pulmonary tumor emboli and number of cells/embolus reveals that palpation significantly increases both numbers and sizes of pulmonary lymphovascular emboli in MARY-X. (E) In contrast, though the metastasizing C8161 xenograft exhibits a higher spontaneous rate of metastasis than MARY-X, palpation exerts no promotional effects upon this process. The MDA-MB-231 xenograft remains non-metastatic with and without palpation.
Figure 13:
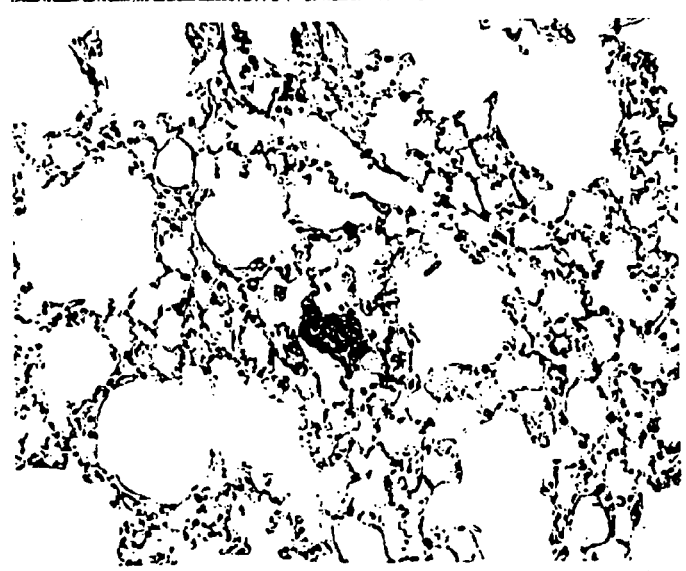
Figure 13:
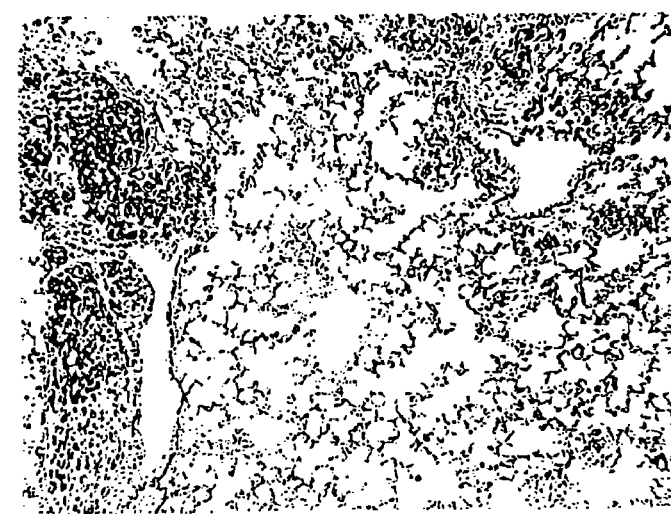
Figure 13:
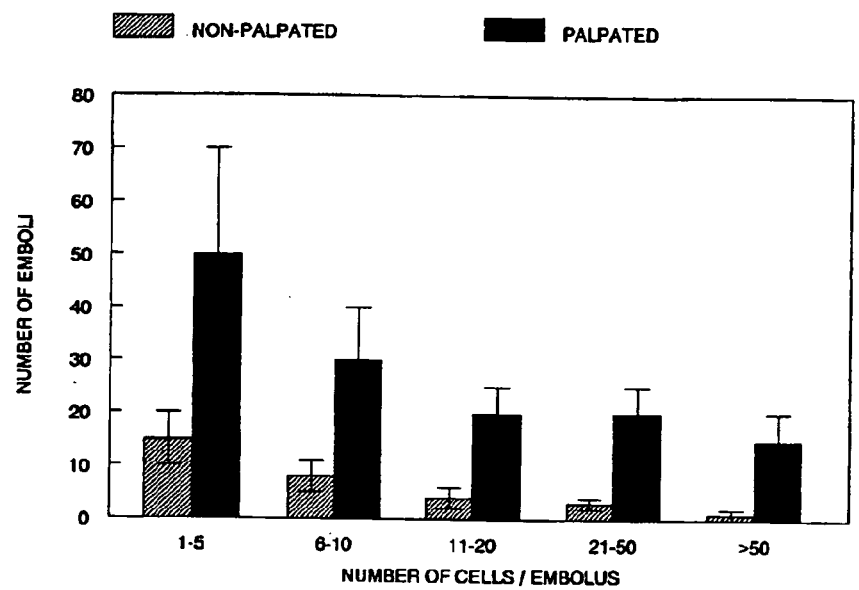
Figure 13:
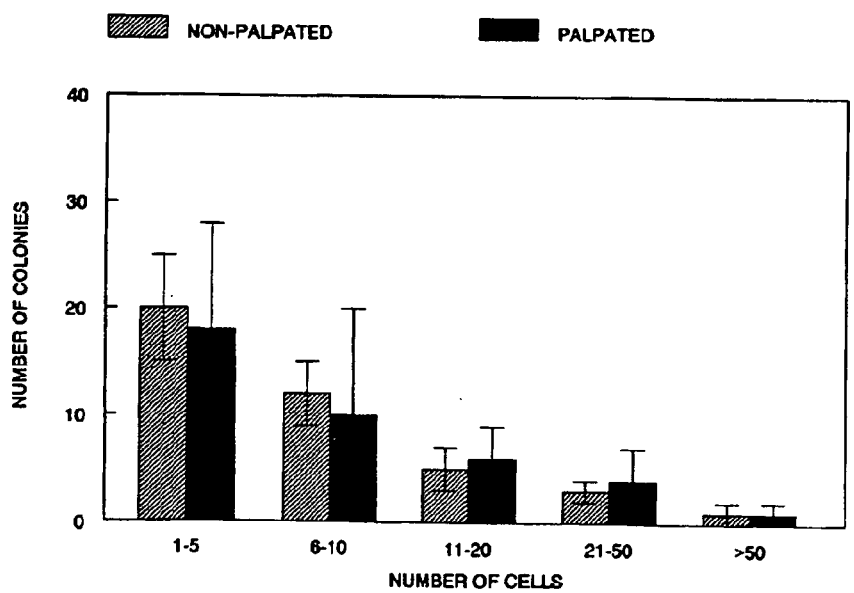

Palpation resulted in a similar increase in intratumoral pressure in all three xenograft groups. During palpation, intratumoral pressures increased by >200 percent (10×30 mm Hg) similarly in all xenografts (Table I). Palpation exerted no effects on tumor growth, size or histological characteristics in any of the primary xenografts but dramatically increased the numbers and sizes of pulmonary lymphovascular embolic metastases 10–100 fold ($p<0.001$) in the inflammatory breast carcinoma xenografts but did not induce metastasis in the non-metastatic xenograft ($p>0.1$) nor increase metastasis in the highly metastatic xenograft which metastasizes as single cells ($p>0.1$) (FIG. 13). The mechanism of this effect was through an immediate post-palpation release of circulating tumor cells detected 2–3 minutes after palpation ($p<0.01$) by human cytokeratin 19 RT-PCR of extracted RNA from 300 ul of murine blood. The human cytokeratin 19 gene proved a useful target in detecting and comparing circulating tumor cells among the C8161, the MDA-MB-231 and the MARY-X xenografts since the gene was expressed in all three xenografts. The human cytokeratin 19 gene target permitted the detection of as few as 30 cells/300λ murine blood and in fact could theoretically detect circulating C8161 or MDA-MB-231 cells easier than circulating MARY-X cells as the former gave stronger signals. This not withstanding human cytokeratin 19 RT-PCR detected circulating MARY-X cells ($p<0.01$) but not circulating MDA-MB-231 ($p>0.1$) or C8161 cells ($p>0.1$). Palpation produced an increase in circulating MARY-X cells (3–5 fold) ($p<0.01$) but still did not result in the detection of any MDA-MB-231 ($p>0.1$) or C8161 cells ($p>.0.1$).

Therefore the apparent cause of the palpation-induced increase in size and number of the pulmonary lymphovascular emboli in MARY-X was the palpation-mediated release of increased numbers of MARY-X tumor cells into the circulation. It should be recalled that MARY-X manifests an exaggerated degree of lymphovascular emboli formation or L.V.I. in the primary tumor whereas both the metastasizing C8161 and the non-metastasizing MDA-MB-231 do not. Palpation results in no detectable tumor cells being released into the circulation by either the non-metastasizing MDA-MB-231 or the highly metastasizing C8161. The pulmonary lymphovascular emboli which were induced by palpation exhibited not only an increase in number and size but also a range of histological features which illustrated potential mechanisms by which embolic dissemination enhanced subsequent metastasis. Pulmonary lymphovascular emboli were observed to be selectively adhering to endothelium, mechanically obstructing the vasculature, wedging at bifurcation points and serving as a nidus for fibrin and platelet accumulation.

Although circulating human tumor cell-derived growth factors (IGF-I, IGF-II, TGF-α and TGF-β) and angiogenic factors (VEGF and bFGF) in the pg to ng range were detected by ELISA in the murine serum of MARY-X, palpation of this xenograft did not increase the circulating levels of these factors ($p>0.1$).

These studies indicate that palpation promotes only a very specific step of the metastatic process: metastatic dissemination of intravascular tumor emboli (embolic dissemination) and not other steps of the metastatic process such as invasion, intravasation, extravasation or growth. It is interesting that palpation does not act indiscriminately in enhancing metastasis as an "old wives tale" would have it but specifically enhances only the dissemination of pre-existing lymphovascular emboli such as exists in MARY-X. Palpation did not induce metastasis in a non-metastasizing line, the MDA-MB-231 nor enhance metastasis in a highly metastasizing line, the C8161 which metastasizes as single cells rather than as lymphovascular emboli.

TABLE I

INTRATUMORAL PRESSURE WITH AND WITHOUT PALPATION

| TUMOR | PRESSURE (mm Hg) | PALPATED PRESSURE (mm Hg) | ϑP (PERCENTAGE INCREASE) |
|---|---|---|---|
| C8161-X | 10 ± 4[a] | 30 ± 5[b] | 20 (200)[c] |
| MDA-MB-231-X | 12 ± 6 | 34 ± 8 | 20 (183) |
| MARY-X | 12 ± 5 | 36 ± 8 | 24 (200) |

[a]5 measurements were made per tumor and 3 tumors in each group were sampled. Results depict mean pressure ± standard error.
[b]5 measurements were made per palpated tumor and 3 palpated tumors in each group were sampled. Results depict mean palpated pressure ± standard error.
[c]Change in pressure due to palpation is depicted. Results depict mean pressure change and are also expressed as percentage increase.

Example 6

Antibodies to MARY-X

Figure 14:
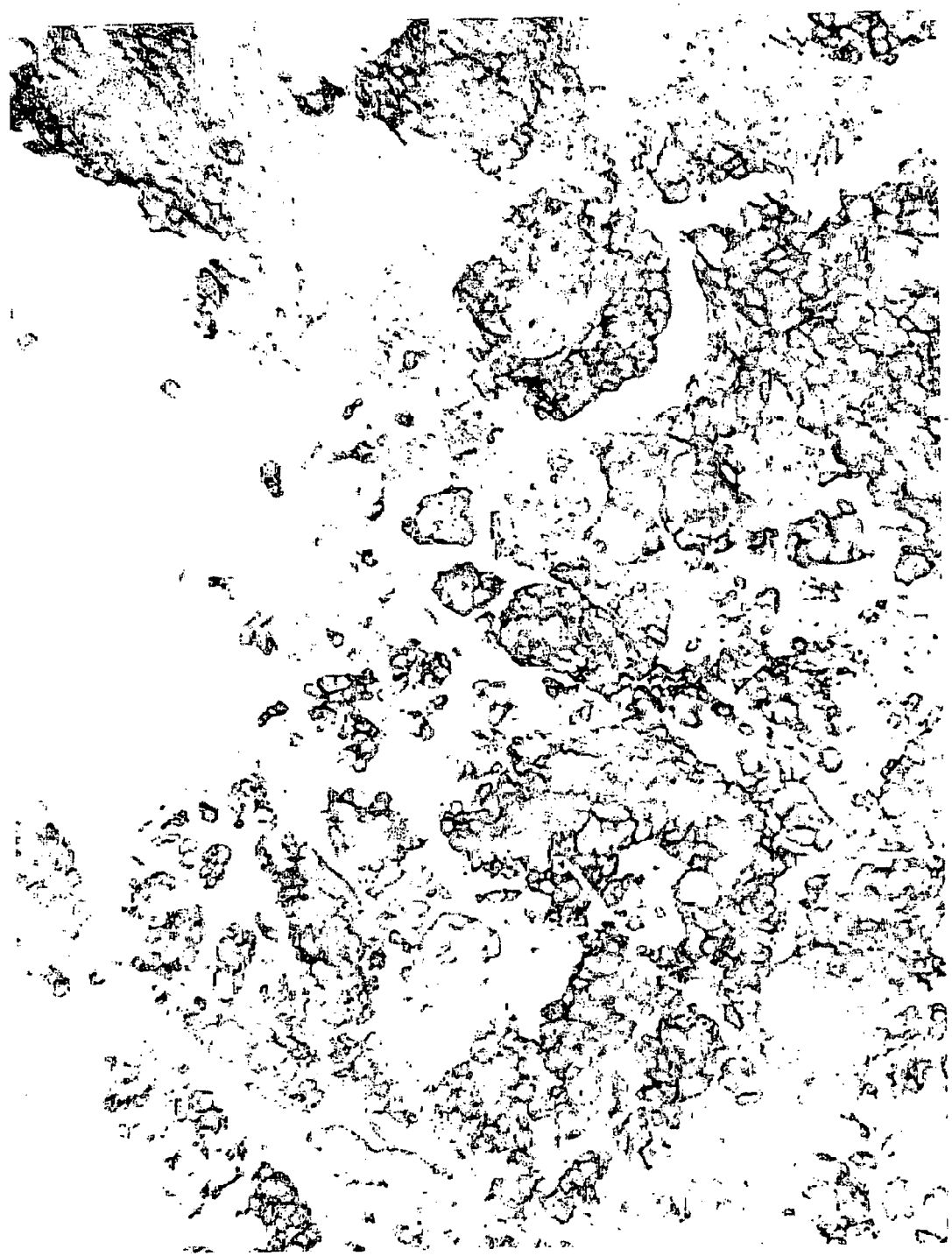
FIG. 14: When we permeabilized these spheroids with 70% ethanol, the membrane immunoreactivity observed with MARY-X antisera remained and there was no cytoplasmic immunoreactivity observed providing evidence. that the antisera of these mice contain a specific antibody (antibodies) to surface or membrane determinants of MARY-X cells.
Figure 15:
FIG. 15: With MARY-X antisera tested against a section of breast cancer, strong immunoreactivity was observed against membrane determinants of the breast cancer but not on the membranes of adjacent normal ducts or acini.

In order to generate antibodies to MARY-X xenograft, MARY-X cells were injected intraperitoneally (approximately 10[7]cells) into three groups of immunocompetent mice: the inbred BALB/c line, the outbred Swiss-Webster line (which are generally thought to give a more brisk immune response) and the outbred Swiss-Webster line at an inoculum escalation of 3 fold. All groups of mice were given a booster injection intraperitoneally (approximately 10[7] cells) three weeks later and a second booster three weeks from this first booster. At week 8 the mice were bled and the antisera was used to screen for immunoreactivity first against the spheroids of our human MARY-X line, then against sections of inflammatory and other breast cancers. As a comparison preimmune serum (serum of mice not injected with the spheroids) was tested against the spheroids of MARY-X. Preimmune sera showed no response whatsoever. In contrast the immunized mice showed a dramatic response in their antisera. At low, medium and high power there was intense membrane immunoreactivity of this antisera against cytopreparations of the MARY-X spheroids used to immunize the mice. The antisera was diluted initially 1/1000 so this immunoreactivity represented antibodies of high titre. The antibodies in the antisera obviously were recognizing antigenic determinants on the surface or membrane of the MARY-X cells. Since our MARY-X line is Her-2/neu negative this antigen is not Her-2/neu. When we permeabilized these spheroids with 70% ethanol, the membrane immunoreactivity remained and there was no cytoplasmic immunoreactivity observed (FIG. 14). Therefore the antisera of these mice contain a specific antibody (antibodies) to surface or membrane determinants of MARY-X cells. We then tested this antisera against a section of breast cancer, strong immunoreactivity was observed against membrane determinants of the breast cancer but not on the membranes of adjacent normal ducts or acini (FIG. 15).

Therefore we have been successful in producing an antisera against a membrane determinant(s) of MARY-X. We now plan to harvest the spleens of these mice, produce fusions with myeloma lines and obtain clones making monoclonal antibodies to surface determinants. The strong immunoreactivity of the antisera suggests that there are probably a number of different monoclonal antibodies some of which may be specific for inflammatory breast cancer, specific for non-inflammatory breast cancer, precancer (ductal carcinoma in situ DCIS)), some specific for subtypes of DCIS, e.g., comedo DCIS, some specific perhaps for just other stages of precancer. Each antibody so obtained with be screened for its spectrum of specificity. We may be able to produce a cocktail of antibodies each with its own specificity.

What is claimed is:

1. An isolated human inflammatory breast cancer xenograft, wherein the xenograft grows within lymphatic and blood vessel channels of an immunocompromised mouse and comprises the following properties:
    i) does not express estrogen receptor and progesterone receptor; and
    ii) expresses P53, EGFR, MUC1 and E-cadherin.

2. The xenograft of claim 1, wherein the Level of E-cadherin expressed by the xenograft is at least two-fold greater than the level of E-cadherin expressed by a noninflammatory breast cancer xenograft.

3. The xenograft of claim 2, wherein the xenograft expresses α-catenin and β-catenin and the levels of α-catenin and β-catenin expressed by the xenograft are at least two-fold greater than the levels of α-catenin and β-catenin expressed by a noninflammatory breast cancer xenograft.

4. The xenograft of claim 3, wherein the xenograft does not express Her-2/neu.

5. The isolated human inflammatory breast carcinoma xenograft of claim 1, wherein the isolated human inflammatory breast carcinoma xenograft is designated MARY-X and has American Type Culture Collection Accession Number PTA-2737.

6. An isolated in vitro culture of the human inflammatory breast cancer xenograft of claim 1, wherein the xenograft grows as a spheroid.

7. The in vitro culture of a human inflammatory breast cancer xenograft of claim 6, wherein the spheroid can attach to a cell monolayer.

8. The in vitro culture of a human inflammatory breast cancer xenograft of claim 7, wherein the spheroid disadheres from the cell monolayer when exposed to a culture media containing absent $Ca^{++}$ or anti-E-cadherin antibody.

9. A method of generating the xenograft of claim 1 comprising the steps of:
    (a) obtaining a breast sample from a patient;
    (b) identifying cells in the sample as an inflammatory carcinoma exhibiting florid invasion of dermal lymphatics and which comprises the following properties:
        i) do not express estrogen receptor and progesterone receptor; and
        ii) express P53, EGFR, MUC1 and E-cadherin;
    (c) implanting the sample into an immunocompromised mouse; and
    (d) identifying the xenograft growing in the immunocompromised mouse,
    so that an isolated human inflammatory breast cancer xenograft is generated, wherein the xenograft grows within lymphatic and blood vessel channels of an immunocompromised mouse and comprises the following properties:
        i) does not express estrogen receptor and progesterone receptor; and
        ii) expresses P53, EGFR, MUC1 and E-cadherin.

10. A mouse model for inflammatory breast cancer comprising an immunocompromised mouse inoculated with a human inflammatory breast cancer xenograft, wherein the xenograft grows within lymphatic and blood vessel channels and has the following properties:
    i) does not express estrogen receptor and progesterone receptor; and
    ii) expresses P53, EGFR, MUC1 and E-cadherin.

11. The mouse model according to claim 10, wherein the immunocompromised mouse is a nude mouse.

12. The mouse model according to claim 10, wherein the human inflammatory breast cancer xenograft, is the xenograft designated MARY-X and having American Type Culture Collection Accession Number PTA-2731.

13. A method of identifying a molecule whose expression is modulated in inflammatory breast cancer comprising the steps of:
    (a) providing a human inflammatory breast cancer xenograft, wherein the xenograft grows within lymphatic and blood vessel channels of an immunocompromised mouse and has the following properties:
        i) does not express estrogen receptor and progesterone receptor; and
        ii) expresses P53, EGFR, MUC1 and E-cadherin;
    (b) determining the level of expression of at least one molecule in the human in inflammatory breast cancer xenograft; and
    (c) comparing the level expression of the molecule in the human inflammatory breast cancer xenograft to the level of expression of the molecule in a cell having characteristics which are distinct from the human inflammatory breast cancer xenograft,
    so that a molecule whose expression is modulated in inflammatory breast cancer is identified.

14. The method according to claim 13, wherein the level of expression of the molecule of the inflammatory breast cancer xenograft is determined by a method selected from the group consisting of: Northern Blotting, Southern Blotting, Western Blotting and polymerase chain reaction.

15. The in vitro culture of a human inflammatory breast cancer xenograft of claim 6, wherein the xenograft is the xenograft having American Type Culture Collection Accession Number PTA-2736.

16. The mouse model for inflammatory breast cancer of claim 10, wherein the xenograft is the xenograft having American Type Culture Collection Accession Number PTA-2737.

17. The method of identifying a molecule whose expression is modulated in inflammatory breast cancer of claim 13, wherein the xenograft is the xenograft having Amen Type Culture Collection Accession Number PTA-2737.

* * * * *